United States Patent [19]
Zeelon et al.

[11] Patent Number: 5,858,970
[45] Date of Patent: Jan. 12, 1999

[54] POLYPEPTIDE HAVING FACTOR XA INHIBITORY ACTIVITY

[75] Inventors: Elisha P. Zeelon, Bet Dagan; Moshe M. Werber, Tel Aviv; Avigdor Levanon, Rehovot, all of Israel

[73] Assignee: Bio-Technology General Corp., Iselin, N.J.

[21] Appl. No.: 779,379

[22] Filed: Jan. 7, 1997

Related U.S. Application Data

[63] Continuation of Ser. No. 225,442, Apr. 8, 1994, abandoned, which is a continuation-in-part of Ser. No. 45,805, Apr. 9, 1993, abandoned.

[51] Int. Cl.$^6$ .......................... A61K 38/55; A61K 38/58; C07K 14/81; C07K 14/815
[52] U.S. Cl. ................................ 514/8; 514/12; 530/324; 530/350; 530/395; 530/858; 435/226
[58] Field of Search ..................... 514/8, 12; 530/324, 530/380, 395, 858; 424/537, 538; 435/212, 226

[56] References Cited

U.S. PATENT DOCUMENTS

| | | | |
|---|---|---|---|
| 4,588,587 | 5/1986 | Gasic | 514/21 |
| 4,742,004 | 5/1988 | Hartman et al. | 435/189 |
| 4,791,100 | 12/1988 | Kramer et al. | 514/12 |
| 4,832,849 | 5/1989 | Cardin | 210/635 |
| 5,114,922 | 5/1992 | Maschler | 514/12 |
| 5,182,113 | 1/1993 | Rigbi | 424/537 |
| 5,403,596 | 4/1995 | Rigbi | 424/537 |

FOREIGN PATENT DOCUMENTS

| | | |
|---|---|---|
| 0263608 | 4/1988 | European Pat. Off. . |
| 0346894 | 12/1989 | European Pat. Off. . |
| 0352903 | 3/1994 | European Pat. Off. . |

OTHER PUBLICATIONS

Baskova et al., Chemical Abstracts, 106:60996w (1986).
Condra et al., "Isolation and Structural Characterization of a Potent Inhibitor of Coagulation Factor Xa from the Leech *Haementeria ghilianii*", Thrombosis and Homeostasis 61(3): 437–441 (1989).
Methodologies for Protein Disposition Studies, Protein Pharmacokinetics and Metabolism; Plenum Press. New York, 1992. pp. 1–33.
Han et al., (1989) "Cloning and Expression of cDNA Encoding Antistasin, a Leech–Derived Protein Having Anti–Coagulant and Anti–Metastatic Properties", Gene 75:47–57.
Gasic et al., Cancer Res. 44:1633–1636 (1983).
Gasic et al., Cancer Res. 44:5670–5676 (1984).
Gasic et al., Chemical Abstracts 110:185955w (1986).
Hoffman et al., (1992) "Site–Directed Mutagenesis of the Leech–Derived Factor Xa Inhibitor Antistasin", Journ. Biol. Chem., 287:943–949.
Hopp et al., (1988) "A Short Polypeptide Marker Sequence Useful For Recombinant Protein Identification And Purification", Bio/technology 6:1204–1210.
Konrad, Michael W., (1993) "The Immune System as a Barrier to Delivery of Protein Therapeutics", Biological Barriers to Protein Delivery Plenum Press, New York. pp. 409–437.
Nutt et al., (1988) "The Amino Acid Sequence of Antistasin", Journ. Biol. Chem. 263(11): 10162–10164.
Rigbi et al., (1990) Chemical Abstracts, 113:46259W.
Tuszynski et al., (1987) "Isolation and Characterization of Antistasin", 262(20): 9718–9723.
Dunwiddie et al. (1989), J.Biol. Chem. 264(28): 16694–16699.
Sollner et al., Eur. J. Biochem. 219: 937–943 (1994).

*Primary Examiner*—Dian C. Jacobson
*Attorney, Agent, or Firm*—John P. White; Cooper & Dunham LLP

[57] ABSTRACT

A novel polypeptide derived from the leech *Hirudo medicinalis* was found to be able to inhibit Factor Xa thereby reducing the extent of blood coagulation. The polypeptide is useful in treating conditions of excessive blood coagulation. A recombinant organism containing cDNA encoding the polypeptide has been deposited in the ATCC under Accession No. 69134. Recombinant microorganisms able to produce the polypeptide have been deposited in the ATCC under Accession Nos. 69135, 69137 and 69269.

9 Claims, 26 Drawing Sheets

FIGURE 3
SEQ. I.D. NOS. 18-20

```
a.a.#        -20                -10                 1                  11                 21
PCR4
13      KMCWNKGCPC      GQRCNLHRNE      YEVMYVDDPC      EDSDCEDGNK      CSPVTNECDC
AS                                      CEVIAENIEC      QEEECPDPYL      CSPVTNRCEC
                                        <EGPFGPGC       EEAGCPEGSA      CNIITDRCTC a.a.#        31                 41                 51                 61                 71
PCR4    SPVRCRLHCN      F-YVKDSNGC      ETCAC-----      EPKCKHKNCS      TGHHCNKLTN
13      TPVLCRMYCK      F-WAKDEKGC      EICKC-----      EELCQNQNCT      KDMLCSSVTN
AS      SGVRCRMHCP      HGFQRSRYGC      EFCKCRLEPM      KATCDISECP      EGMMCSRLTN a.a.#        81                 91                101                 111                121
PCR4    KC---ELKKQ      RRMG
13      RCDCQ-DFKC      PQSYCPHGFE      TDENECEVCI      CKKPTCANCG      KTTKKPRTID
AS      KCDCKIDINC      -RKTCPNGLK      RDKLGCEYCE      CRPKRKLIPR      LS a.a.#        131                141
13      RLKNWFKKKF      GK
```

FIGURE 5

SEQ. I.D. NOS. 22-23

```
                    Met Tyr Glu Val Met Tyr Val Asp Asp Pro Cys Glu Asp     13
      GGA ATT CAT  ATG TAT GAG GTG ATG TAT GTG GAC GAT CCA TGT GAG GAT      48

14   Ser Asp Cys Glu Asp Gly Asn Lys Cys Ser Pro Val Thr Asn Glu Cys       29
 49   TCA GAC TGT GAA GAT GGA AAC AAA TGC AGT CCT GTG ACC AAT GAA TGC       96

30   Asp Cys Ser Pro Val Arg Cys Arg Leu His Cys Asn Phe Tyr Val Lys       45
 97   GAT TGC TCT CCT GTG CGA TGC AGA TTG CAT TGC AAT TTT TAC GTC AAA      144

46   Asp Ser Asn Gly Cys Glu Thr Cys Ala Cys Glu Pro Lys Cys Lys His       61
145   GAC AGT AAT GGC TGT GAG ACA TGC GCT TGT GAG CCT AAA TGC AAG CAT      192

62   Lys Asn Cys Ser Thr Gly His His Cys Asn Lys Leu Thr Asn Lys Cys       77
193   AAA AAT TGT TCA ACT GGC CAT CAC TGC AAC AAA TTG ACA AAC AAG TGT      240

78   Glu Leu Lys Lys Gln Arg Arg Met Gly *** Thr Lys Ile *** Lys Lys       93
241   GAA TTA AAA AAG CAA CGA AGA ATG GGA TAG ACC AAA ATA TAA AAA AAA      288

94   Arg Lys Lys Leu Arg Lys Lys Asp Ser Leu Glu Ile Leu *** Arg ***      109
289   AGA AAG AAG CTG AGA AAA AAA GAT TCC CTG GAG ATT CTC TGA CGA TAA      336

110   Ile Ser Asn Ile Leu Thr Tyr Leu Phe Val Val Pro Leu Ile Asn Met      125
337   ATT AGC AAC ATA TTG ACT TAC TTA TTC GTA GTT CCG TTA ATA AAC ATG      384

126   Val Ser *** Ile Asn Ile Glu Glu Glu Leu Tyr Phe Ile Val Arg Ile      141
385   GTT TCC TAA ATA AAT ATT GAA GAA GAA CTA TAT TTT ATT GTT CGC ATA      432

142   Ser Thr Phe Lys Met Ser Lys Lys Lys Lys Lys Lys
433   TCA ACA TTC AAA ATG TCA AAA AAA AAA AAA AAA A
```

FIGURE 7

SEQ. I.D. NOS. 24-25

|  |  |  |  |  |  |  |  |  |  |  |  |  |  |  |  |  |
|---|---|---|---|---|---|---|---|---|---|---|---|---|---|---|---|---|
|  | CG | GAA | TCT | TGT | AAG | GAT | AAT | AGA | TCT | TGC | CGT | AGC | GAT | GAA | CGT | TGT | 47 |

|  |  |  |  |  |  |  |  |  |  |  |  | Met | Lys | 2 |
|---|---|---|---|---|---|---|---|---|---|---|---|---|---|---|
| 48 | GAT | AAC | TTC | ACC | AAA | GTG | TGT | GTT | CCT | CAA | TCA | TTC | GAA | GAA | ATG | AAA | 95 |

| 3 | Met | Cys | Trp | Asn | Lys | Gly | Cys | Pro | Cys | Gly | Gln | Arg | Cys | Asn | Leu | His | 18 |
|---|---|---|---|---|---|---|---|---|---|---|---|---|---|---|---|---|---|
| 96 | ATG | TGT | TGG | AAC | AAA | GGT | TGC | CCA | TGT | GGT | CAG | CGA | TGC | AAC | TTA | CAT | 143 |

| 19 | Arg | Asn | Glu | Cys | Glu | Val | Ile | Ala | Glu | Asn | Ile | Glu | Cys | Gln | Glu | Glu | 34 |
|---|---|---|---|---|---|---|---|---|---|---|---|---|---|---|---|---|---|
| 144 | AGA | AAT | GAA | TGC | GAA | GTA | ATA | GCA | GAG | AAT | ATT | GAA | TGC | CAA | GAG | GAA | 191 |

| 35 | Glu | Cys | Pro | Asp | Pro | Tyr | Leu | Cys | Ser | Pro | Val | Thr | Asn | Arg | Cys | Glu | 50 |
|---|---|---|---|---|---|---|---|---|---|---|---|---|---|---|---|---|---|
| 192 | GAA | TGT | CCT | GAT | CCT | TAC | TTA | TGC | AGT | CCT | GTG | ACC | AAT | CGA | TGT | GAG | 239 |

| 51 | Cys | Thr | Pro | Val | Leu | Cys | Arg | Met | Tyr | Cys | Lys | Phe | Trp | Ala | Lys | Asp | 66 |
|---|---|---|---|---|---|---|---|---|---|---|---|---|---|---|---|---|---|
| 240 | TGC | ACT | CCT | GTA | CTC | TGC | CGA | ATG | TAC | TGC | AAG | TTT | TGG | GCC | AAA | GAC | 287 |

| 67 | Glu | Lys | Gly | Cys | Glu | Ile | Cys | Lys | Cys | Glu | Glu | Leu | Cys | Gln | Asn | Gln | 82 |
|---|---|---|---|---|---|---|---|---|---|---|---|---|---|---|---|---|---|
| 288 | GAA | AAA | GGC | TGC | GAG | ATA | TGT | AAA | TGT | GAA | GAG | CTG | TGC | CAG | AAT | CAA | 335 |

| 83 | Asn | Cys | Thr | Lys | Asp | Met | Leu | Cys | Ser | Ser | Val | Thr | Asn | Arg | Cys | Asp | 98 |
|---|---|---|---|---|---|---|---|---|---|---|---|---|---|---|---|---|---|
| 336 | AAT | TGT | ACC | AAA | GAC | ATG | TTG | TGC | AGC | AGC | GTA | ACT | AAC | AGA | TGT | GAT | 383 |

| 99 | Cys | Gln | Asp | Phe | Lys | Cys | Pro | Gln | Ser | Tyr | Cys | Pro | His | Gly | Phe | Glu | 114 |
|---|---|---|---|---|---|---|---|---|---|---|---|---|---|---|---|---|---|
| 384 | TGT | CAA | GAC | TTC | AAA | TGT | CCA | CAA | TCT | TAC | TGT | CCT | CAC | GGA | TTC | GAA | 431 |

| 115 | Thr | Asp | Glu | Asn | Glu | Cys | Glu | Val | Cys | Ile | Cys | Lys | Lys | Pro | Thr | Cys | 130 |
|---|---|---|---|---|---|---|---|---|---|---|---|---|---|---|---|---|---|
| 432 | ACT | GAT | GAG | AAC | GAA | TGC | GAA | GTT | TGT | ATC | TGC | AAA | AAA | CCA | ACT | TGT | 479 |

| 131 | Ala | Asn | Cys | Gly | Lys | Thr | Thr | Lys | Lys | Pro | Arg | Thr | Ile | Asp | Arg | Leu | 146 |
|---|---|---|---|---|---|---|---|---|---|---|---|---|---|---|---|---|---|
| 480 | GCC | AAC | TGC | GGC | AAA | ACA | ACC | AAG | AAA | CCA | AGA | ACT | ATT | GAC | AGA | CTA | 527 |

| 147 | Lys | Asn | Trp | Phe | Lys | Lys | Lys | Phe | Gly | Lys | *** | Val | Leu | Glu | Thr | Asn | 162 |
|---|---|---|---|---|---|---|---|---|---|---|---|---|---|---|---|---|---|
| 528 | AAA | AAT | TGG | TTC | AAG | AAG | AAA | TTT | GGA | AAA | TAA | GTT | CTT | GAA | ACC | AAC | 575 |

| 163 | Asp | Cys | Arg | Leu | Lys | Leu | Gln | Leu | Thr | His | Tyr | *** | Leu | Ile | Ile | Asp | 178 |
|---|---|---|---|---|---|---|---|---|---|---|---|---|---|---|---|---|---|
| 576 | GAT | TGT | AGA | TTA | AAA | TTA | CAA | TTA | ACA | CAT | TAT | TGA | TTA | ATT | ATT | GAT | 623 |

| 179 | Ala | Phe | Pro | Ser | Pro | Phe | Asp | *** | Glu | Ile | Lys | *** | Asn | Tyr | *** | Ser | 194 |
|---|---|---|---|---|---|---|---|---|---|---|---|---|---|---|---|---|---|
| 624 | GCA | TTT | CCA | TCT | CCA | TTT | GAT | TGA | GAA | ATA | AAA | TAA | AAT | TAC | TAA | AGT | 671 |

| 195 | Gln | Lys | Lys | Lys | Lys | Lys | Thr | Arg |
|---|---|---|---|---|---|---|---|---|
| 672 | CAA | AAA | AAA | AAA | AAA | AAA | ACT | CGA | GG |

POLYPEPTIDE HAVING FACTOR XA INHIBITORY ACTIVITY

This application is a continuation of U.S. Ser. No. 08/225,442, filed Apr. 8, 1994, now abandoned; which is a continuation-in-part of U.S. Ser. No. 08/045,805, filed Apr. 9, 1993, now abandoned.

BACKGROUND OF THE INVENTION

Haemostasis is the interaction of a complex series of processes aimed at ensuring the proper flow of blood through the closed, high-pressure circulatory system which comprises the mammalian vascular system. One aspect of haemostasis is the coagulation cascade which assists in maintaining the integrity of blood vessels following injury. The coagulation cascade is a complex series of processes which culminate in the formation of a fibrin clot at the site of blood vessel injury. Abnormal formation of blood clots is the cause of pathological conditions such as thrombi and embolisms.

The coagulation cascade may be initiated either through the intrinsic pathway, in which all the protein components are present in blood, or through the extrinsic pathway, in which tissue factor, a cell membrane protein, plays a critical role. The last two steps of the coagulation cascade leading to clot formation are common to both pathways. The first of these two steps comprises the formation of the "prothrombinase complex" composed of prothrombin (the zymogen of thrombin), Factor Xa (FXa), and Factor Va on the platelet's membrane surface. Fxa is the enzyme which catalyzes the conversion of prothrombin to thrombin. Thrombin subsequently catalyzes the conversion of fibrinogen to fibrin, an insoluble polymer which is a major component of blood clots.

Treatment with anticoagulants is indicated in a wide range of clinical situations such as thrombosis e.g. deep venous thrombosis (DVT), disseminated intravascular coagulation (DIC), and cardiovascular and cerebrovascular diseases. Other indications include pathophysiological conditions associated with post operative trauma, obesity, pregnancy, side effects of oral contraceptives, prolonged immobilization particularly in the aged, and other known clinical situations involving blood coagulation and thrombosis.

Various references are noted by Arabic numbers in parentheses. These references are listed in numerical order at the end of the specification before the claims and are hereby incorporated by reference in their entirety to further explain the state of the art relevant to this application.

The use of anticoagulants can be beneficial in treatment of both venous thrombosis (14) such as occurs in DVT and DIC, and arterial thrombosis such as occurs during reocclusion following thrombolysis (15). The use of anticoagulants in acute coronary thrombosis is based on the established fact that the coagulation cascade is the primary cause of thrombogenicity also within platelet-rich arterial thrombi (16).

In pathological conditions of excessive clot formation, coagulation can be inhibited either by blocking the catalytic activity of thrombin by heparin—whose action is mediated by the plasmatic inhibitor antithrombin III—or hirudin, or alternatively by inhibiting an earlier step of the coagulation cascade. For example, heparinoids (low molecular weight derivatives of heparin) are known to be selective inhibitors of the step preceding thrombin, i.e., they preferentially enhance the binding of antithrombin III to FXa, thus inhibiting the FXa-catalyzed conversion of prothrombin to thrombin. Since the blood concentration of Factor X is approximately 10-fold lower than that of prothrombin, much smaller amounts of FXa inhibitors than thrombin inhibitors are required to inhibit coagulation. Furthermore, FXa usually resides in the prothrombinase complex and its activity would have to be inhibited in that complex. However, the inhibition by complexes of antithrombin with these heparin derivatives appears to be effective only upon free FXa in the plasma and inefficient when FXa is incorporated in the prothrombinase complex, which is the location of FXa during thrombus formation. This is similar to the disclosure that FXa in a prothrombinase complex is inaccessible to inhibition by the heparin-antithrombin III conjugate (6).

At present, heparin is the most widely used anticoagulant and anti-thrombotic drug, but it has two disadvantages: firstly, it acts at the level of thrombin inhibition, thus necessitating the administration of relatively large amounts of inhibitor; and secondly, it is likely to cause excessive bleeding due to the systemic inhibition of thrombin which is required for normal hemostasis (7). The use of hirudin and its low molecular weight analogs (hirulogs) probably entails similar disadvantages.

These disadvantages prompted the search for new anticoagulant and anti-thrombotic substances suitable for therapeutic use. The use of a selective inhibitor of FXa as an anticoagulant may reduce the problem of bleeding caused by the currently used anti-thrombotic drugs, such as heparin and hirudin and their analogs. This postulated advantage is due to the fact that a FXa inhibitor acts as a modulator of coagulation since it does not affect already existing thrombin and therefore does not completely neutralize normal hemostasis. This is because the existing thrombin is entrapped in active form in fibrin clots and is released during thrombolysis (17).

Two closely related factor Xa inhibitors have been isolated from the Mexican leech *Haementeria officinalis* (antistasin— references 1 and 2) and from the giant Amazonian leech *Haementeria ghiliani* (3, 4).

A third FXa inhibitor—termed tick anti-coagulant peptide (TAP) isolated from the tick *Ornithodorous moubata* (5,9) has been cloned, expressed, purified and characterized (10). A fourth potent FXa inhibitor, isolated from the black fly, *Simulium vittatum,* has also been characterized (11).

Both in vitro and in vivo studies have shown that inhibition of FXa-mediated coagulation with two of these inhibitors, antistasin and TAP, is as effective as heparin in preventing venous thrombosis (12).

Additionally, Rigbi et al. (13) disclose a factor Xa inhibitor isolated from the saliva of the European leech *Hirudo medicinalis.*

This application discloses the surprising and unexpected discovery of a novel Factor Xa inhibitor ("FXaI") having a sequence different from that of any known FXa inhibitor.

SUMMARY OF THE INVENTION

"FXaI" as used herein refers to a novel polypeptide having FXa inhibitory activity which is present in the European leech *Hirudo medicinalis* and has a sequence different from that of any known FXa inhibitor. "Recombinant FXaI", "recFXaI", and "rFXaI" all refer to the novel polypeptide having FXa inhibitory activity expressed by recombinant DNA; the term "FXaI" is also often used to refer to recombinant FXaI where no possibility of ambiguity exists.

The present invention provides a polypeptide comprising the amino acid sequence

| | | | | | | | | | | | | | |
|---|---|---|---|---|---|---|---|---|---|---|---|---|---|
| X— | Y— | CYS | GLN | GLU | GLU | GLU | CYS | PRO | ASP | PRO | TYR | LEU | CYS |
| SER | PRO | VAL | THR | ASN | ARG | CYS | GLU | CYS | THR | PRO | VAL | LEU | CYS |
| ARG | MET | TYR | CYS | LYS | PHE | TRP | ALA | LYS | ASP | GLU | LYS | GLY | CYS |
| GLU | ILE | CYS | LYS | CYS | GLU | GLU | LEU | CYS | GLN | ASN | GLN | ASN | CYS |
| THR | LYS | ASP | MET | LEU | CYS | SER | SER | VAL | THR | ASN | ARG | CYS | ASP |
| CYS | GLN | ASP | PHE | LYS | CYS | PRO | GLN | SER | TYR | CYS | — | Z (SEQ. ID NO. 1) | | wherein X is MET or absent;

Y is 0–29 amino acids of the sequence LYS MET CYS TRP ASN LYS GLY CYS PRO CYS GLY GLN ARG CYS ASN LEU HIS ARG ASN GLU CYS GLU VAL ILE ALA GLU ASN ILE GLU(SEQ ID NO:2), with the proviso that if part of the sequence is present, it is the carboxy terminal part of the sequence and wherein $Val^{24}$ may be preceded by Gly;

Z is absent or is all or a part of the sequence $Pro^{110}$-$Lys^{156}$ shown in FIG. 7, with the proviso that if part of the sequence is present, it is the amino terminal part of the sequence.

Also provided by the present invention is a method of producing the polypeptide in bacteria, and a method of recovering the polypeptide produced in bacteria.

In additional aspects, the present invention provides uses of the polypeptide in therapeutic and diagnostic methods applied in situations or conditions characterized by the occurrence of excessive blood coagulation and thrombosis.

In an additional aspect, the present invention provides an antibody to the polypeptide.

This figure summarizes two different protocols used to purify a FXa inhibitor from DLS for amino acid sequencing, as well as various experiments performed in order to corroborate the identity and homogeneity of the resulting preparations. In Run II, Mono-Q was used instead of Q-Sepharose.

Figure 2:
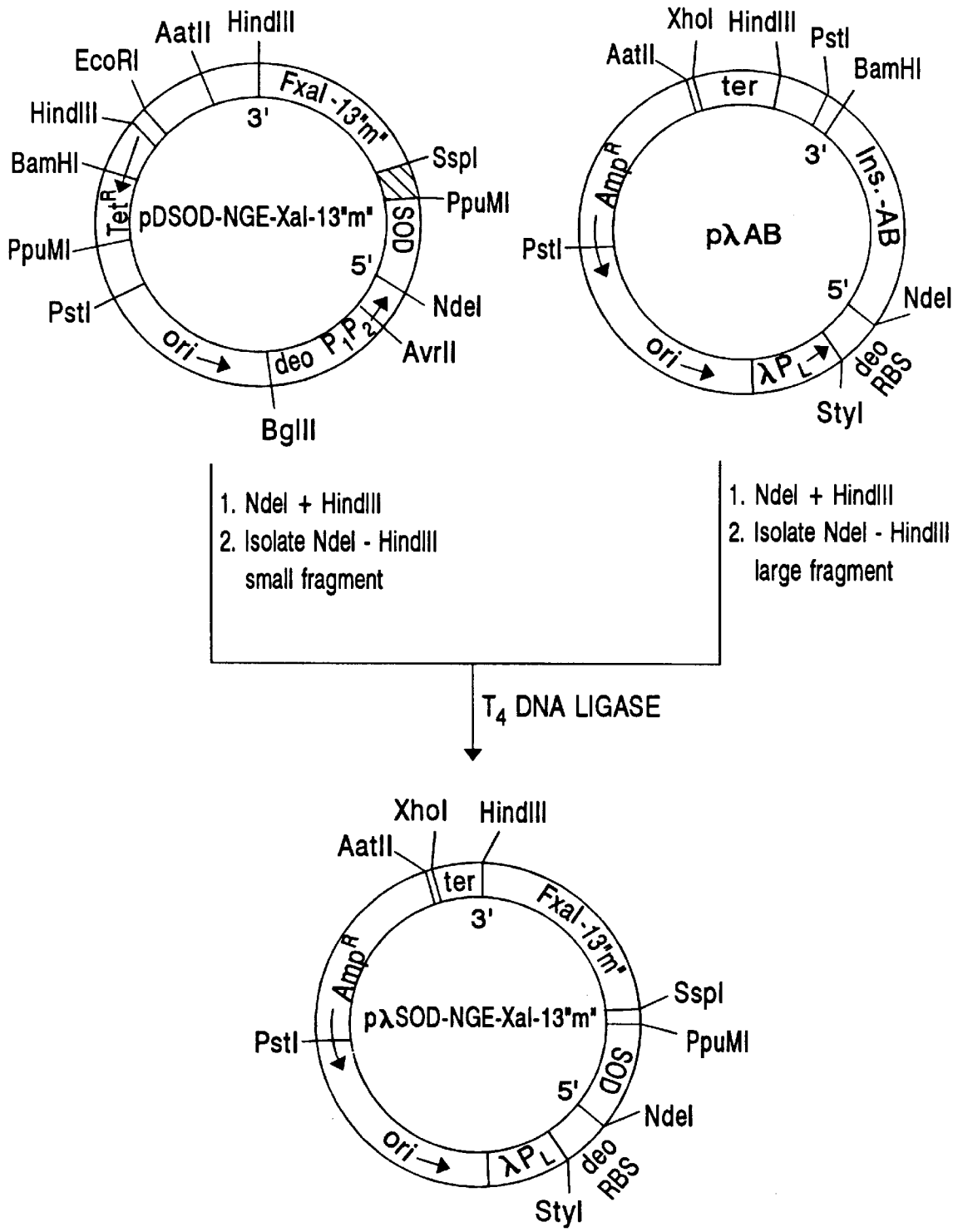

FIG. 2: Construction of Plasmid pλSOD-NGE-XaI-13"m"

The construction of plasmid pλSOD-NGE-XaI-13"m" as described in Example 10 is shown. Plasmid pλSOD-NGE-XaI-13"m" expresses a fusion protein containing 63 amino acids of a modified Cu/Zn-SOD sequence and the FXaI 13"m"polypeptide having the sequence $glu^{23}$-$lys^{156}$ shown in FIG. 7 under control of the $\lambda P_L$ promoter. The 13"m" polypeptide may be obtained by hydroxylamine cleavage at the engineered cleavage site between the SOD moiety and the FXaI moiety. Plasmid pλSOD-NGE-XaI-13"m" has been deposited in the ATCC in E. coli 4300 under Accession No. 69269.

FIG. 3: Amino Acid Sequence Comparison of FXa Inhibitor Isolates and Antistasin

This figure compares the amino acid sequences of naturally occurring FXa inhibitor as represented by clone PCR4, cDNA clones and antistasin. The sequences were aligned by the alignment program Pileup, based on: "Simplification of Progressive Alignment Method", Feng & Doolittle, J. Mol. Evol. 35:351–360 (1987).

PCR4 is the sequence of the PCR derived DNA sequence encoding a FXa inhibitor present in DLS and represents the sequence of the naturally occurring FXa inhibitor. (Methionine in the fourth position is apparently an error of the PCR reaction which explains why it differs from isoleucine in the fourth position of the N-terminal amino acid sequence obtained for the naturally occurring inhibitor isolated from leech saliva). PCR4 was obtained as described in Example 3 by hybridization of PCR-derived clones with the nucleotide sequence encoding the first 9 amino acids of naturally occurring FXa inhibitor isolated from leech saliva. 13 represents the sequence of clone 13 from a cDNA library, and includes a putative extension peptide (see Example 4). AS represents the sequence of antistasin. "<E" represents pyroglutamate. The numbering is according to the sequence of PCR4. Gaps have been introduced to obtain the best alignment. The cysteine residues which have been aligned are highlighted.

Figure 4:
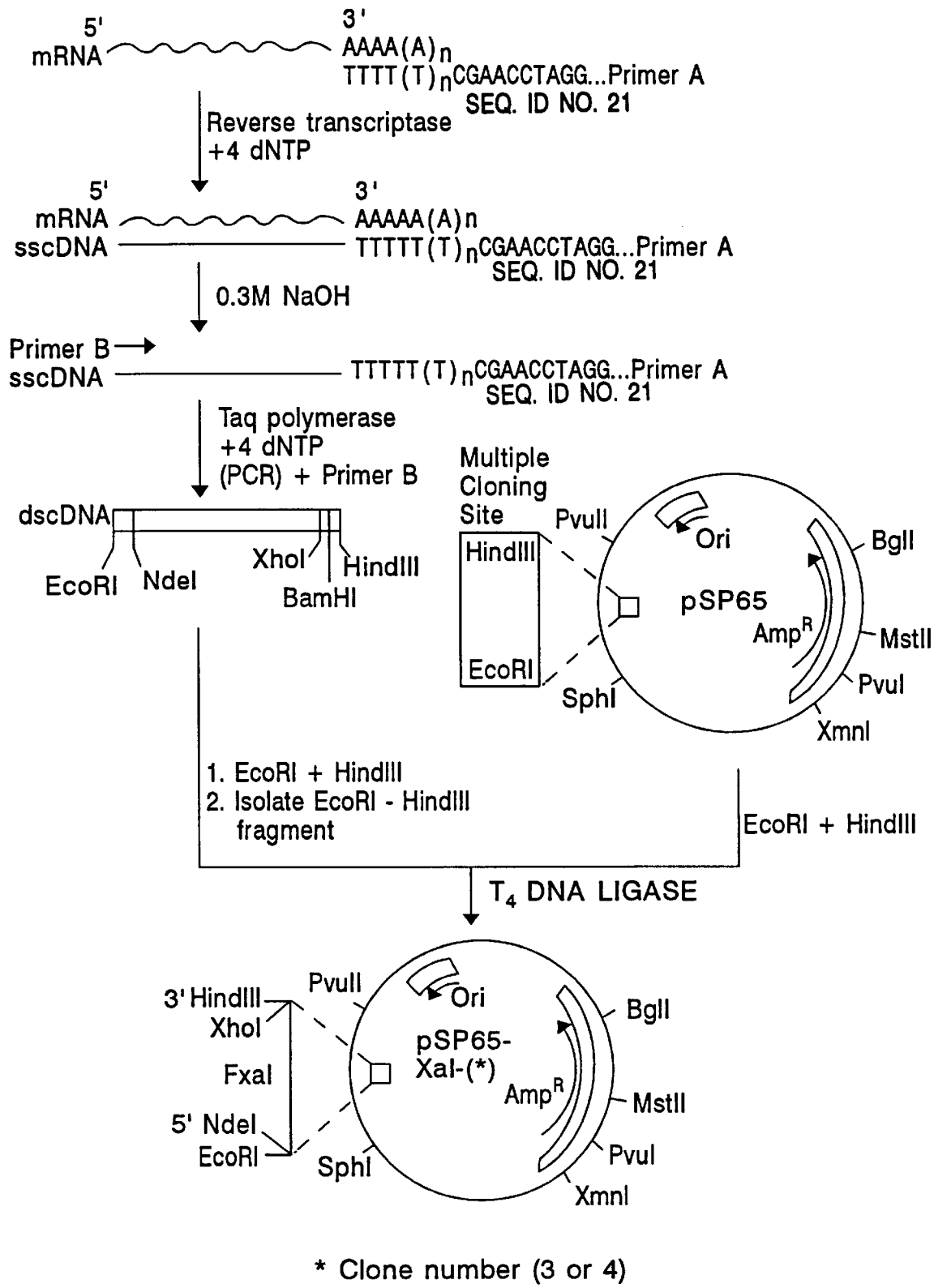

FIG. 4: Cloning of FXa Inhibitor cDNA by PCR

As described in Example 3, poly $A^+$ mRNA was isolated from total RNA extracted from 120 leeches. An aliquot of the poly$^+$ mRNA so obtained (5 µg) was used as template in a reverse transcription reaction in the presence of the synthetic primer A

A: 5'- AACTCGAGGATCCAAGCTTTTTTTTTTTTTT -3'
(SEQ. ID NO. 3)

and 4 dNTPs. Following the synthesis of single stranded complementary DNA (ss-cDNA), the mRNA was degraded by overnight alkali treatment comprising 0.3M NaOH at room temperature. The neutralized ss-cDNA was subjected to PCR amplification using Taq polymerase, 4 dNTPs and the synthetic degenerative DNA oligomer B

```
                            T   A           T      T  T
B: 5'- CCGAATTCATATGTA  GA  GTIATITA  GTIGA  GA  CC-3'
                        C   G            C      C  C
                                        (SEQ. ID NO. 4)
``` as reverse primer.

The PCR amplification products were digested with EcoRI and HindIII. The gel purified fragments were then subcloned into the large EcoRI-HindIII fragment of plasmid pSP65. The ligation mixture was used to transform E. coli MC1061. The resulting transformants were screened by in-situ hybridization using the radiolabeled synthetic probe C (disclosed in Example 3) corresponding to N-terminal amino acids 14 to 19 of the purified leech derived FXa inhibitor.

FIG. 5: DNA and Deduced Amino Acid Sequence of Clone pSP65-XaI-4

Plasmid DNA was prepared from positive clones identified by in-situ hybridization with the radiolabeled probe C. The purified plasmid DNA of clone pSP65-XaI-4 was sequenced by the Sanger dideoxy method. The resulting sequence was processed using LKB 2020 DNASIS software system.

Figure 6:
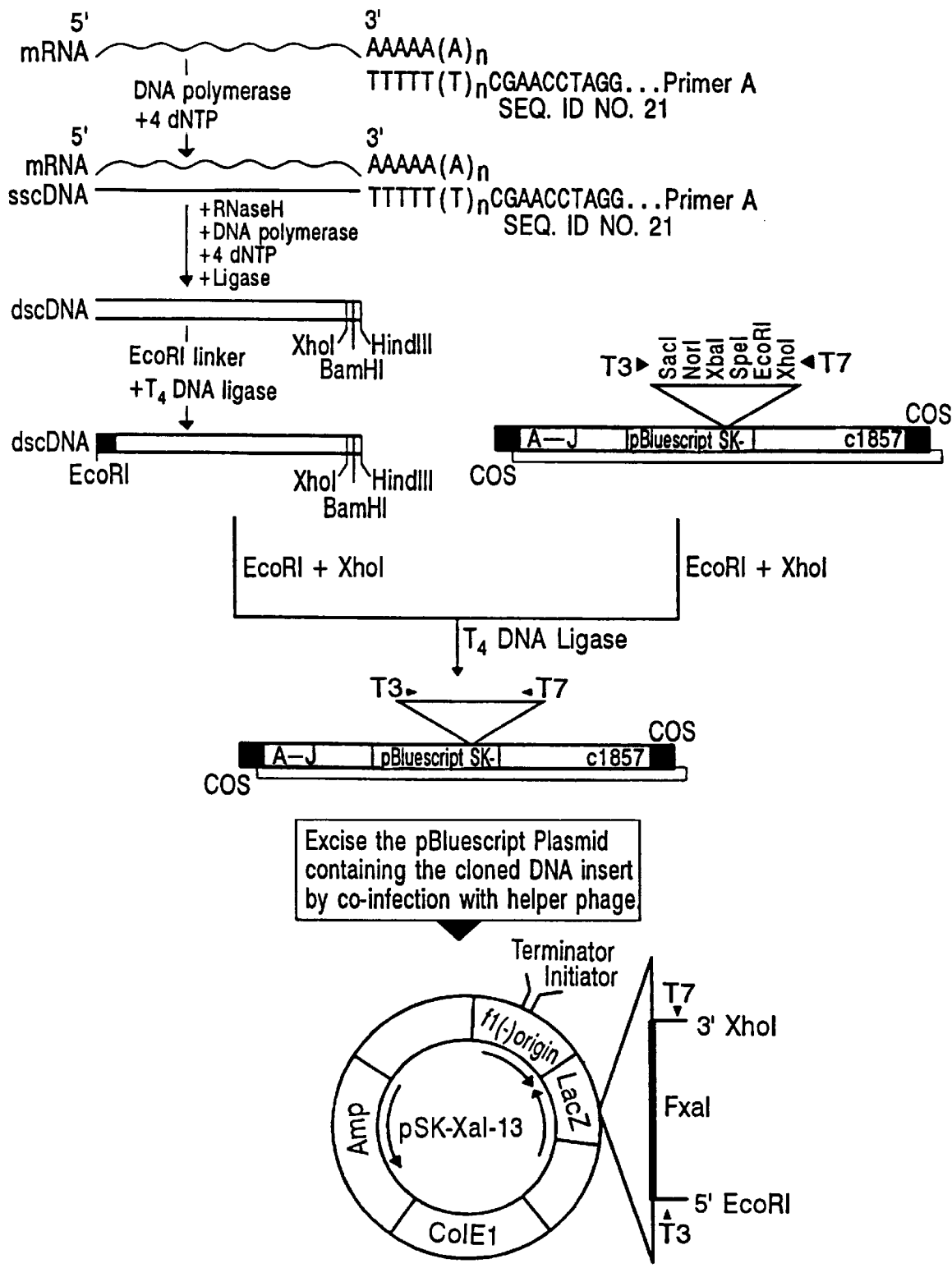

FIG. 6: Cloning of FXa Inhibitor cDNA from a cDNA Library

As described in Example 4, poly $A^+$ mRNA obtained from total RNA extracted from 120 leeches was used for double stranded complementary DNA (ds-cDNA) synthesis using the Stratagene ZAP™ cDNA synthesis kit. The ds-cDNA so obtained was digested with XhoI and EcoRI and subcloned into the XhoI-EcoRI digested Uni-ZAP vector designated pBluescript SK. The cDNA library obtained was screened for clones encoding FXa inhibitor, using radiolabeled DNA of plasmid pSP65-XaI-4 as a probe, under hybridization conditions of high and low stringency. The prehybridization of the filters was carried out for 8 hours at 60° C. in 6×SSC (1×SSC: 0.15M NaCl, 0.015M Na-citrate), 0.1% SDS, 5×Denhardt (0.1% Ficoll 400, 0.1% polyvinyl pyrrolidone, 0.1% BSA, 0.5% SDS) and 100µg/ml salmon sperm DNA, followed by hybridization with the radioactive probe for 48 hours at 60° C. Following hybridization, the filters were washed at two different conditions: to obtain high stringency conditions, filters were washed with 0.2–0.5×SSC containing 0.2% SDS at 65° C. for two hours with several changes of solution; to obtain low stringency conditions, filters were washed with 2×SSC containing 0.2% SDS at 60° C. for two hours with several changes of solution. The plasmid of one of the clones, obtained at low stringency, was designated pSK-XaI-13.

FIG. 7: DNA and Deduced Amino Acid Sequence of cDNA Clone pSP65-XaI-13

The construction of plasmid pSP65-XaI-13 containing DNA encoding FXaI obtained from plasmid pSK-XaI-13 is described in Example 6. Purified DNA of plasmid pSP65-XaI-13 was sequenced by the Sanger dideoxy method. The data obtained was processed using the LKB 2020 DNASIS software system.

Figure 8:
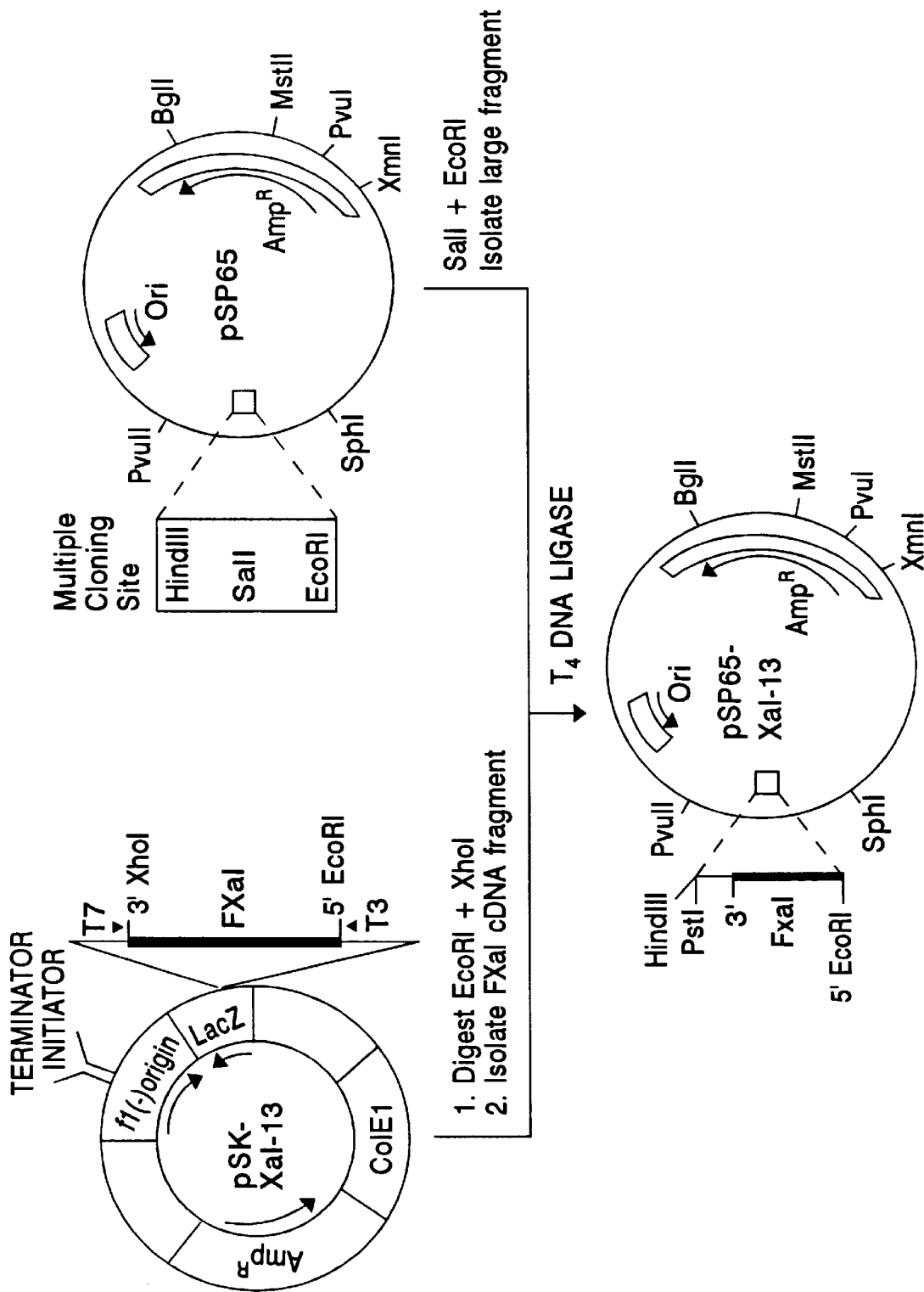

FIG. 8: Subcloning of cDNA encoding recombinant FXaI

This figure shows the construction of plasmid pSP65-XaI-13 containing DNA encoding FXaI obtained from plasmid pSK-XaI-13 as described in Example 6. Plasmid pSK-XaI-13 was digested with XhoI and EcoRI. The XhoI-EcoRI fragment containing the FXaI coding region was isolated and subcloned into SalI-EcoRI digested plasmid pSP65. The resulting plasmid was designated pSP65-XaI-13.

Figure 9:
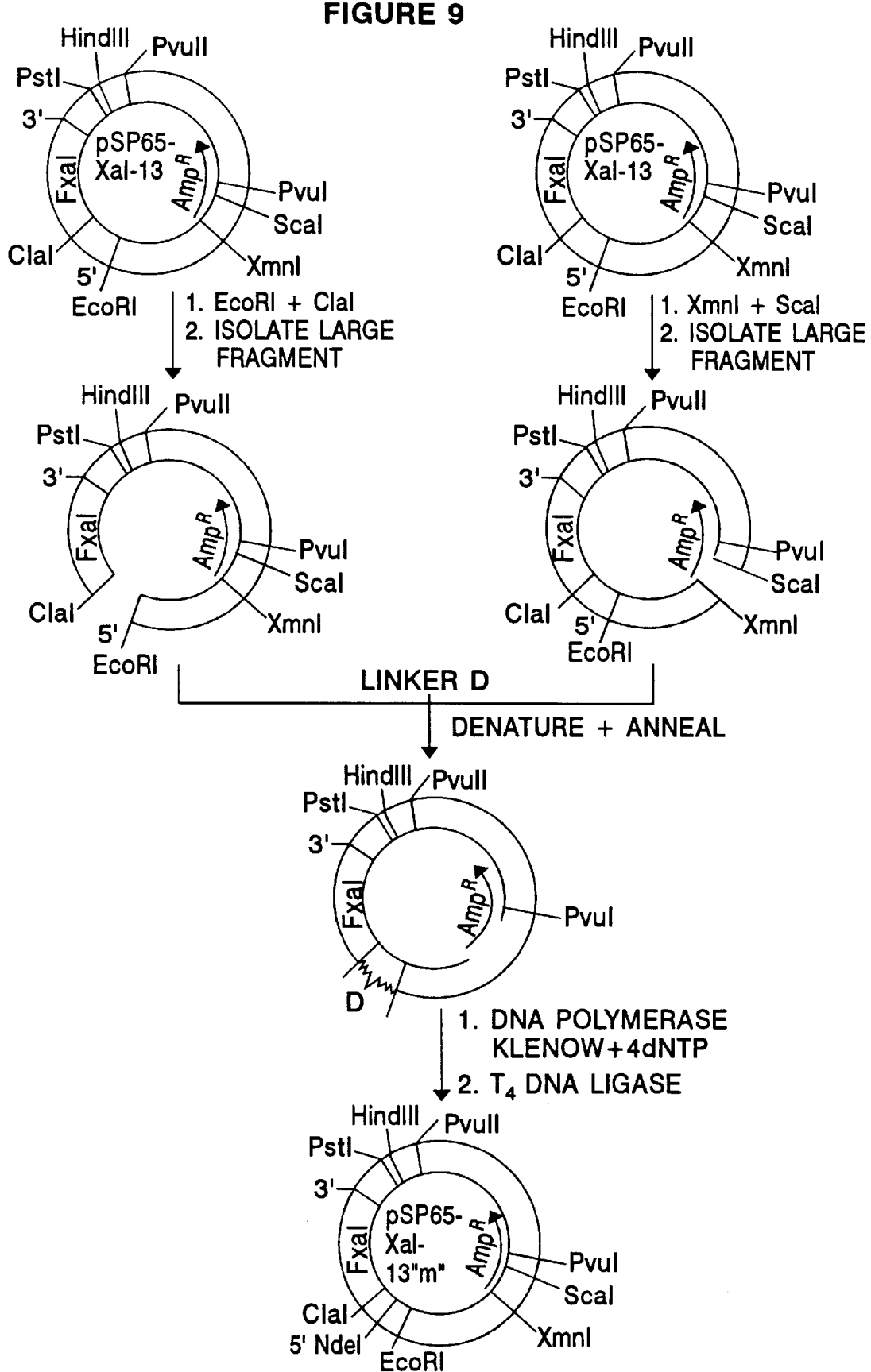

FIG. 9: Construction of Plasmid pSP65-XaI-13"m"

Plasmid pSP65-XaI-13 does not contain an ATG initiation codon at the predicted N-terminus of the mature protein. This figure shows the introduction into plasmid pSP65-XaI-13 of an ATG initiation codon adjacent to amino acid Val$^{24}$ by site-directed mutagenesis. Plasmid pSP65-XaI-13 was digested with EcoRI and ClaI which cleaves within the FXaI coding region. A second aliquot of plasmid pSP65-XaI-13 was digested with XmnI and ScaI which cleaves within the Amp$^R$ coding region. From both aliquots, the large DNA fragment was isolated, denatured and annealed in the presence of synthetic oligomer D:

NdeI
D: 5'- GAATTGCGAAGCATATGGTAATAGCAG -3'(SEQ. ID NO. 5)

thus introducing the initiation codon ATG . A DNA polymerase (Klenow) reaction was then carried out in the presence of 4 dNTPs followed by ligation with T$_4$ DNA ligase. A clone both ampicillin resistant and positive in hybridization with oligomer D was designated pSP65-XaI-13"m".

Figure 10:
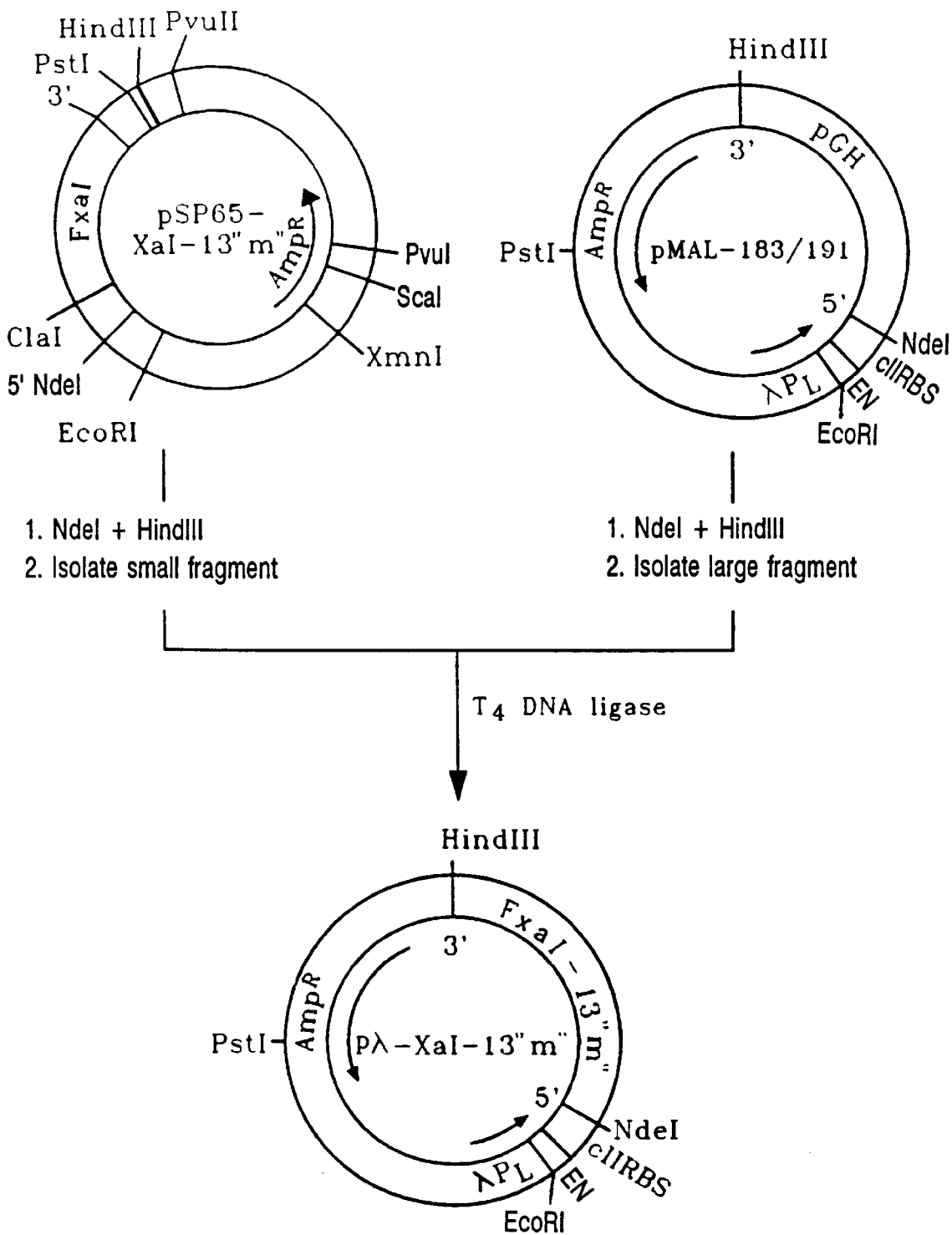

FIG. 10: Construction of Expression Plasmid pλ-XaI-13"m"

This figure shows the construction of a plasmid for the expression of a mature ("m") FXaI polypeptide encoded by clone pSP65-XaI-13"m" under control of the XPL promoter. Plasmid pSP65-XaI-13"m" was digested with NdeI and HindIII. The NdeI-HindIII DNA fragment coding for the FXaI polypeptide was isolated and ligated to the large fragment isolated following NdeI-HindIII digestion of plasmid pMAL-183/191 containing the λP$_L$ promoter and the λcII ribosomal binding site (RBS). The ligation mixture was used to transform *E. coli* 4300. The resulting plasmid which expresses FXaI was designated pλ-XaI-13"m" and deposited under ATCC Accession No. 69135.

Figure 11:
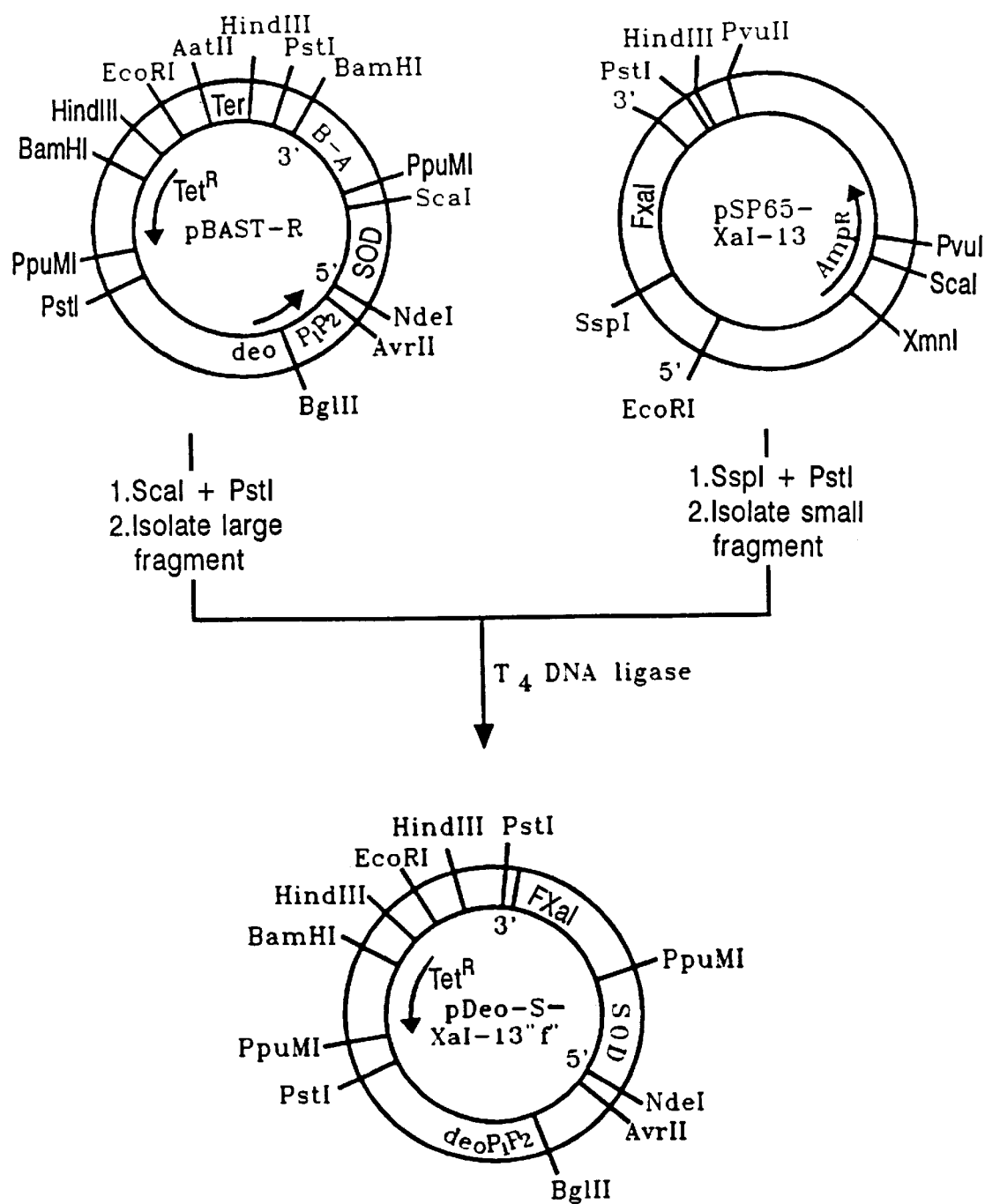

FIG. 11: Construction of Plasmid pDeo-S-XaI-13"f" for Expression of an SOD-FXaI Fusion Protein This figure shows the construction of a plasmid under control of the deo P$_1$P$_2$ promoters for expression of the recombinant FXaI polypeptide produced by clone 13, fused to a polypeptide fragment containing 58 amino acids from a modified Cu/Zn-SOD sequence. Plasmid pSP65-XaI-13 was digested with SspI and PstI. The SspI-PstI DNA fragment encoding FXaI was isolated and ligated to the large ScaI-PstI fragment of plasmid pBAST-R. The resulting plasmid was designated pDeo-S-XaI-13"f" and deposited in the ATCC under Accession No. 69137.

Figure 12:
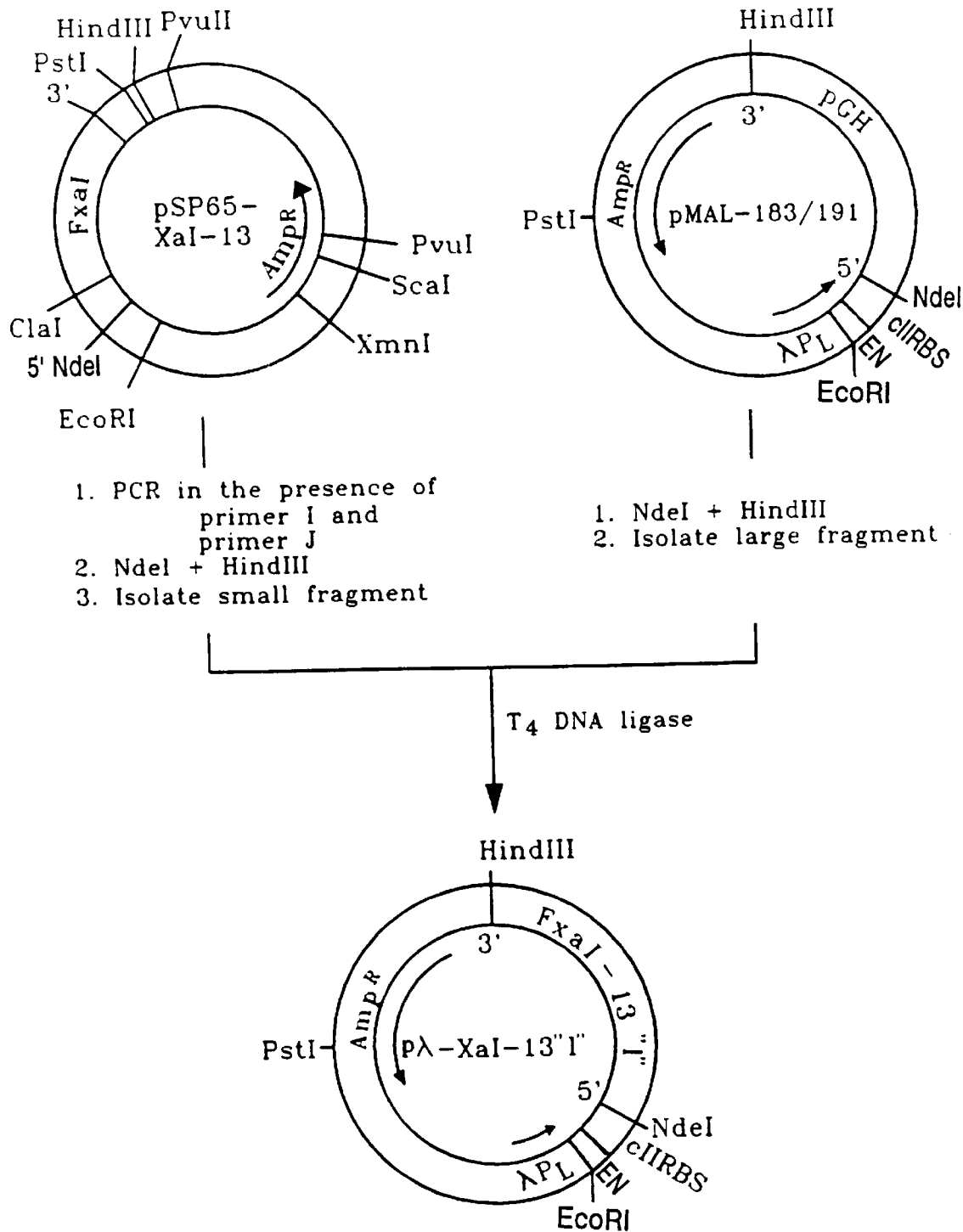

FIG. 12: Construction of Plasmid pλ-XaI-13"l" for Expression of an FXaI Prepeptide (FXaI sequence preceded by an extension peptide)

This figure shows the construction of a plasmid under control of λPL for expression of a "prepeptide" of FXaI. Plasmid pSP65-XaI-13 was modified by introduction of an NdeI site at met$^3$ by site-directed mutagenesis utilizing the PCR technique. DNA of plasmid pSP65-XaI-13 was PCR amplified in the presence of the 5' synthetic primer:

I: 5'- CCGAATTCATATGTGTTGGAACAAAGGT -3'(SEQ. ID NO. 6)

and the synthetic oligomer:

J: 5'- CCAAGCTTGGGCTGCAGGTCGA -3'(SEQ. ID NO. 7)

The product was digested with NdeI and HindIII. The small NdeI-HindIII fragment was then ligated to the large NdeI-HindIII fragment of plasmid pMAL-183/191 containing the λP$_L$ promoter and the λcII RBS. The resulting plasmid was designated pλ-XaI-13"l".

Figure 13:
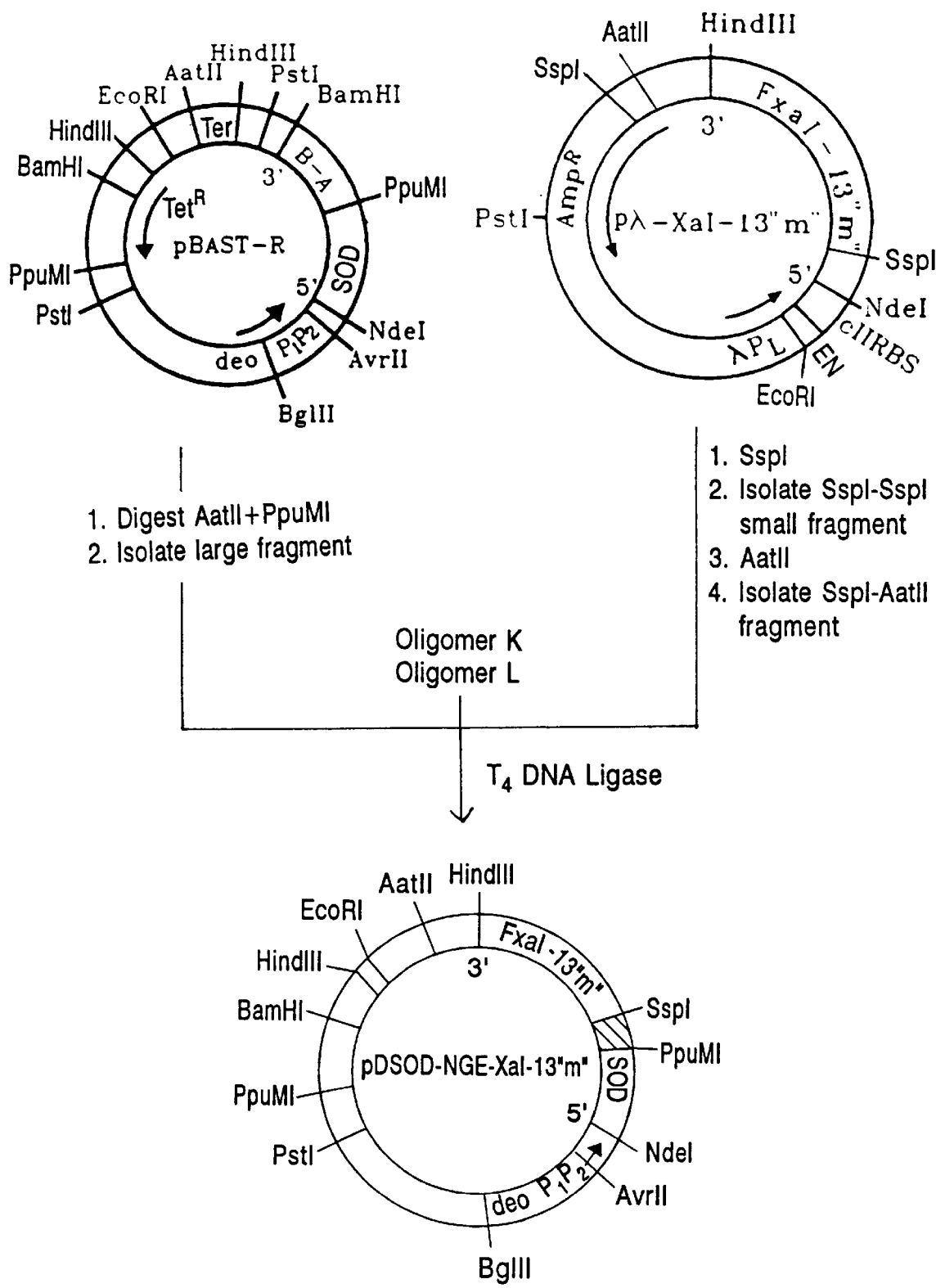

FIG. 13: Construction of Plasmid DDSOD-NGE-XaI-13"m"

The construction of plasmid pDSOD-NGE-XaI-13"m" as described in Example 10 is shown. Plasmid pDSOD-NGE-XaI-13"m" expresses a fusion protein containing 63 amino acids of a modified Cu/Zn-SOD sequence and the FXaI 13"m"polypeptide having the sequence glu$^{23}$-lys$^{156}$ shown in FIG. 7 under control of the deo promoter. The 13"m" polypeptide may be obtained by hydroxylamine cleavage at the engineered cleavage site between the SOD moiety and the FXaI moiety.

Oligomer K and oligomer L have the following sequences:

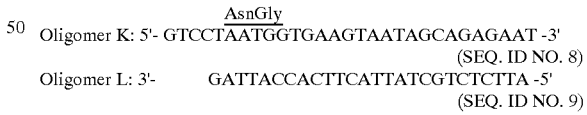

Figure 14:
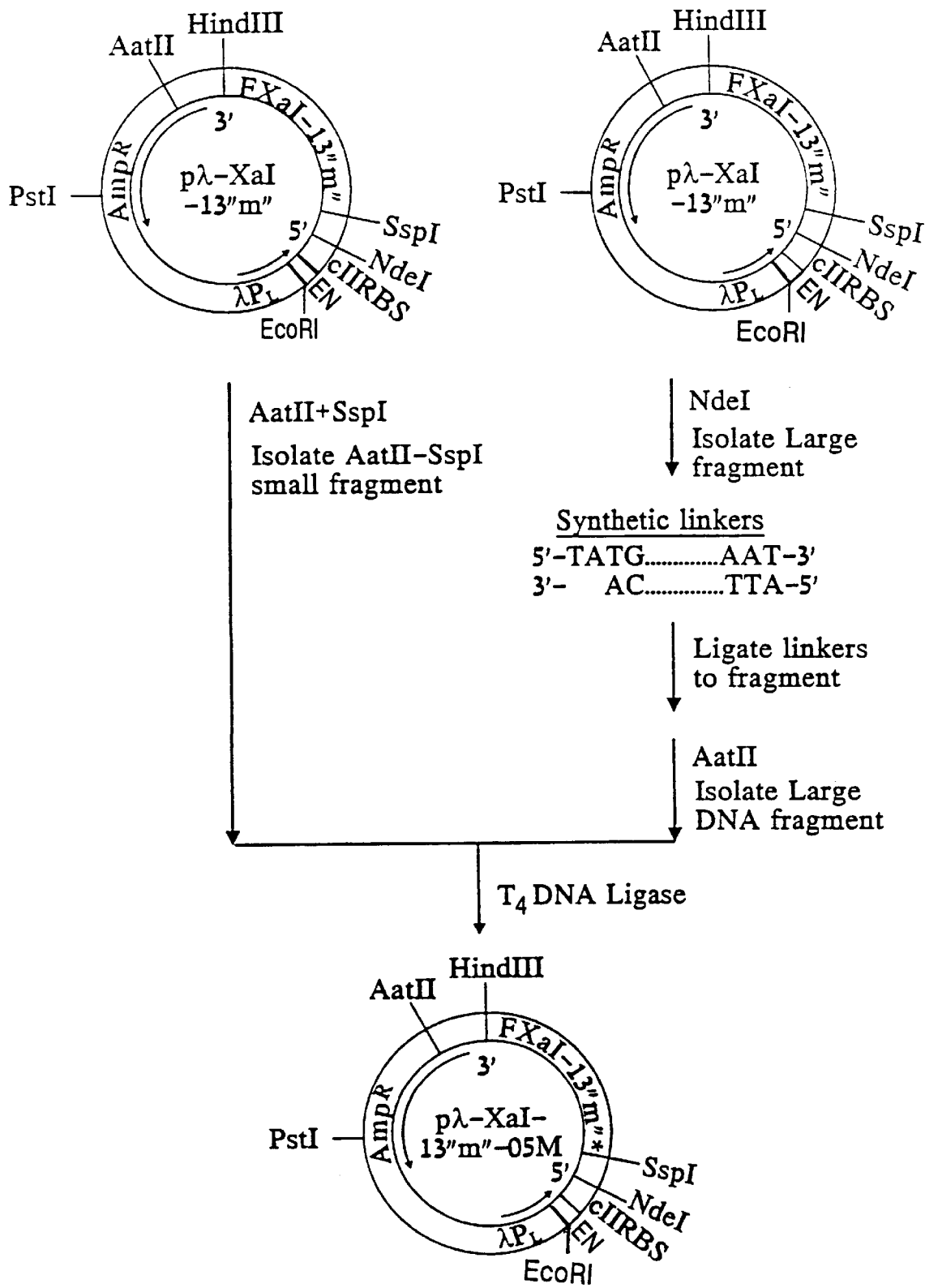

FIG. 14: Construction of expression plasmid pλ-XaI-13"m"-05M

Plasmid pλ-XaI-13"m" (ATCC Accession No. 69135) was digested with NdeI endonuclease. The linear form, large DNA fragment was isolated and ligated in the presence of T$_4$ DNA ligase to a synthetic DNA fragment having the following sequence:

After overnight ligation at 14° C., the ligation mixture was digested with AatII endonuclease and the large DNA fragment was isolated. This DNA fragment was ligated to a AatII-SspI small fragment derived from another aliquot of plasmid pλ-XaI-13"m" previously digested with AatII and SspI endonucleases. The newly obtained plasmid was designated pλ-XaI-13"m"-05M.

Figure 15:
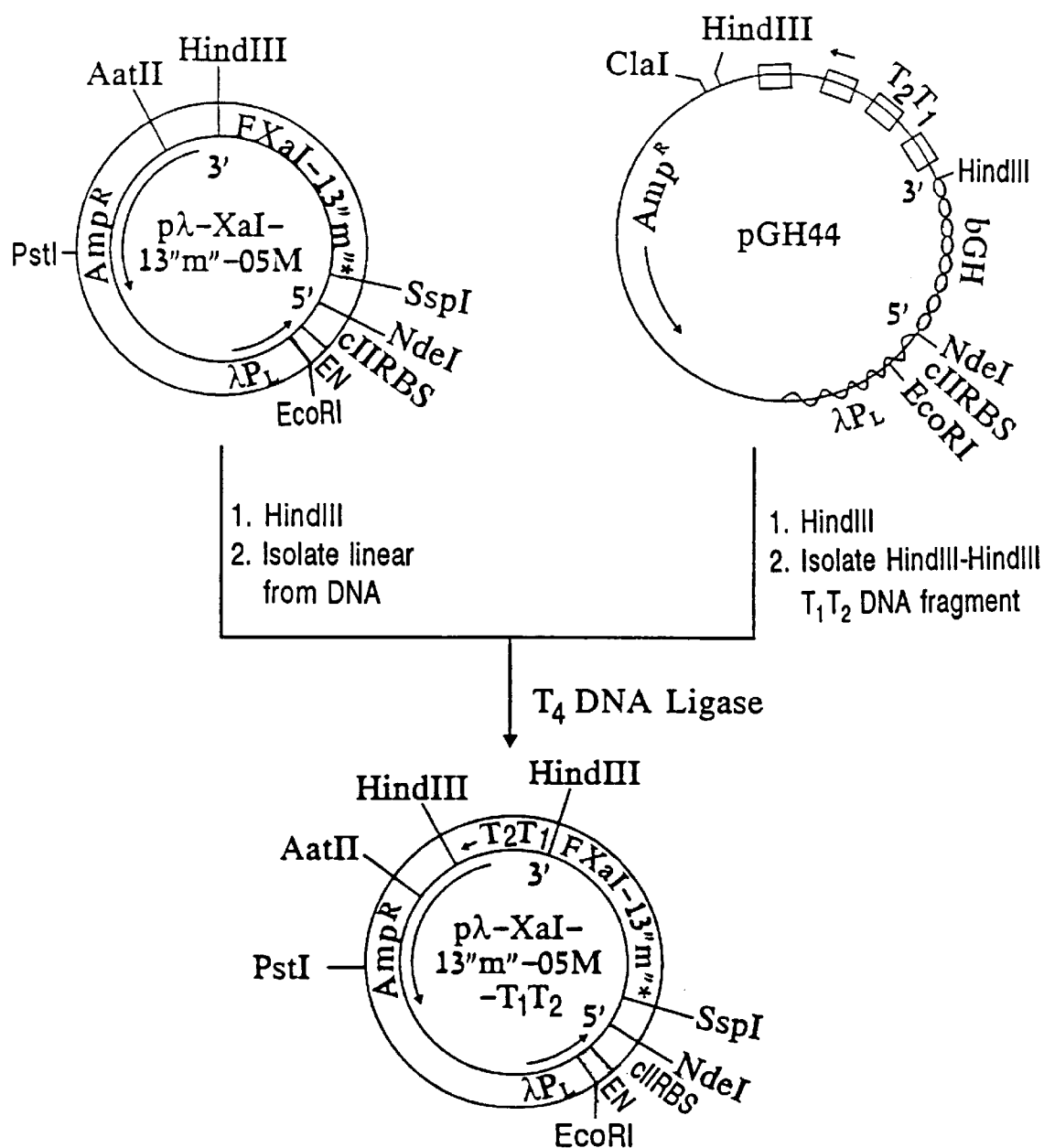

FIG. 15: Construction of expression plasmid pλ-XaI-13"m"-05M-$T_1T_2$

Plasmid pλ-XaI-13"m"-05M was digested with HindIII endonuclease and the linear DNA was isolated and ligated to the small HindIII-HindIII $T_1T_2$ DNA fragment obtained by HindIII endonuclease digestion of DNA plasmid pHG44 (deposited under ATCC Accession No. 39806 on Aug. 20, 1984). The newly obtained plasmid was designated pλ-XaI-13"m"-05M-$T_1T_2$.

Figure 16:
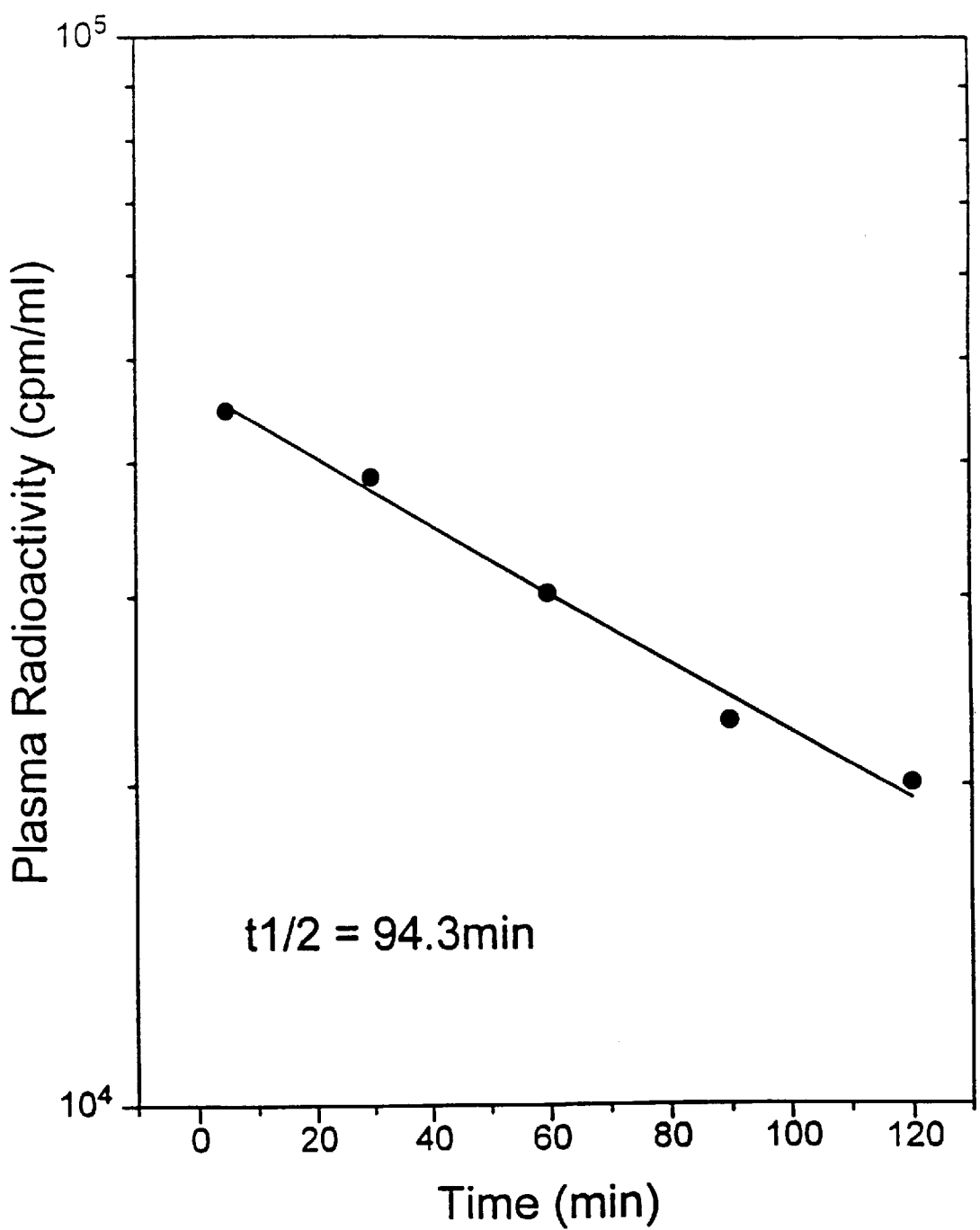

FIG. 16: Pharmacokinetics of FXaI in the rabbit

FXaI was radio-iodinated ($^{125}$I), admixed with unlabeled material (specific activity $0.13 \times 10^6$ cpm/μg) and injected in a rabbit (10 μg/rabbit). Analysis of plasma samples at the indicated time intervals over a two hour period revealed that the labeled material was fully TCA precipitable at all times and its level declined with a half-life of about 94 minutes.

Figure 17:
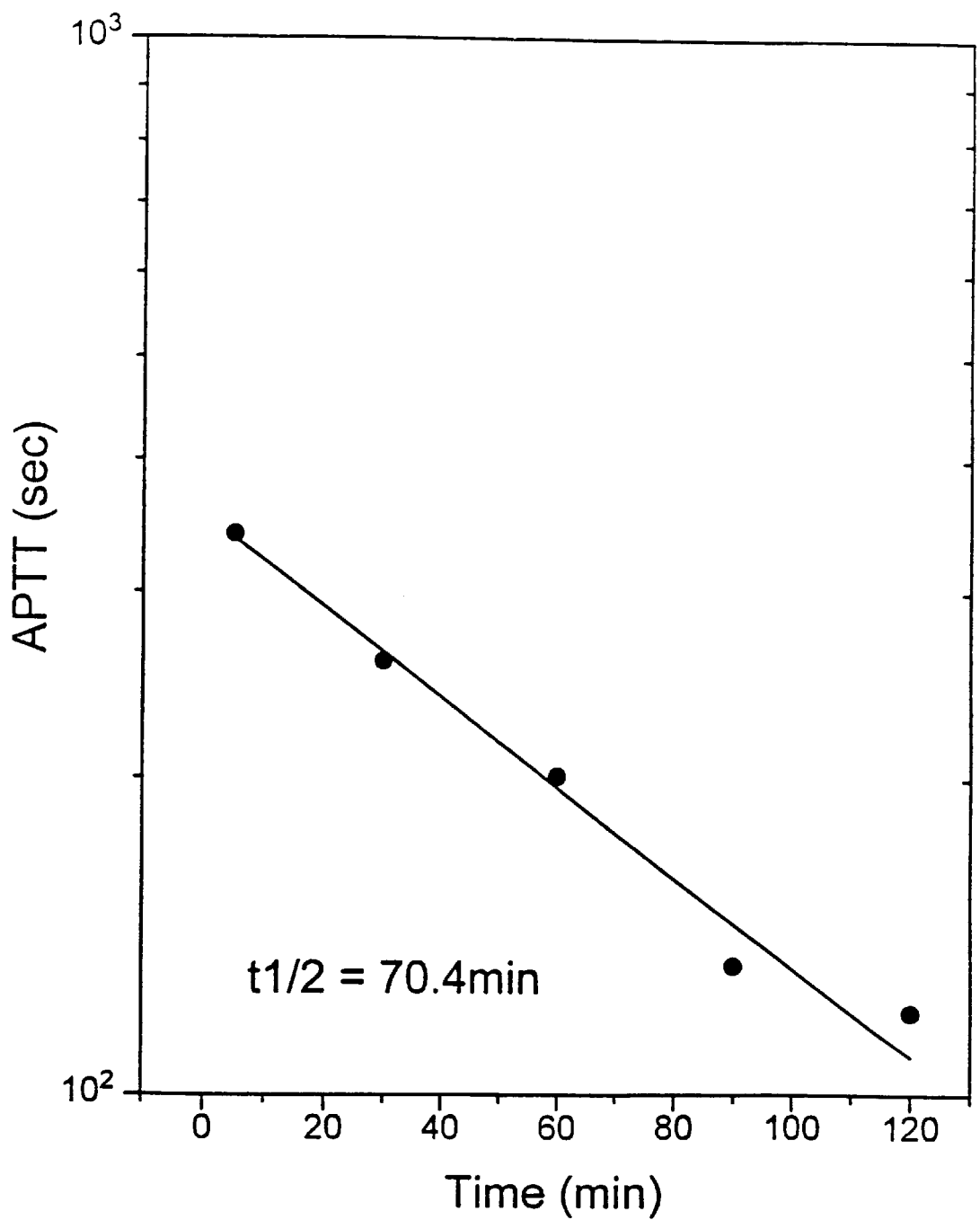

FIG. 17: Pharmacodynamics of FXaI in the rabbit

Ex vivo APTT dose responses were measured at the indicated time intervals over a two hour period and revealed that in the rabbit the half-life value of FXaI in the plasma was about 70–78 minutes.

Figure 18:
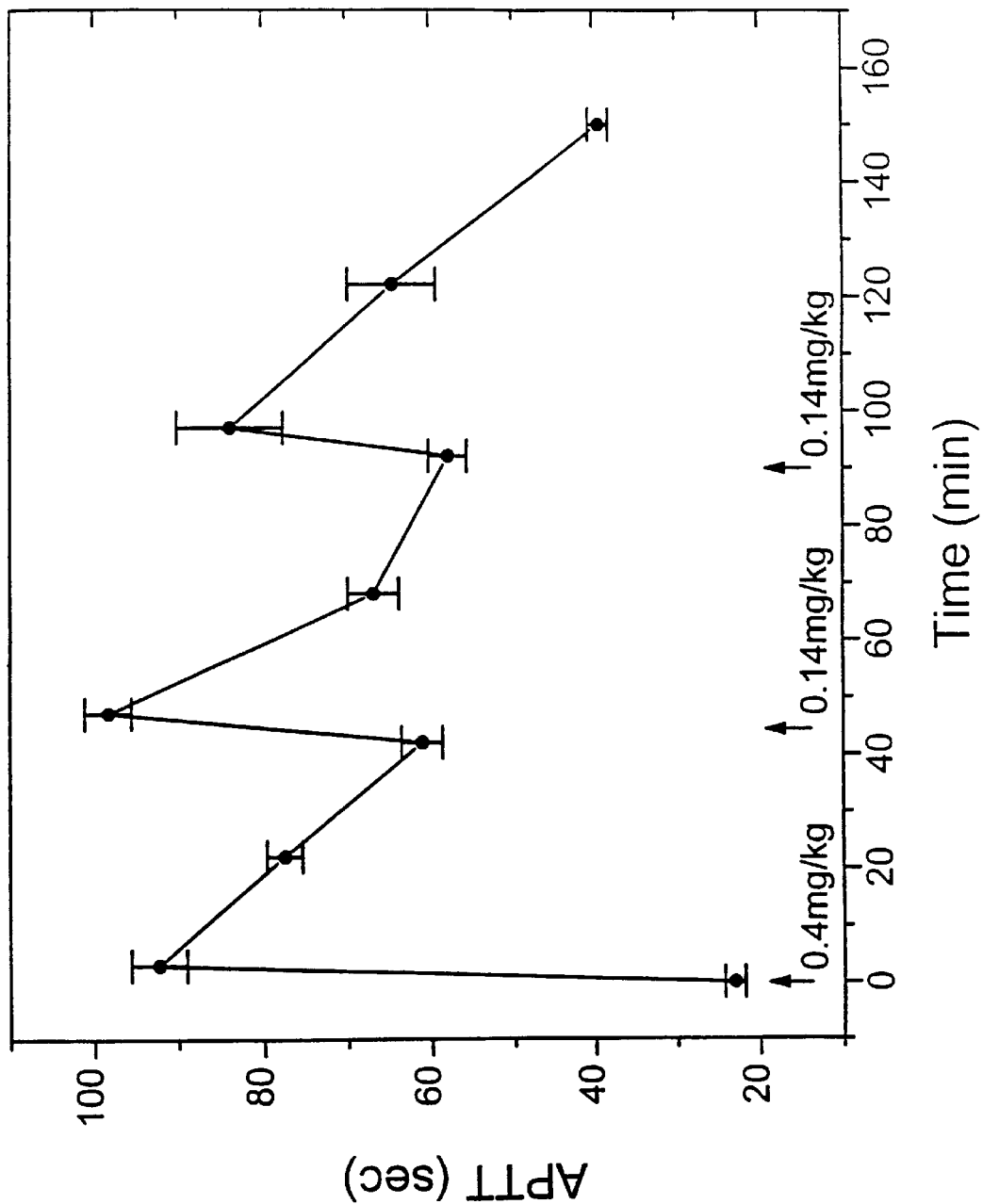

FIG. 18: Three-injection regimen of FXaI for the Rat Coil Model

In order to attain a continuous plasma level of FXaI, plasma levels of FXaI were estimated by ex vivo APTT measurements which revealed that satisfactory plasma profiles (about 20% fluctuations) of FXaI were obtained by an initial i.v. dose at zero-time, followed by two doses of 35% of the initial dose at 45 min intervals.

Figure 19:
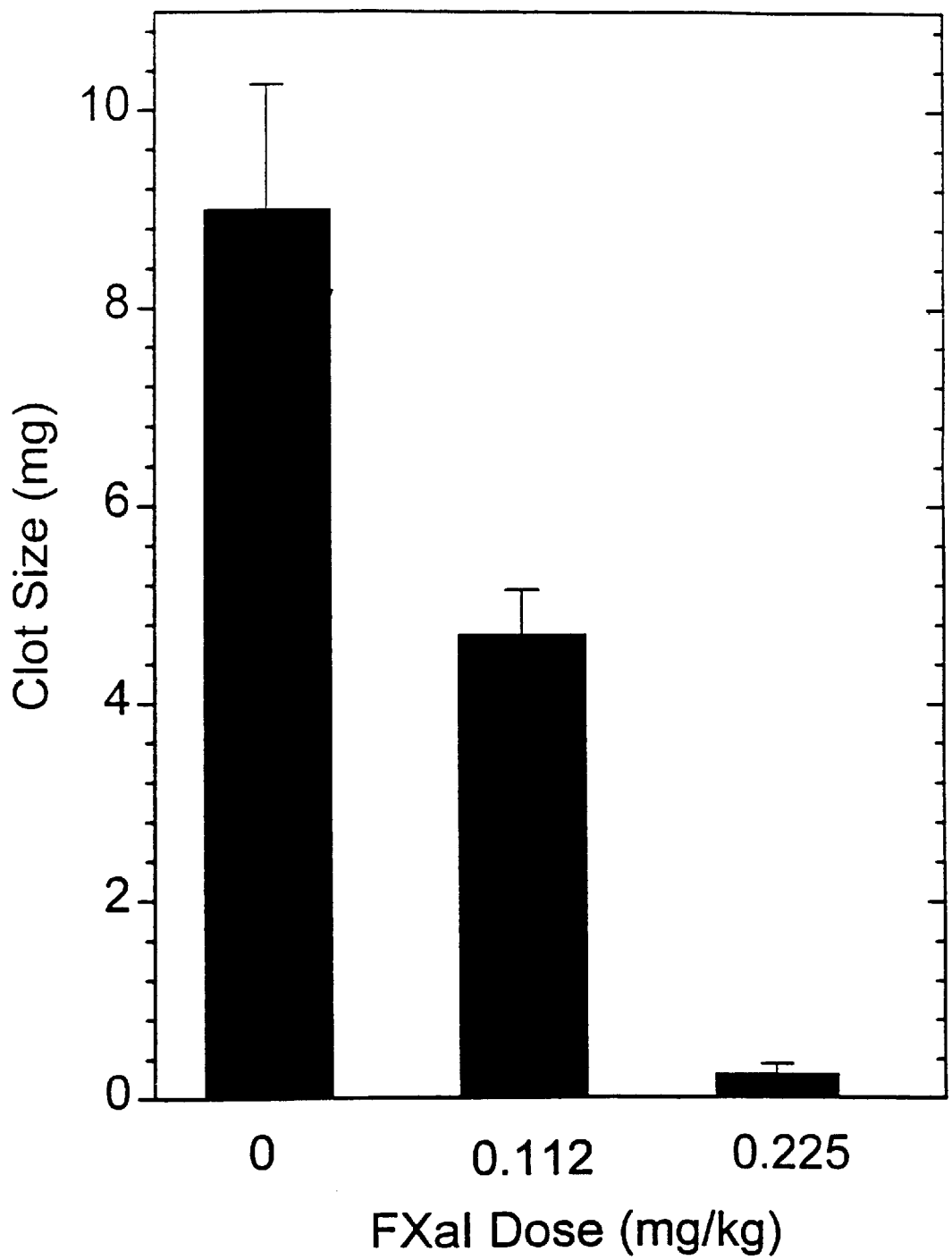

FIG. 19: The effect of FXaI on clot formation in the rat coil model

The weight of the clot formed on the steel coils was determined in the rat coil model (as described in Example 15) with three doses of FXaI as indicated.

Figure 20:
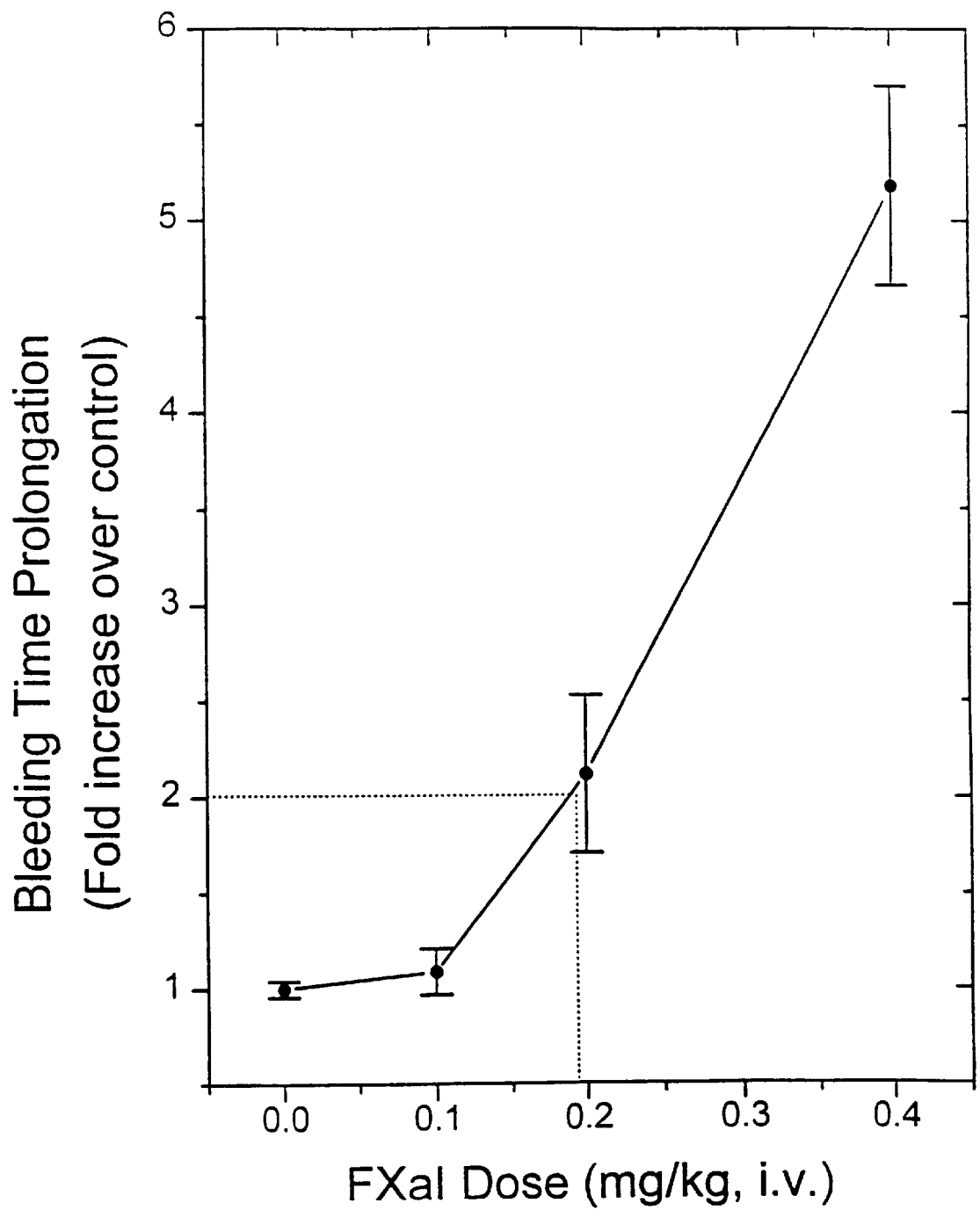

FIG. 20: Effect of FXaI on tail bleeding in mice

Tail bleeding was determined in mice injected i.v. with various doses of FXaI as indicated, five minutes after injection of the FXaI.

Figure 21:
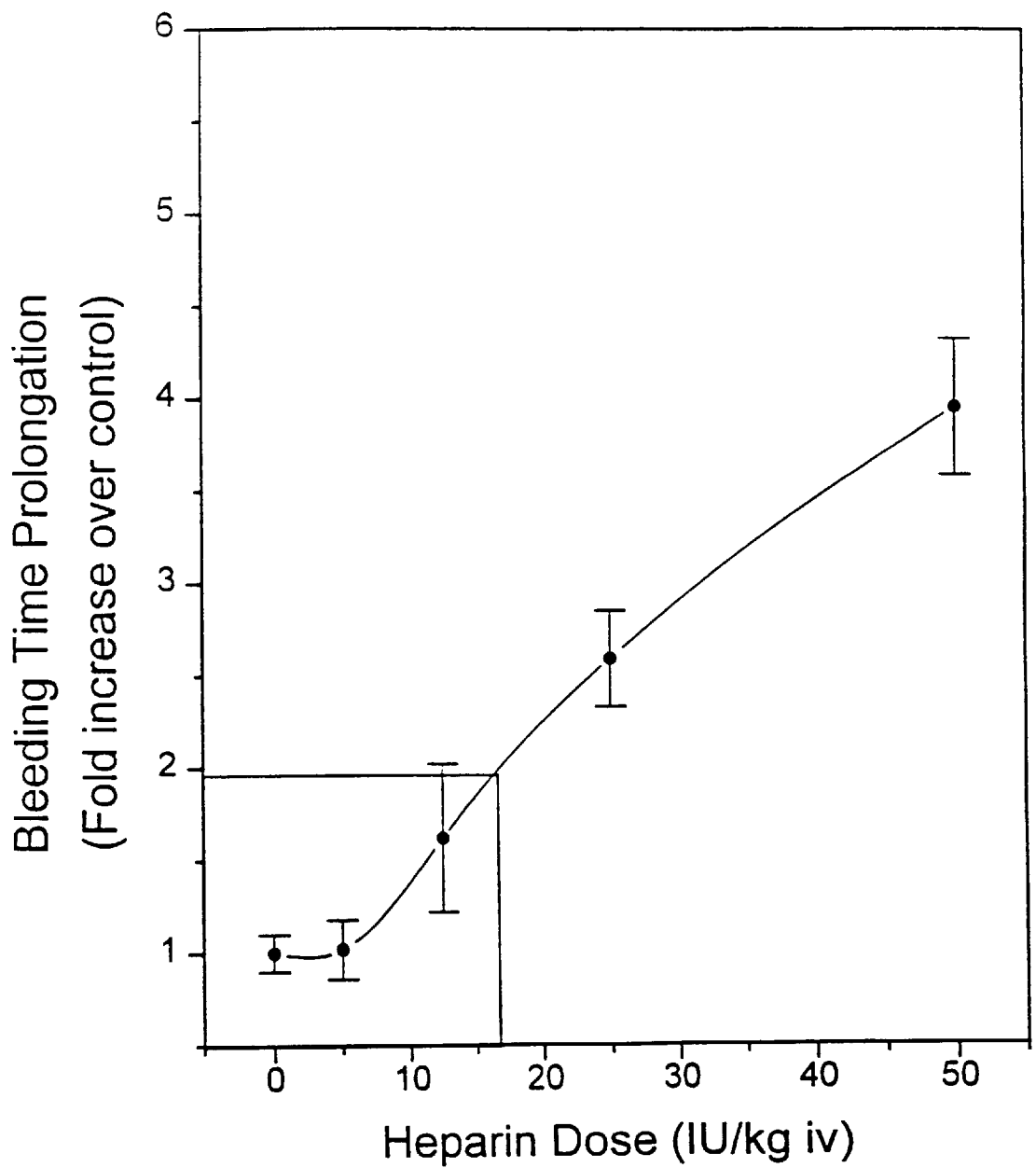

FIG. 21: Effect of heparin on tail bleeding in mice

Tail bleeding was determined in mice injected i.v. with various doses of heparin as indicated, five minutes after injection of the heparin.

Figure 22:
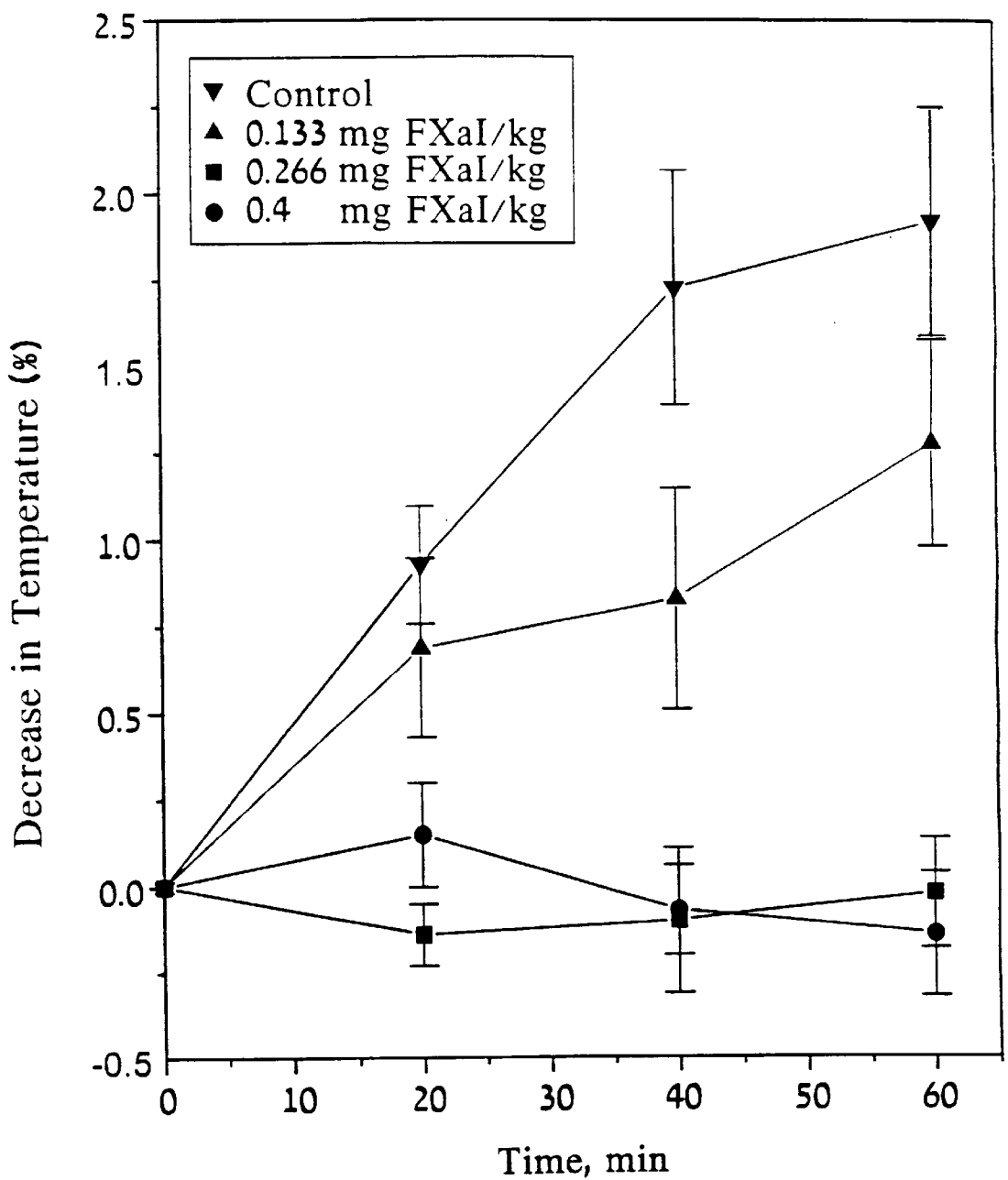

FIG. 22: The effect of FXaI on acute arterial thrombosis in the rat

The decrease arterial temperature (i) was determined in an acute arterial thrombosis model in the rat (as described in Example 17) after correction for changes in body temperature. For the two higher doses, the difference from the control is statistically significant ($p<0.01$–$0.05$ at 20 and 40 min and $p<0.001$–$0.01$ at 60 min), whereas at an FXaI dose of 0.133 mg/kg, the difference is not statistically significant.

Figure 23:
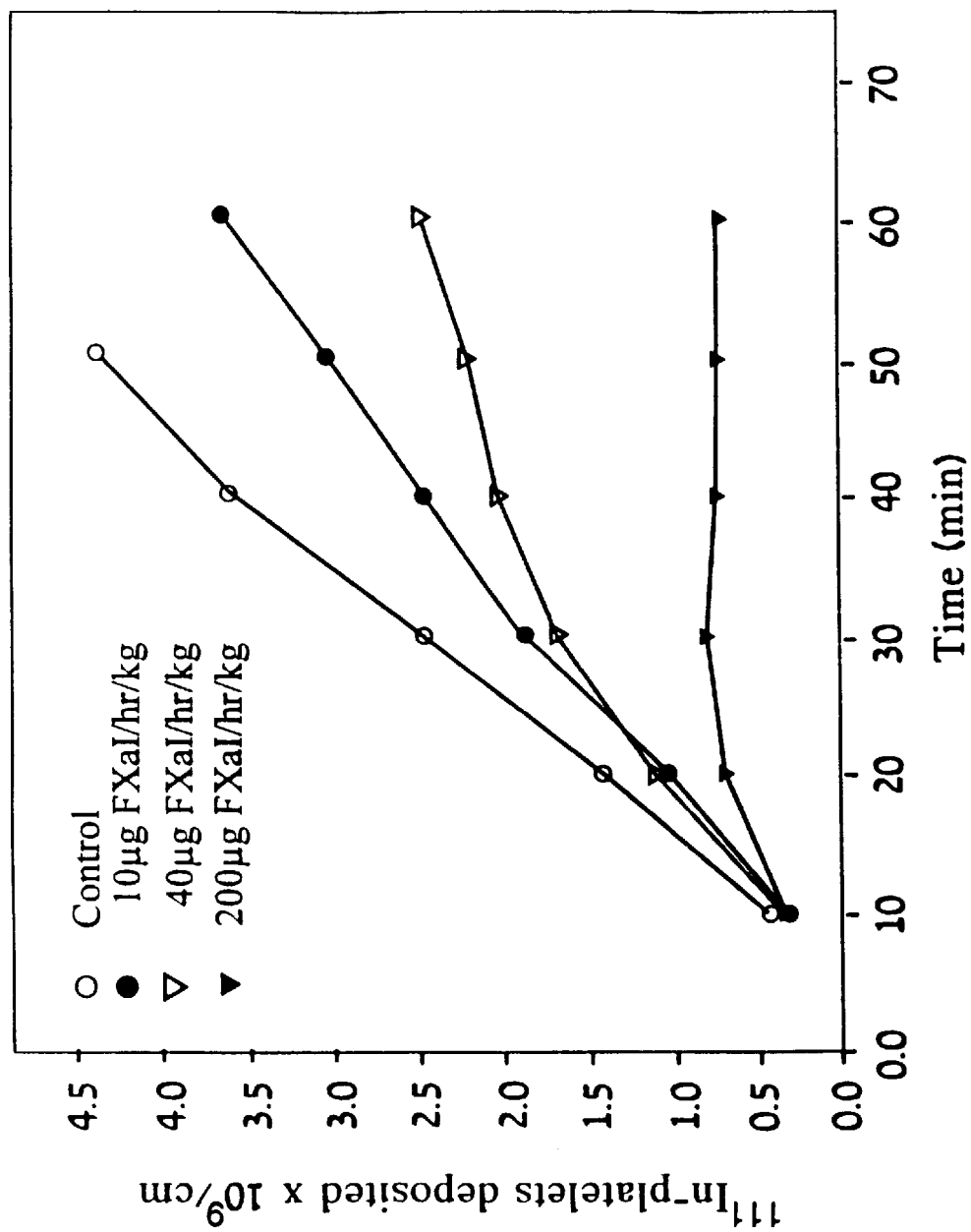

FIG. 23: Inhibition of arterial thrombosis in the baboon by FXaI

Three different baboons were each injected with three distinct doses of FXaI as indicated. One baboon was injected with PBS and served as a control. $^{111}$In-platelet deposition was measured on the dacron graft at the indicated time intervals by a gamma camera.

Figure 24:
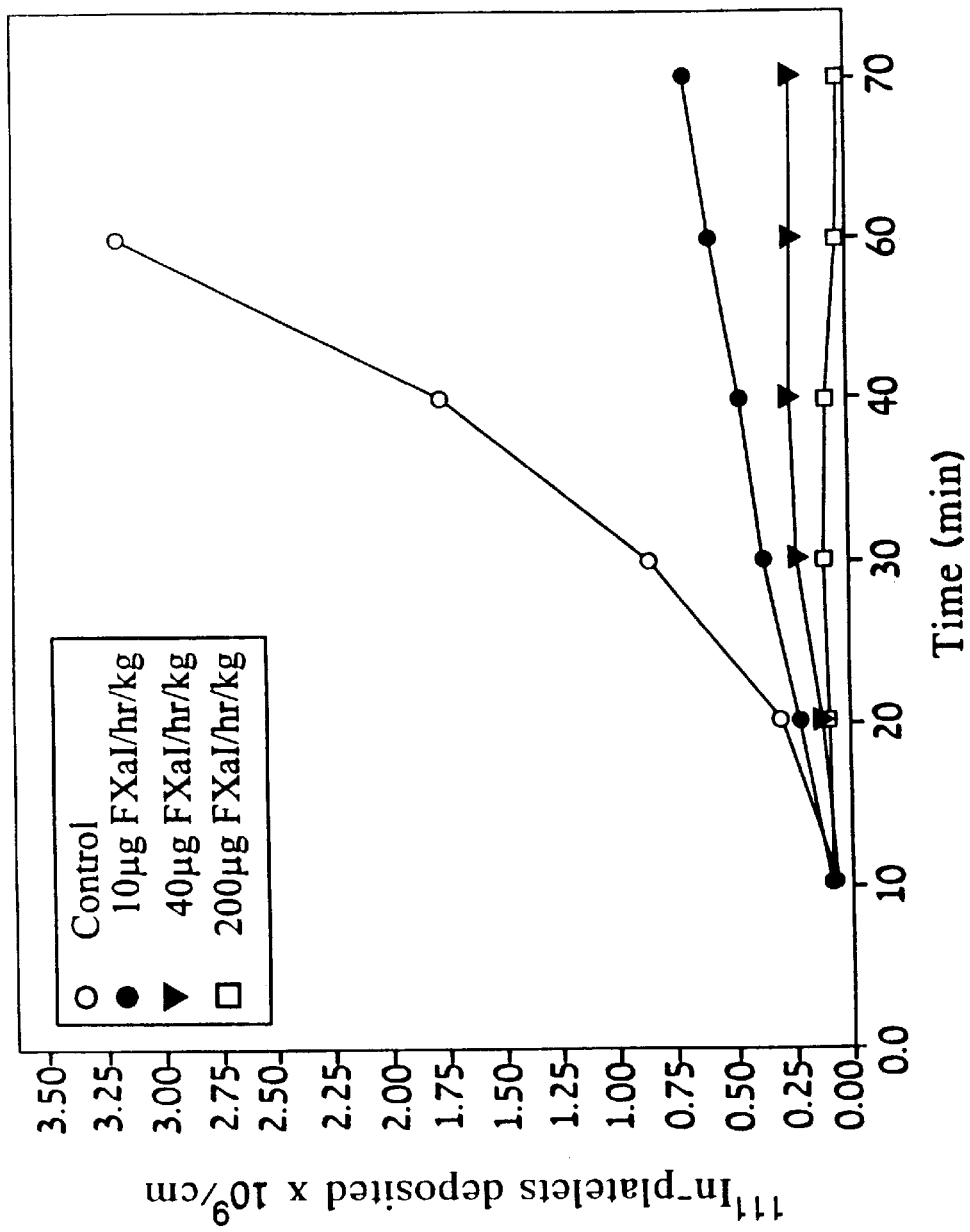

FIG. 24: Inhibition of venous thrombosis in the baboon by FXaI

Three different baboons were each injected with three distinct doses of FXaI as indicated. One baboon was injected with PBS and served as a control. "In-platelet deposition was measured in the chamber at the indicated time intervals by a gamma camera.

Figure 25:
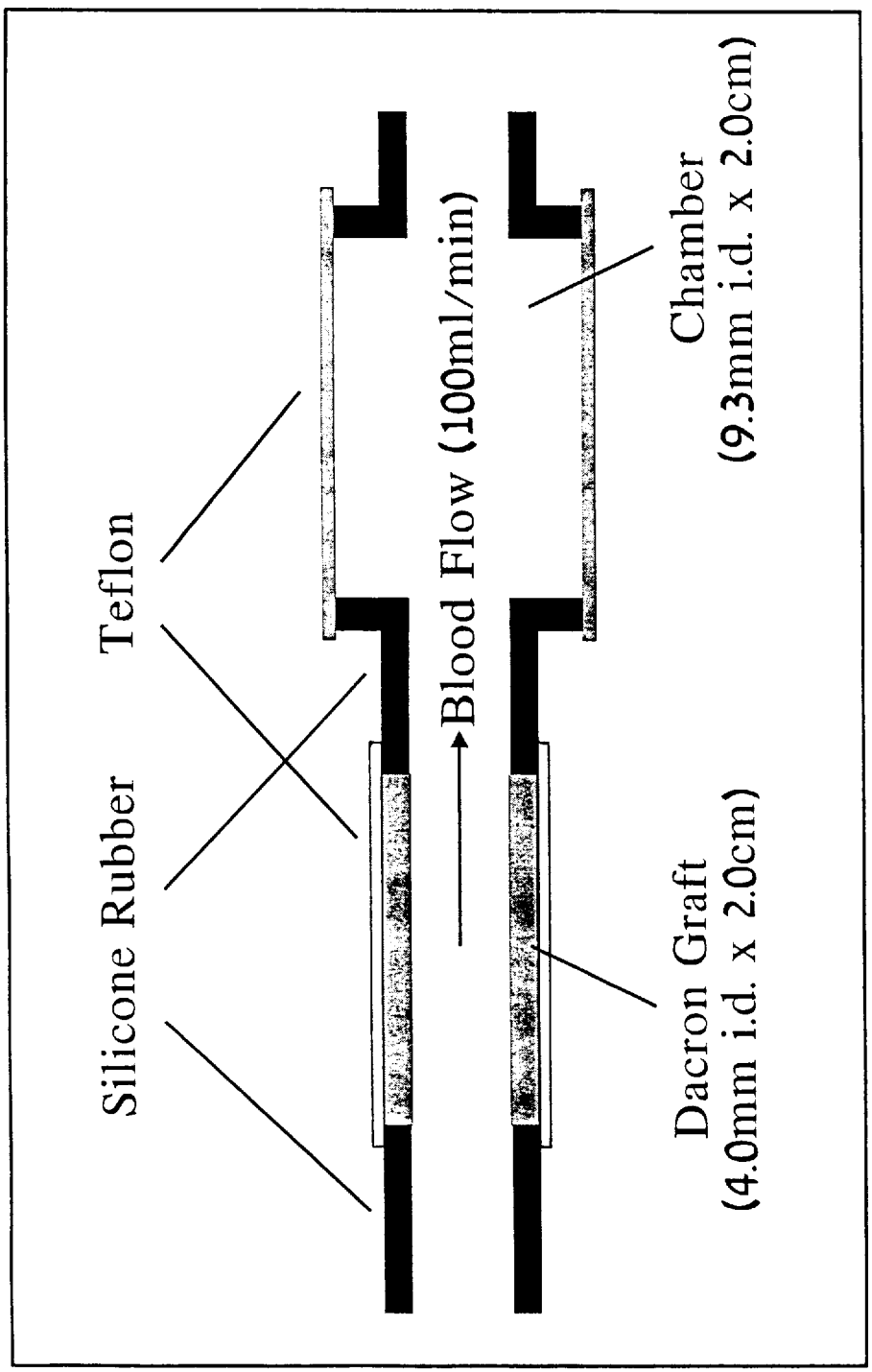

FIG. 25: Arterio-venous shunt system

A schematic drawing of the thrombogenic device used in Example 18 is depicted.

Figure 26:
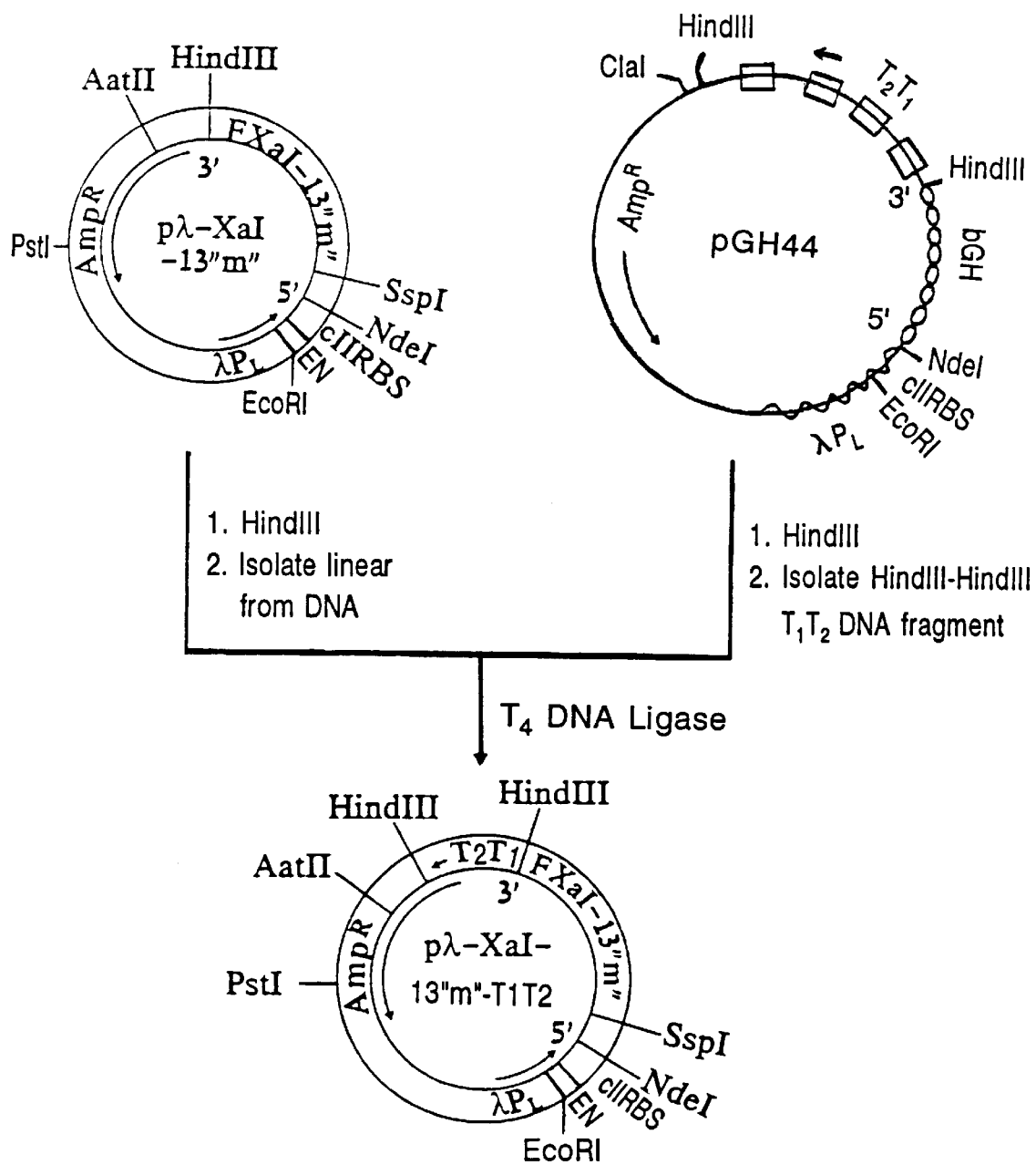

FIG. 26: Construction of expression plasmid pλ-XaI-13"m"-$T_1T_2$

Plasmid pλ-XaI-13"m"(FIG. 10) was digested with HindIII endonuclease and the linear DNA was isolated and ligated to the small HindIII-HindIII $T_1T_2$ DNA fragment obtained by HindIII endonuclease digestion of DNA plasmid pHG44 (deposited under ATCC Accession No. 39806 on Aug. 20, 1984). The newly obtained plasmid was designated pX-XaI-13"m"-$T_1T_2$.

DETAILED DESCRIPTION OF THE INVENTION

Abbreviations

The following abbreviations are used as amino acid designations:

| A | Ala | Alanine |
|---|-----|---------|
| C | Cys | Cysteine |
| D | Asp | Aspartic acid |
| E | Glu | Glutamic acid |
| F | Phe | Phenylaline |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

The present patent application discloses the identification and characterization of a novel and heretofore unknown polypeptide derived from the leech *Hirudo medicinalis*. This recombinant polypeptide is an inhibitor of FXa and is herein designated "FXaI". Recombinant FXaI is also termed Yagin. In another aspect, the present application discloses the complete gene sequence as well as the deduced amino acid sequence of the novel polypeptide. In yet another aspect, the present application discloses production in bacteria of the novel polypeptide, and its refolding to yield a biologically active protein having inhibitory activity towards the enzymatic activity of FXa.

The invention provides a polypeptide (protein) comprising the amino acid sequence

| X— | Y— | CYS | GLN | GLU | GLU | GLU | CYS | PRO | ASP | PRO | TYR | LEU | CYS |
| SER | PRO | VAL | THR | ASN | ARG | CYS | GLU | CYS | THR | PRO | VAL | LEU | CYS |
| ARG | MET | TYR | CYS | LYS | PHE | TRP | ALA | LYS | ASP | GLU | LYS | GLY | CYS |
| GLU | ILE | CYS | LYS | CYS | GLU | GLU | LEU | CYS | GLN | ASN | GLN | ASN | CYS |
| THR | LYS | ASP | MET | LEU | CYS | SER | SER | VAL | THR | ASN | ARG | CYS | ASP |
| CYS | GLN | ASP | PHE | LYS | CYS | PRO | GLN | SER | TYR | CYS | — | Z (SEQ. ID NO. 1) | wherein X is MET or absent; Y is 0–29 amino acids of the sequence LYS MET CYS TRP ASN LYS GLY CYS PRO CYS GLY GLN ARG CYS ASN LEU HIS ARG ASN GLU CYS GLU VAL ILE ALA GLU ASN ILE GLU (SEQ ID NO:2), with the proviso that if part of the sequence is present, it is the carboxy-terminal part of the sequence and wherein Val$^{24}$ may be preceded by Gly; and Z is absent or all or a part of the sequence Pro$^{110}$-Lys$^{156}$ shown in FIG. 7, with the proviso that if part of the sequence is present, it is the amino-terminal part of the sequence. The polypeptide may be glycosylated or non-glycosylated.

It is envisaged that the recombinant polypeptide of the subject invention encompasses polypeptides which are homologs of the above described polypeptide.

In preferred embodiments, the polypeptide has the amino acid sequence A-Lys$^2$-Lys$^{156}$, Ile$^{29}$-Lys$^{156}$, Glu$^{23}$-Lys$^{156}$, or A-Val$^{24}$-Lys$^{156}$ where Lys$^2$-Lys$^{156}$, Ile$^{29}$-Lys$^{156}$, Glu$^{23}$-Lys$^{156}$, and Val$^{24}$-Lys$^{156}$ are identical to the sequence shown in FIG. 7, and wherein A is MET or absent and wherein Val$^{24}$ may be preceded by Gly. In an additional aspect, the subject invention provides for biologically active recombinant FXaI.

Biologically active FXaI is defined as FXaI which has inhibitory activity towards the enzymatic activity of Factor Xa as measured by the biochemical activity assay described in Example 2.

Inhibitory activity is defined as activity which reduces the enzymatic activity of Factor Xa as measured by the above mentioned biochemical assay.

As a result of the lowering of the enzymatic activity of FXa, the extent of blood coagulation is reduced.

It is contemplated that the polypeptide of the invention may have alternative or additional biological activity or activities instead of or in addition to being an inhibitor of FXa; in particular, it may have inhibitory activity to other factors in the coagulation cascade.

As used herein, a homolog of the polypeptide of the invention is a polypeptide which has substantially the same amino acid sequence and biological activity as the polypeptide.

Thus, a homolog may differ from the polypeptide of the invention by the addition, deletion, or substitution of one or more non-essential amino acid residues, provided that the resulting polypeptide retains the biological activity of the polypeptide. Persons skilled in the art can readily determine which amino acids residues may be added, deleted, or substituted (including with which amino acids such substitutions may be made) using established and well known procedures, including, for example, conventional methods for the design and manufacture of DNA sequences coding for bacterial expression of polypeptide homologs of the subject polypeptide, the modification of cDNA and genomic sequences by site-directed mutagenesis techniques, the construction of recombinant proteins and expression vectors, the bacterial expression of the polypeptides, and the measurement of the biochemical activity of the polypeptides by means of conventional biochemical assays.

Examples of homologs are deletion homologs containing less than all the residues specified in the subject polypeptide, substitution homologs wherein one or more residues specified are replaced by other residues, and addition homologs wherein one or more amino acids residues are added to the polypeptide. All such homologs share the biological activity of the polypeptide of the invention.

Substantially the same amino acid sequence is herein defined as encompassing the addition or deletion of fewer than four amino acids at the N-terminus of the amino acid sequence of FXaI. Furthermore, there may be substitutions and/or deletions in the sequence which do not eliminate the biological activity of the protein. Such substitutions are known to those skilled in the art. Substitutions may encompass up to 10 residues in accordance with the homologous or equivalent groups described by e.g. Lehninger, Biochemistry, 2nd ed. Worth Pub., N.Y. (1975); Creighton, Protein Structure, a Practical Approach, IRL Press at Oxford Univ. Press, Oxford, England (1989); and Dayhoff, Atlas of Protein Sequence and Structure 1972, National Biomedical Research Foundation, Md. (1972).

Substantially the same biological activity refers to biological activity the same as that of the polypeptide possibly differing slightly in degree or level which would still be known by the skilled artisan to be the same biological activity.

The present application discloses DNA isolated from an mRNA derived CDNA library of Hirudo medicinalis. The polypeptides encoded by this DNA or a part thereof are inhibitors of FXa, but the amino acid sequence deduced from the DNA nucleotide sequence is substantially different from the sequence of the known naturally occurring FXa inhibitor disclosed by Rigbi (13). There is no prior disclosure of the existence of this novel polypeptide.

The polypeptide of the invention may be obtained as a "mature" protein, i.e. in the absence of any extension or fusion peptides, as prepeptides containing leader or extension peptides, or as fusion peptides containing all or a portion of another protein or polypeptide. Mature polypeptide may be obtained by direct expression or by cleavage of a fusion polypeptide or prepeptide.

In a specific embodiment, the recombinant FXaI is expressed as a mature polypeptide (i.e. lacking any amino terminal or carboxy terminal extensions such as leader peptides or fusion proteins) by E.coli 4300 containing plasmid pλ-XaI-13"m" or plasmid pλ-XaI-13"m" -T$_1$T$_2$ or plasmid pλ-XaI-13"m"-05M-T$_1$T$_2$ under control of the XPL promoter.

In another embodiment, the recombinant FXaI is produced as a fusion polypeptide by E.coli 733 containing plasmid pDeo-S-XaI-13"f" under control of the deo promoter which expresses recombinant FXaI fused to the first 58 N-terminal amino acids of a modified Cu/Zn-SOD sequence. Cu/Zn-SOD is described in coassigned U.S. Pat. No. 4,742,004 and by Steinman, H. M., *Superoxide Dismutase*, (Oberley, ed.) CRC Press, Florida, pages 11–68, 1982.)

In yet another embodiment, the recombinant FXaI is obtained as a prepeptide containing a putative extension sequence expressed by *E.coli* 4300 containing plasmid pλ-XaI-13"1".

In a more preferred embodiment, the recombinant FXaI is produced as a fusion polypeptide by plasmid pλSOD-NGE-XaI-13"m" which encodes a fusion polypeptide containing a 63 amino acid fragment of a modified Cu/Zn-SOD sequence, a hydroxylamine cleavage site, and the FXaI 13"m" polypeptide having the sequence $glu^{23}$-$lys^{156}$ shown in FIG. 7. One skilled in the art may readily obtain the FXaI 13"m" polypeptide by cleavage of the fusion protein at the engineered cleavage site.

Mature recombinant FXaI may thus be obtained by direct expression or by cleavage of a fusion protein or prepeptide by known methods. Furthermore, one skilled in the art knows how to obtain the mature recombinant FXaI from other fusion peptides and other manipulations of the DNA encoding FXaI DNA using known and readily available materials and methods (e.g. Nilsson et al., Current Opinion in Structural Biology, 2:569–575 (1992) and Hopp et al., BioTechnology 6:1204–1210 (1988)).

The subject invention further provides DNA encoding the polypeptides of the subject invention.

The subject invention also provides expression plasmids comprising the DNA encoding the polypeptides of the subject invention.

Examples of vectors that may be used to express DNA encoding the polypeptides are viruses such as bacterial viruses, e.g., bacteriophages (such as phage lambda), cosmids, plasmids, and other vectors. Genes encoding the relevant polypeptides are inserted into appropriate vectors by methods well known in the art. For example, using conventional restriction endonucleases, inserts and vector DNA can both be cleaved to create complementary ends which pair with each other and are then ligated together with a DNA ligase. Alternatively, synthetic linkers harboring base sequences complementary to a restriction site in the vector DNA can be ligated to the insert DNA, which is then digested with the restriction enzyme which cuts at that site. Other means are also available and are known to those skilled in the art.

Vectors comprising a sequence encoding the polypeptide may be adapted for expression in a range of prokaryotic and eukaryotic host cells e.g. bacteria, fungi, yeast, plant, insect, and mammalian cells such as CHO, chicken embryo, fibroblast, kidney and other known cell lines. These vectors additionally comprise regulatory elements necessary for expression of the cloned gene located relative to the sequence encoding the polypeptide so as to effect expression of the polypeptide in the host. Examples of regulatory elements required for expression include promoters, operators, and ribosomal binding sites. For example, a bacterial expression vector may include a promoter-operator sequence such as λ $P_L O_L$ or deo promoters and operators. For initiation of translation, ribosomal binding sites such as $\lambda C_{II}$ or deo ribosomal binding sites may be used. Additional appropriate elements such as repressors and enhancers may also be present. Those skilled in the art know how to use regulatory elements appropriate for various expression systems.

The regulatory elements are positioned within the plasmid relative to the DNA encoding the polypeptides so as to effect expression of the polypeptides in a suitable host cell. In preferred embodiments of the invention, the regulatory elements are positioned close to and upstream of the DNA encoding the polypeptides. Other suitable regulatory elements are known to those skilled in the art. Such vectors may be obtained commercially or constructed from the sequences described by methods well known in the art, for example U.S. Pat. No. 4,831,120, issued May 16, 1989 and U.S. Pat. No. 5,143,836, issued Sep. 1, 1992, which disclose methods concerning XPL, and European Patent Application Publication No. 303,972, published Feb. 22, 1989 which discloses methods concerning the deo promoter.

The invention provides plasmids encoding any of the recombinant proteins described above.

A preferred embodiment is plasmid pSP65-XaI-13, deposited under ATCC Accession No. 69134 on Dec. 1, 1992. Plasmid pSP65-XaI-13 does not express any protein since it lacks suitable regulatory elements; however, one skilled in the art knows how to manipulate the DNA of plasmid pSP65-XaI-13 in order to obtain expression of recombinant FXaI.

In more preferred embodiments, these plasmids are expression plasmids designated pDeo-S-XaI-13"f" deposited under ATCC No. 69137 on Dec. 1, 1992, plasmid pλ-XaI-13"m" deposited under ATCC Accession No. 69135 on Dec. 1, 1992, and plasmid pλSOD-NGE-XaI-13"m" deposited under ATCC Accession No. 69269 on Mar. 23, 1993.

In additional preferred embodiments, the expression plasmids are plasmids pλ-XaI-13"m"-$T_1T_2$, pλ-XaI-13"m"-05M-$T_1T_2$ and pλ-XaI-13"m"-05M.

Those skilled in the art will understand that the plasmids deposited in connection with this application may be readily altered by known techniques (e.g. site-directed mutagenesis or insertion of linkers) to encode expression of related polypeptides (homologs). Such techniques are described for example in Sambrook, J., Fritsch, E. F. and Maniatis, T. (1989) Molecular Cloning: A Laboratory Manual, 2nd edition, Cold Spring Harbor Laboratory Press.

The expression plasmids of the invention may be introduced into suitable host cells, preferably bacterial host cells. However, those skilled in the art will understand that the expression plasmids of this invention may be suitably modified for introduction into a range of prokaryotic and eukaryotic host cells as described above.

The bacteria used as hosts may be any strains including auxotrophic (such as *E. coli* A1645), prototrophic (such as *E. coli* A4255), and lytic strains; $F^+$ and $F^-$ strains; strains harboring the $cI^{857}$ repressor sequence of the λ prophage such as *E. coli* A1645 and A4255); and strains devoid of the deo repressors and/or the deo gene (see European Patent Application Publication No. 0303972, published Feb. 22, 1989). *Escherichia coli* A4255 has been deposited under ATCC Accession No. 53468, and *Escherichia coli* Sø930 has been deposited under ATCC Accession No. 67706. In preferred embodiments, *E. coli* 4300 is used as host for expression plasmids under control of $\lambda P_L$ and *E. coli* 733 is used as host for expression plasmids under control of the deo promoter.

Preferred bacterial host cells are *Escherichia coli* cells. Examples of suitable *Escherichia coli* cells are strains 733 and 4300 or 4300 ($F^-$), but other *Escherichia coli* strains and other bacteria can also be used as hosts for the plasmids. An example of a eukaryotic cell is an insect cell. Preferred insect cells are Sf-9 cells harboring a baculovirus expression system.

The invention provides a host-plasmid system which comprises a bacterial cell with any of the aforementioned expression plasmids.

All the E. coli host strains described above can be "cured" of the plasmids they harbor by methods well-known in the art, e.g. the ethidium bromide method described by R. P. Novick (1969) in Bacteriol. Review 33, 210.

One skilled in the art knows how to produce the polypeptides disclosed herein from different plasmids and/or different nucleotide sequences encoding the same amino acid sequences due to the degeneracy of the genetic code. One skilled in the art can also produce substantially identical homologs having small changes in the amino acid sequence which do not affect the structure or specific biological activity of the polypeptide. Such homologs are also encompassed by the invention.

In addition, the invention provides a method of producing biologically active recombinant FXaI which comprises transforming a host cell with an expression plasmid encoding the polypeptide, culturing the transformed host cell so that the cell produces the polypeptide encoded by the plasmid, and recovering the polypeptide so produced.

In another aspect, the invention provides a method for producing a biologically active recombinant FXaI polypeptide wherein the host cell is a bacterial cell, and the recovering comprises:

(a) disrupting the cells so as to produce a lysate containing the polypeptide;

(b) treating the lysate so as to obtain inclusion bodies containing the polypeptide;

(c) treating the inclusion bodies so as to obtain the polypeptide in soluble form;

(d) treating the resulting soluble polypeptide so as to form biologically active polypeptide;

(e) recovering the biologically active polypeptide so formed; and (f) purifying the biologically active polypeptide so recovered.

In a preferred embodiment, the treating of step (c) comprises the addition of a denaturant, the treating of step (d) comprises contacting the polypeptide with a mixture of a thiol-containing compound and a disulfide, and the purifying of step (f) comprises column chromatography.

In a more preferred embodiment, the denaturant is guanidinium chloride or urea, the thiol containing compound is glutathione, thioredoxin, β-mercaptoethanol, or cysteine, the disulfide is oxidized glutathione, cystine, or the product of air oxidation of mercaptoethanol, and the column chromatography comprises either one or both of Q-Sepharose chromatography and Heparin-Sepharose chromatography or either one or both of Q-Sepharose chromatography and S-Sepharose chromatography.

The invention further provides a composition comprising any of the polypeptides described effective to obtain a desired therapeutic effect resulting from the biological activity of the polypeptide, and a suitable carrier.

In a preferred embodiment, the desired therapeutic effect is the reduction of the extent of blood coagulation and thrombosis. The extent of blood coagulation may be represented by in vitro coagulation assays such as APTT.

The invention also provides a method of reducing the extent of blood coagulation comprising contacting the blood with an amount of the claimed polypeptide effective to reduce the extent of blood coagulation.

In a preferred embodiment, the contacting is effected in vivo in a subject. In a more preferred embodiment, the subject suffers from excessive blood coagulation.

In particular embodiments, the subject suffering from excessive blood coagulation has a condition selected from the group consisting of vascular disorders, post-operative trauma, tendency towards venous thromboembolism associated with obesity, pregnancy, the use of oral contraceptives, and prolonged immobilization.

Accordingly, the invention provides a method of reducing the extent of blood coagulation and thrombosis in a cerebrovascular disorder such as stroke or other cerebrovascular disorders.

The invention provides a method of reducing the extent of blood coagulation in a condition of excessive blood coagulation such as occurs in thrombosis, more particularly venous thrombosis and more particularly deep venous thrombosis or disseminated intravascular coagulation.

The invention further provides a method of reducing the extent of blood coagulation in a condition of excessive blood coagulation such as occurs in arterial thrombosis such as thrombosis of a coronary artery.

As described above, thrombosis often occurs following thrombolysis. Accordingly, the invention provides a method of reducing the extent of blood coagulation following thrombolysis. In a preferred embodiment, the thrombolysis is effected with a fibrinolytic agent. In particular embodiments, the fibrinolytic agent is tissue plasminogen activator or streptokinase. The polypeptide may be administered before, during, or after the administration of the fibrinolytic agent, or bound to the fibrinolytic agent.

The invention also provides a method of inhibiting the activity of Factor Xa which comprises contacting Factor Xa with an amount of the polypeptide effective to inhibit the activity of the Factor Xa.

In an additional embodiment, the polypeptide of the invention may be used to prevent recurrent influenza infection. Influenza infection is a dynamic process comprising infection and reinfection of cells by the virus. The activation enzyme implicated in A-type influenza infection has been shown to be very similar to chicken blood coagulation Factor Xa (Gotoh B. et al. (1990), EMBO J. 9: 4185–4190 and Ogasawara T. et al (1992), EMBO J. 11: 467–472). It is therefore possible that the corresponding human FXa is involved in influenza infections occurring in humans.

It is envisioned that an FXa inhibitor would be useful in preventing recurrent influenza infection. In a specific embodiment, the FXa inhibitor would be the polypeptide of the invention. It is also contemplated that the polypeptide might be administered in conjunction with additional therapeutic agents. In a particular embodiment, the additional therapeutic agent comprises an oxygen free radical scavenger. In a preferred embodiment, the oxygen free radical scavenger is superoxide dismutase. In still more preferred embodiments, the superoxide dismutase is Cu/Zn-SOD (U.S. Pat. No. 4,742,004) or MnSOD (coassigned U.S. Ser. No. 842,740, filed Feb. 27, 1992 and UK Patent No. GB 2,183,658, Apr. 25, 1990).

Such treatment would have numerous advantages over presently available therapeutic and prophylactic methods of handling influenza infection. Presently used methods of influenza prevention are based on immunization against the influenza virus. This method has proved unreliable due to the high frequency of mutation of the influenza virus, as well as the large number of viral strains.

Use of an inhibitor of the mechanism of infection would therefore be greatly advantageous by not being based on the immunological properties of the viral particle, and therefore not limited to a particular strain.

Furthermore, since influenza is a bronchopulmonary disease, the treatment would preferably be administered as an aerosol, thus providing a simple method of administration.

In an additional aspect, the invention provides an antibody which specifically reacts with an epitope of the polypeptide. In a particular embodiment, the antibody is a monoclonal antibody. The invention also encompasses a polypeptide which competitively inhibits the specific reacting of the antibody.

Plasmids and Strains Deposited in Connection with the Present Invention

Various plasmids and *E. coli* strains useful in carrying out the methods of the invention were deposited with the American Type Culture Collection, 12301 Parklawn Drive, Rockville, Md. 20852 pursuant to and in satisfaction of, the requirements of the Budapest Treaty on the International Recognition of the Deposit of Microorganisms for the Purposes of Patent Procedure.

These plasmids include plasmid pSP65-XaI-13 deposited in *E. coli* MC1061 under ATCC Accession No. 69134 which contains cDNA encoding FXaI of clone 13; plasmid pDeo-S-XaI-13"f"deposited in *E. coli* 733 under ATCC Accession No. 69137 which expresses FXaI protein under control of the deo promoter fused to 58 N-terminal amino acids of a modified sequence of human Cu/Zn-SOD; pλ-XaI-13"m" deposited in *E. coli* 4300 under ATCC Accession No. 69135 which expresses a mature FXaI polypeptide. These aforementioned plasmids were deposited on December 1, 1992. Plasmid pXSOD-NGE-XaI-13$^{11}$m" which was deposited in *E. coli* 4300 (F$^-$) on Mar. 23, 1993 under ATCC Accession No. 69269 expresses a cleavable fusion protein containing a 63 amino acid fragment of a modified Cu/Zn-SOD sequence, a hydroxylamine cleavage site, and the FXaI 13"m" polypeptide. Deposited bacterial strains are *E. coli* 4300 which is a host cell for plasmids controlled by the λ P$_L$ promoter, deposited as noted above under ATCC Accession No. 69135 and *E. coli* 733 which is a host cell for plasmids controlled by the deo promoter, deposited as noted above under ATCC Accession No. 69137.

Additionally, plasmid pMLK-100, a vector harboring the λP$_L$ promoter, was deposited in *E. coli* 4300 under ATCC Accession No. 68605 on Apr. 16, 1991 and plasmid pHG44, a vector harboring the T1T2 transcription termination sequence was deposited in *E. coli* under ATCC Accession No. 39806 on Aug. 20, 1984.

EXAMPLES

The Examples which follow are set forth to aid in understanding the invention but are not intended to, and should not be construed so as to, limit its scope in any way. The examples do not include detailed descriptions for conventional methods employed in the isolation of cDNA, the construction of vectors, the insertion of genes encoding polypeptides of interest into such vectors, or the introduction of the resulting plasmids into bacterial hosts. Such methods are well known to those skilled in the art and are described in numerous publications including Sambrook, Fritsch, and Maniatis, *Molecular Cloning: A Laboratory Manual,* 2nd Edition, Cold Spring Harbor Laboratory Press, USA, (1989).

Examples 1 and 2 describe the isolation and characterization of a naturally occurring FXa inhibitor from the saliva of the leech *Hirudo medicinalis.*

Examples 3–18 describe how DNA encoding the polypeptide obtained above was used to identify a novel DNA sequence encoding the novel polypeptide of the present invention, and additional novel and inventive embodiments of the present invention.

Example 1

Purification of Naturally Occurring FXa Inhibitor From Saliva of *H. medicinalis*

An FXa inhibitor was purified from dilute leech saliva (DLS) of *Hirudo medicinalis.* DLS was obtained as described by Rigbi et al., Comp. Biochem. Physiol. 87B:567–573 (1987).

In brief, a phagostimulatory solution of 0.001M arginine in saline kept at 37° C. was placed over a washed membrane (sausage skin, obtained from Nippi Gelatin Casing, Tokyo, Japan) which was stretched across a cylinder open at both ends. Starved leeches were allowed to suck the solution into their huge crop until satiated. As the feeding solution was not stirred, it is assumed that most of the saliva excreted into it was reimbibed. Following cessation of feeding, the ingested solution containing the saliva was forced out through the mouth by squeezing the leech from the posterior end forwards. Colorless fluid, designated dilute leech saliva (DLS), was collected.

Figure 1:
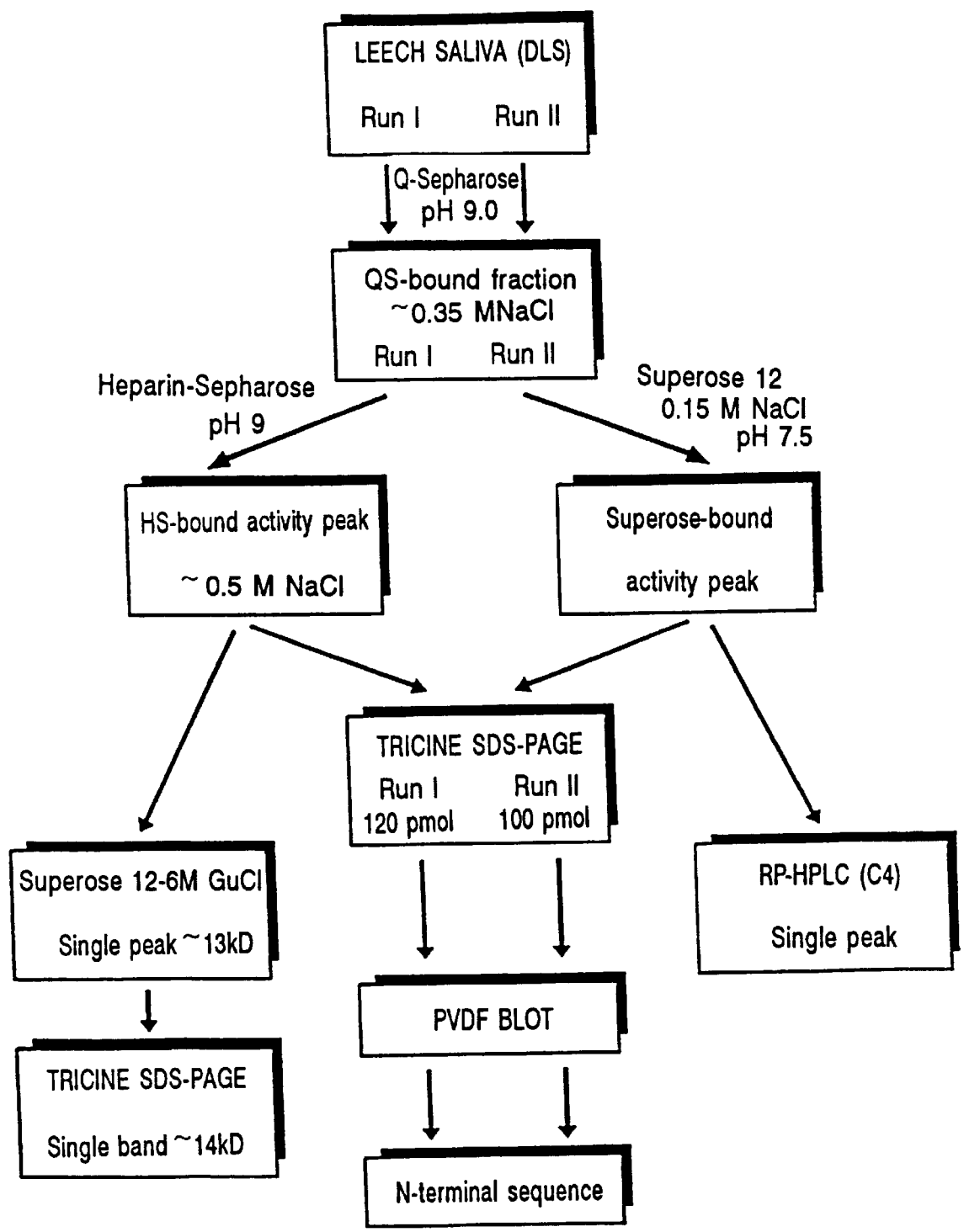
FIG. 1: Purification and Identification of FXa Inhibitor In Leech Saliva

Two methods of purification of the proteins from DLS are described below. The two methods are similar and consist of anion exchange chromatography on a quaternary aminomethyl column (Mono-Q or Q-Sepharose) followed by either gel filtration chromatography on Superose 12 or by affinity chromatography on Heparin-Sepharose. In both cases, the identity and the homogeneity of the preparation were verified by SDS-PAGE and at least one supplementary method. These purification protocols are summarized in FIG. 1.

1. Purification on Mono-O followed by Superose 12.

DLS obtained from about 25 leeches (150 ml) was diluted with an equal volume of 20 mM Tris-HCl pH 8.9, and applied to an FPLC Mono-Q column (5×50 mm). The column was eluted with a linear gradient of 0–0.5M NaCl in the same buffer (80 ml) at a flow rate of 1 ml/min. Absorbance was monitored at 280 nm. The column was then washed with a second linear gradient of 0.5M–1M NaCl in the same buffer (20 ml) and at the same flow rate followed by an additional 5ml of 1M NaCl. Fractions of 1 ml were collected and assayed for both FXa inhibitor activity and hirudin activity. The peak of FXa inhibitor activity eluted at about 0.35M NaCl and was separate from the peak of hirudin activity. The fractions containing FXa inhibitory activity were pooled and applied to a Superose 12 column 10×900 mm (three 10×300 mm columns in series). Elution was carried out at room temperature with 20 mM Tris-HCl pH 8 containing 150 mM NaCl at a flow rate of 0.3 ml/min. Absorbance was monitored at 280 nm. The FXa inhibitor activity eluted under these conditions as a single peak with an apparent molecular weight of 4kD. In contrast, electrophoresis on Tricine SDS-PAGE of the fraction containing the purified FXa inhibitory activity revealed a single band of molecular weight of about 14 kD. As will be described in Example 2, this inconsistency in molecular weight determination may be due to nonspecific interactions of the Superose 12 with the FXa inhibitor leading to retardation of elution of the FXa inhibitor from the column.

The purified polypeptide was also analyzed by reverse phase HPLC (RP-HPLC) as follows. The FXa inhibitor, purified on Superose 12, was dialyzed against water, lyophilized, redissolved in 1 ml of 0.1% trifluoroacetic acid (TFA), and loaded onto a 7μ RP-300 column (Aquapore, Brownlee Labs) attached to a Kontron Model 420/422S HPLC. Elution was carried out with a linear gradient of 0–100% acetonitrile in 0.01% TFA (60 ml) at a flow rate of 1 ml/min. Absorbance was monitored at 220 nm. A single peak with a retention time of 38.51 minutes was observed thus demonstrating that the FXa inhibitor was purified to homogeneity.

2. Purification on Q-Sepharose followed by Heparin-Sepharose.

DLS obtained from about 50 leeches (320 ml) was diluted with an equal volume of 20 mM Tris-HCl pH 8.9, and applied to a Q-Sepharose column (10×50 mm). The column was eluted with a linear gradient of 0–0.5M NaCl in the same buffer (70 ml) at a flow rate of 1 ml/min; absorbance was monitored at 280 nm. The column was then washed with 1M NaCl in the same buffer at the same flow rate. Fractions of 1 ml were collected and assayed for both FXa inhibitory activity and hirudin activity. This verified that the FXa inhibitor peak was indeed separated from the hirudin peak. The FXa inhibitor eluted in a single peak at about 0.35M NaCl, which was similar to the elution from Mono-Q described above. The fractions containing FXa inhibitory activity were pooled and dialyzed against 20 mM Tris-HCl pH 8.9. An aliquot of 7 ml was then applied to a Heparin-Sepharose column (10×50 mm). Elution was carried out with a linear gradient of 0–0.5M NaCl in the same buffer (70 ml) at a flow rate of 1 ml/min and absorbance monitored at 280 nm. The column was then washed with 1M NaCl in the same buffer and at the same flow rate. Fractions of 1 ml were collected and assayed for FXa inhibitory activity. The purified FXa inhibitor eluted in a single peak at about 0.30M NaCl. By this protocol, the FXa inhibitor was purified approximately 600-fold with an overall yield of 14%. As will be described below, Tricine SDS-PAGE analysis of this preparation revealed a single band with a molecular weight of 14 kD. The homogeneity of the FXa inhibitor purified by this procedure was further verified by gel permeation chromatography under denaturing conditions.

Example 2

Characterization of FXa Inhibitor Isolated from DLS of Hirudo medicinalis

1. Molecular Weight 1.1 Tricine SDS-PAGE

Various preparations of the FXa inhibitor prepared as described in Example 1 were analyzed to evaluate both the degree of homogeneity and the molecular weight of the protein. The protocol used was a modified version of the method of Schagger et al. (Anal. Biochem. 166:368–379 (1987)). The band corresponding to the FXa inhibitor migrated to a position of about 14kD and in some cases as a broader band of about 12–14kD.

1.2. Gel Permeation Chromatography on BioGel P-60

Molecular weight was also determined by gel permeation chromatography of a crude preparation of the FXa inhibitor on BioGel P-60. FXa inhibitory activity eluted at a retention time corresponding to a molecular weight of 14 kD. As mentioned above, the molecular weight of the FXa inhibitor as determined under denaturing conditions by electrophoresis on Tricine SDS-PAGE was also 14 kD, thus demonstrating that the FXa inhibitor is a 14kD monomer.

2. N-terminal sequence

Samples of FXa inhibitor purified from leech saliva by the two procedures described in Example 1 were further resolved by Tricine SDS-PAGE and electroblotted onto a PVDF membrane. The membrane slice containing the FXa inhibitor was subjected to automatic sequencing (Applied Biosystems Microsequencer, Model 475A) for 20 cycles.

The following sequence was obtained for samples purified by both of the above described methods:

Y — E — V — I — Y — V — D — D — P — C*— E — D — S — D —
Tyr —Glu —Val —Ile —Tyr —Val —Asp —Asp —Pro —Cys —Glu —Asp —Ser —Asp —

C*— E — D — G — N — K (SEQ. ID NO. 12)
Cys —Glu —Asp —Gly —Asn —Lys (SEQ. ID NO. 13)

* Cysteines are not detected by this method of amino acid sequencing and were later deduced from the DNA sequence.

The same N-terminal sequence was obtained following pyroglutamate aminopeptidase treatment showing that there is no FXa inhibitor isoform which is blocked by pyroglutamate at its N-terminus.

3. Biochemical activity assay

The assay of FXa inhibitory activity is based on the inhibition of the FXa-mediated hydrolysis of the chromogenic substrate methoxycarbonyl-D-cyclohexylglycyl-glycyl-arginyl p-nitroanilide (CHG) as described below.

FXa activity is observed as the increase in absorbance at 405 nm ($\epsilon_M$=9920 $M^{-1}cm^{-1}$), due to the release of p-nitroaniline. The kinetic parameters for hydrolysis of this substrate by FXa are as follows: catalytic constant=130 $sec^{-1}$ and $K_m$=15 $\mu$M. The appropriate substrate concentration was determined from the molar absorbance which is 8210 at 342 nm. The reaction mixture contains 50 mM Tris-HCl pH 8.2, 5 mM $CaCl_2$, 200 mM NaCl, 0.1% PEG, 40 $\mu$M substrate, and approximately 2 nM FXa. The FXa concentration is determined more precisely from the initial (first 20 seconds) rate of CHG hydrolysis at 40 $\mu$M in the absence of inhibitor based on the kinetic parameters mentioned above.

Inhibition of the increase in absorbance may be observed in the presence of the FXa inhibitory activity of an FXa inhibitor such as FXaI of the present invention. The inhibitor concentration is the difference in absorbance between the reaction in the presence and absence of inhibitor multiplied by the FXa concentration.

This determination assumes the formation of a 1:1 enzyme-inhibitor complex, and further assumes that the dissociation constant ($K_i$) is low enough (i.e., tight binding) to enable essentially total binding of the inhibitor (FXa inhibitor) to the enzyme (FXa). However, analysis of the saturation shape of the dose-response curve (the degree of inhibition versus inhibitor concentration) of the naturally occurring FXa inhibitor isolated from the saliva of the leech provides evidence that a finite and non-negligible dissociation of the inhibitor-enzyme complex occurs under these conditions.

The degree of dissociation of the FXa-FXa inhibitor complex is characterized by the inhibition constant ($K_i$) and may be determined from the inhibited velocity of the hydrolysis of the chromogenic substrate CHG. These results may be analyzed according to kinetic schemes of competitive inhibition for enzyme-inhibitor complexes, essentially as described in Dixon and Webb, Enzymes (3rd ed.), Academic Press, New York, (1979).

The inhibitor concentration determined by the above method may therefore be underestimated. It is therefore useful to define the FXa inhibitor concentration as the concentration required to obtain a constant degree of inhibition, usually 50%, and to define the amount causing 50% inhibition ($IC_{50}$) under these reaction conditions to be 1 milliunit (mu) or 1 pmol.

The FXa inhibitor activity assay used to determine concentration during purification and characterization was performed in an Elisa Titertek Twin Reader, Type 380 (EF LAB) or in a Phillips (Model PU 8720) UV/Vis scanning spectrophotometer.

The inhibitory activity of a FXa inhibitor may also be assayed by its effect on FXa in a prothrombinase complex. The phospholipid used was rabbit brain cephalin (Sigma). The contents of one vial, suspended in 1 ml 0.15M NaCl were diluted 1:40 in the reaction mixture, i.e. 2.5 $\mu$l/100$\mu$l. The concentrations of the other components were: FXa 250 pM, prothrombin 2.67 $\mu$M, FVa 4.2 nM and $Ca^{++}$ 1 mM in 20 mM Tris-HCl pH 7.4/150 mM NaCl/0.1 polyethylene glycol 6000. Following 10 minutes of preincubation at 37° C., the reaction was initiated by the addition of prothrombin. Aliquots were removed at various time intervals. The reaction was stopped by 10 mM EDTA and aliquots were kept on ice until assayed. The inhibition of FXa by a FXa inhibitor (e.g. FXaI of the present invention) was observed as the effect of FXaI on the generation of thrombin from prothrombin at 37° C. The amount of thrombin generated was assayed using 80 $\mu$g of the synthetic thrombin p-nitroanilide substrate S-2238 (Kabivitrum, Sweden) at 23° C.

The results obtained for naturally occurring FXa inhibitor were $K_i$ of 72pM and $IC_{50}$ of 190pM.

In some later experiments (e.g. Example 14), slight modifications were made to the above protocol of the prothrombinase complex assay: the assay mix contained 50 pM FXa and 1.35 $\mu$M prothrombin instead of 250 pM FXa and 2.67 $\mu$M prothrombin resulting in a Ki of 120pM.

Example 3

Cloning of FXa Inhibitor cDNA by PCR

The following procedure is shown schematically in FIG. 4. Total RNA was extracted from 120 leeches, *Hirudo medicinalis*. From the total RNA, 35 $\mu$g of poly $A^+$ mRNA were isolated (using the Fast Track™ mRNA isolation kit, Invitrogen). An aliquot (5 $\mu$g) of the poly $A^+$ mRNA so obtained was used as template in a reverse transcription reaction in the presence of the following synthetic primer:

The 15-mer oligo-dT sequence provides complementarity to the poly A sequence of the various mRNAs.

Following synthesis of the single stranded complementary DNA (ss-cDNA), the mRNA was degraded by alkali treatment (0.3M NaOH overnight at room temperature). An aliquot of the neutralized ss-cDNA was then subjected to PCR amplification using as reverse primer the following synthetic degenerative DNA oligomer:

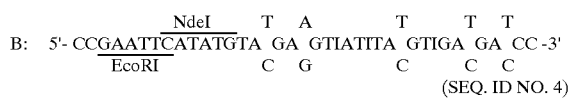

This synthetic primer was prepared in accordance with the first nine N-terminal amino acids of the naturally occurring FXa inhibitor (Example 2) and encodes the sequence:

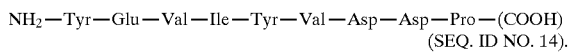

The PCR amplification conditions were as follows:

| | |
|---|---|
| 1. Primer A | 0.2 $\mu$g |
| 2. Primer B | 0.2 $\mu$g |
| 3. ss-cDNA | 5 $\mu$l (5% of total) |
| 4. 5 mM dNTP | 4 $\mu$l |
| 5. 10 X PCR buffer | 10 $\mu$l |
| 6. Taq polymerase | 0.2 $\mu$l (8 U/$\mu$l (USB)) |
| 7. $H_2O$ | 81 $\mu$l |
| 8. 40 cycles × [1' at 94° C.; 3' at 37° C. and 4' at 72° C.] | |

To analyze the PCR amplification products, 10 $\mu$l of the 100 $\mu$l reaction were loaded onto a 1% agarose gel. Non-amplified controls and size markers were also included. Three distinct bands of about 350 bp, 450 bp and 700 bp were observed. The three bands were blotted onto nitrocellulose paper and then hybridized to a synthetic radiolabeled DNA probe (probe C) corresponding to N-terminal amino acids 14 to 19 of the $NH_2$-terminal sequence disclosed in Example 2 (section 2.1 above) and having the following sequence:

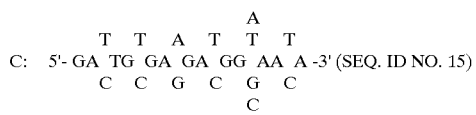

The three PCR products were found to hybridize with probe C under hybridization conditions of high stringency. However, the band corresponding to the 700 bp fragment was found to hybridize relatively poorly to the 350 bp and 450 bp fragments.

Following PCR amplification, the DNA was purified from the reaction mixture by chloroform and phenol extractions and ethanol precipitation. The DNA was then digested with EcoRI and HindIII and following gel purification, the fragments were subcloned into the large EcoRI-HindIII fragment of plasmid pSP65 (FIG. 4). The ligation mixture was used to transform *E. coli* strain MC1061. Transformants were screened by in-situ hybridization using the radiolabeled synthetic probe C disclosed above.

Plasmid DNA was prepared from positive clones. Those plasmids containing an EcoRI and HindIII fragment of the expected size were subjected to DNA sequencing using the Sanger dideoxy sequencing method. In this fashion two classes of clones were obtained: (A) those with an insert of about 290 base pairs (clones 3, 8 and 12) and (B) those with an insert of about 450 base pairs (clones 1, 4, 5 and 16). The plasmids of clones 3 and 4 were designated pSP65-XaI-3 and pSP65-XaI-4 respectively.

The DNA sequence and deduced amino acid sequence of clone pSP65-XaI-4 (clone 4) is shown in FIG. 5. In-vitro translation using wheat germ lysate showed that both classes of clones encode a protein of the same size. It might therefore be that the shorter nucleotide sequence (290 bp) of clone 3 is due to internal priming by a poly-A rich sequence at the 3' non-translating region of the mRNA encoded by DNA of clone 4 which was used as template in the reverse transcription reaction described at the beginning of this Example.

Example 4

Isolation and Cloning of DNA Encoding FXaI From a *Hirudo medicinalis* cDNA library The PCR derived cDNA disclosed in Example 3 (clones 3 and 4) was isolated by hybridization with a probe corresponding to the N-terminal sequence of the purified naturally occurring protein. The DNA of clone 4 was then used as a probe to screen a cDNA library of Hirudo medicinalis. The procedure is shown schematically in FIG. 6.

Total RNA was extracted from 120 leeches. Poly A+ mRNA was isolated from total RNA using the Fast Track™ mRNA isolation kit. An aliquot (4 µg) of the poly A+ mRNA so obtained was used for ds-cDNA (double stranded cDNA) synthesis using the ZAP™ cDNA synthesis kit (Stratagene).

The resulting cDNA was subcloned using the Stratagene Predigested Lambda Zap®II/EcoRI Cloning Kit. This kit which makes use of known methods of cloning provides for subcloning of the cDNA into lambda phage and amplification in E. coli. The phage is then isolated and the phagemid is excised with a helper phage. The resulting plasmids may be used for further manipulation by standard methods. 20 ng of the resulting ds-cDNA was digested with XhoI and EcoRI and subcloned into the XhoI and EcoRI digested Uni-ZAP™ vector. Upon plating of the resulting recombinant phage on E. coli XL1-Blue™, a cDNA library of about $1.5 \times 10^5$ plaques was obtained (FIG. 6). This cDNA library was screened for clones containing DNA encoding FXa inhibitor using as probe radiolabeled DNA from the PCR derived plasmid, pSP65-XaI-4 (Example 3) under hybridization conditions of both low and high stringency.

The prehybridization of the filter was carried out for 8 hours at 60° C. in 6×SSC, 0.1% SDS, 5×Denhardt and 100 µg/ml salmon sperm DNA, followed by hybridization with the radioactive probe for 48 hours at 60° C. Filters were washed at two different conditions: to obtain high stringency conditions, filters were washed with 0.2–0.5 ×SSC containing 0.2% SDS at 65° C. for two hours with several changes of solution; to obtain low stringency conditions, filters were washed with 2×SSC-0.2% SDS for 2 hours at 60° C. several times before autoradiography.

Positive plaques were picked, isolated and rescreened under the same hybridization conditions. Plasmid DNA of several positive clones was then prepared and sequenced by the Sanger dideoxy method.

The plasmid of one of the clones, obtained at low stringency, was designated pSK-XaI-13 (herein "clone 13" or "13") and selected for further manipulation and analysis. Other clones having different sequences were also obtained.

Clone 13 contains a nucleotide sequence substantially different from that of the PCR derived clone 4 and encodes a correspondingly different protein. The amino acid sequence encoded by clones 4 and 13 are compared in FIG. 3. The identification of clone 13 DNA by hybridization with clone 4 DNA was probably due to homology in the region of the predicted active site.

Clone 13 encodes a novel polypeptide of 155 amino acids (not including the N-terminal methionine) which contains 27 cysteine residues, five of which are located in a 22 amino acid putative extension peptide. The polypeptide product of clone 13 is herein designated "FXaI". The recombinant FXaI product of clone 13 is also termed Yagin.

The amino acid sequence of FXaI is thought to encompass a mature protein and a putative extension peptide. The putative extension peptide is so called because although it does not appear to be part of the mature protein (based on the alignment of cysteine residues of FXaI and other FXa inhibitors as disclosed below in Example 5: Alignment, and shown in FIG. 3), it does not have a composition typical of leader peptides, as discussed below.

We analyzed the N-terminal amino acid sequence of FXaI (FIG. 7) for the presence of a putative leader sequence. The analysis was carried out using the algorithm of Von Heijne (Nucleic Acids Res. 14: 4683–91, 1986). This algorithm predicts the probability of a given amino acid to occupy a certain position within a leader sequence and thus can determine whether the peptide sequence conforms with that of a leader sequence. Moreover, by determining the "combined amino acid score" along the peptide, the cleavage site between the leader sequence and the mature protein can also be predicted. When applied to the analysis of the N-terminal sequence of the product of plasmid pSP65-XaI-13, this algorithm failed to identify a pattern of amino acids consistent with that of a leader peptide and no cleavage site was found within the first 40 residues. Based on the above analysis, it can be concluded that the protein encoded by plasmid pSP65-XaI-13 lacks a leader sequence. Thus, the sequence, beginning with $met^1$ and ending with $cys^{22}$ or $glu^{23}$, appears to be an extension peptide and the sequence beginning with $glu^{23}$ or $val^{24}$ and ending with $lys^{156}$ appears to be the mature protein.

To be more specific, the polypeptide encoded by clone 13, as shown in FIG. 7 extends from $met^1$-$Lys^{156}$. The segment extending from $glu^{23}$ or $val^{24}$ through $cys^{109}$ may constitute the functional unit since it appears to be similar, including alignment of all the cysteines, to the sequences $tyr^{26}$-$gly^{110}$ of clone 4, and $cys^{10}$-$cys^{94}$ of antistasin, as shown in FIG. 3. The nature of the extension peptide containing the first 22 amino acids encoded by clone 13 is not presently known, and has therefore been designated as a putative extension peptide.

In order to confirm the existence of an open reading frame in clone 13, and to verify the size of the encoded polypeptide, the size of the polypeptide was determined using in vitro translation. SP6 RNA was prepared using the Stratagene in-vitro translation kit. The RNA thus obtained was subjected to in-vitro translation and the polypeptide products analyzed on SDS-PAGE under reducing conditions.

The polypeptide produced by in-vitro translation of mRNA encoded by clone 13 migrated on the gel at a position corresponding to about 20kD (which is identical to the molecular weight of FXaI expressed in E. coli). This observed molecular weight is considerably higher than the molecular weight calculated from the amino acid sequence. Without wishing to be bound by theory, it is postulated that this may in part be due to the numerous cysteines present in the sequence of the clone 13 polypeptides which can affect the migration of the protein on the gel.

Example 5

Comparison of deduced amino acid sequences

The deduced amino acid sequences of the PCR-derived FXa inhibitor cDNA, FXaI cDNA (clone 13 including the putative extension peptide) and antistasin were compared in different fashions i.e. maximum homology, identical homology, and alignment of cysteines.

I. Homology

Table 1 shows the degree of maximum homology of polypeptides (per cent) found using the 2020 PROSIS program (LKB), Version 6.00. Maximum homology is based on Needleman and Wunsch, J. Mol. Biol. 48:443 (1970) using the equivalence groups noted in the footnote to Table 1 and was determined on the full sequences including the putative extension peptides.

TABLE 1

| | Degree of maximum homology* | | |
|---|---|---|---|
| Clone | Antistasin | Clone 4 | Clone 13 |
| Antistasin | 100 | 50 | 48 |
| Clone 4 | 50 | 100 | 42 |
| Clone 13 | 48 | 42 | 100 |

*Maximum homology was determined using the following equivalence groups:
(1) A, S, T, P, G
(2) N, D, E, Q
(3) H, R, K
(4) M, L, I, V
(5) F, W, Y Table 2 shows the degree of identical homology (expressed as per cent) which is the homology obtained without equivalence groups.

TABLE 2

| | Degree of identical homology* | | |
|---|---|---|---|
| CLONE | Antistasin | Clone 4 | Clone 13 |
| Antistasin | 100 | 32 | 32 |
| Clone 4 | 32 | 100 | 29 |
| Clone 13 | 32 | 29 | 100 |

*Homology determined without equivalence groups

In the degrees of homology determined above, the complete sequence of the polypeptide encoded by clone 13 including the "extension" peptide, was taken into account.

II. Alignment

Another way to analyze the similarity of sequences is to align the cysteines in the sequence, even at the expense of homology. The computer program Pileup based on the work of Feng and Doolittle, J. Mol. Evol. 35:351–360 (1987) performs such alignment. The resulting alignment utilizing the parameters of gap weight 3.00 and gap length weight 0.10, for the same sequences compared above, is shown in FIG. 3. FIG. 3 shows that 14 cysteines can be aligned without introducing considerable gaps in any of the sequences. The Pileup program assigns a value on a scale of 0–1.5 expressing the degree of similarity of sequences. The resulting degree of similarity of the present sequences is shown in Table 3 as a percent of 1.5.

TABLE 3

| | Index of similarity | | |
|---|---|---|---|
| Clone | Clone 4 | Clone 13 | Antistasin |
| Clone 4 | 100 | 52 | 41 |
| Clone 13 | 52 | 100 | 34 |
| Antistasin | 41 | 34 | 100 |

It is thus seen that there is only little similarity between antistasin and the products of clone 4 and clone 13. This is shown both by comparison according to the degree of homology and according to the index of similarity.

Example 6: Expression of Recombinant FXaI

In order to obtain plasmids for the expression of recombinant FXaI in E. coli, further manipulation of the DNA fragments coding for the FXaI protein was required. Plasmid pSK-XaI-13 (Example 4) was digested with XhoI and EcoRI. The XhoI-EcoRI fragment containing FXaI was isolated and subcloned into a SalI-EcoRI digest of plasmid pSP65. The resulting plasmid was designated pSP65-XaI-13 (FIG. 8) and deposited in the ATCC under Accession No. 69134. This plasmid does not express the encoded protein; however, it may be used in the construction of expression plasmids.

By way of illustration, bacterial expression of recombinant FXaI encoded by clone 13 was obtained by using cDNA fragments to construct various plasmids.

A) Expression of mature ("m") recombinant FXaI under control of λP$_L$ or deo promoters In order to enable the expression of the mature ("m") FXaI polypeptide encoded by clone 13, an NdeI site containing the initiation codon ATG was introduced into the cDNA sequence adjacent to amino acid Val$^{24}$ by site directed mutagenesis using the following procedure:

An aliquot of plasmid pSP65-XaI-13 was digested with EcoRI and ClaI which cleaves within the FXaI coding region. A second aliquot of the same plasmid was digested with XmnI and ScaI which cleaves within the Amp$^R$ coding region. From both aliquots, the vector DNA was isolated, denatured and annealed in the presence of oligomer D

D:  5'- GAATTGCGAAGCATATGGTAATAGCAG -3' (SEQ. ID NO. 5)

followed by reaction with DNA polymerase Klenow fragment and ligation using T$_4$ DNA ligase (FIG. 9). The ligation mixture was used to transform E. coli MC1061. Clones resistant to ampicillin and positive in hybridization to radiolabeled oligomer D were identified. One such clone was designated pSP65-XaI-13"m".

Plasmid pSP65-XaI-13"m" is not an expression plasmid. In order to obtain expression, suitable regulatory elements were provided as follows. Plasmid pSP65-XaI-13"m" was digested with NdeI and HindIII. The NdeI-HindIII fragment coding for the FXaI polypeptide was isolated and ligated to the large fragment isolated from NdeI-HindIII digestion of the λP$_L$ expression vector pMAL-183/191 which contains the λP$_L$ and λcII ribosomal binding site. The resulting plasmid was designated pλ-XaI-13"m" (FIG. 10) and deposited in the ATCC under Accession No. 69135. Plasmid pλXaI-13"m" was used to transform E. coli 4300 which contains the thermolabile repressor cI$^{857}$. Upon induction at 42° C., the transformed cells were found to express a polypeptide having a molecular weight of about ~20kD.

The sequence of this polypeptide was designed to be that of clone 13 in FIG. 7 starting at Val$^{24}$ through Lys$^{156}$. A similar plasmid could be made by one skilled in the art by using plasmid pMLK-100 which has been deposited in E. coli 4300 under ATCC Accession No. 68605 which is similar to plasmid pMAL-183/191 in the regions containing the regulatory elements. Furthermore, one skilled in the art knows how to construct similar expression plasmids using other known and readily available vectors.

B) Expression of recombinant FXaI as a Fused Protein with 58 N-Terminal Amino Acids of Human Cu/Zn-SOD Plasmid pSP65-XaI-13 was digested with SspI and PstI. The SspI-PstI fragment encoding FXaI was isolated and ligated to the large fragment obtained from ScaI-PstI digestion of the SOD expression vector pBAST-R controlled by the deo promoter. The resulting plasmid was designated pDeo-S-XaI-13"f" (FIG. 11) and deposited in E. coli strain 733 in the ATCC under Accession No. 69137.

Plasmid pDeo-S-XaI-13"f" encodes a fusion protein containing a 58 amino acid fragment of a modified Cu/Zn-SOD sequence and the FXaI sequence of Ile$^{29}$ through Lys156 shown in FIG. 7. The modified Cu/Zn-SOD fragment has the following sequence:

MET ALA THR LYS ALA ALA SER VAL LEU LYS GLY ASP GLY PRO

VAL GLN GLY ILE ILE ASN PHE GLU GLN LYS GLU SER ASP GLY

PRO VAL LYS VAL TRP GLY SER ILE LYS GLY LEU THR GLU GLY

LEU HIS GLY PHE HIS VAL HIS GLU PHE GLY ASP ASN THR ALA

GLY SER (SEQ. ID NO. 16)

Plasmid pDeo-S-XaI-13"f" was used to transform *E. coli* strain 733. A fused SOD-FXaI recombinant protein having a molecular weight of about 21kD was obtained in the insoluble fraction following lysis of the cell pellet from a culture of the transformed cells.

C) Expression of FXaI as a Prepeptide Containing the Predicted Extension Peptide In order to facilitate the expression of FXaI, it was thought that inclusion of the putative extension peptide might enhance expression. Therefore, an NdeI site was introduced at Met$^3$ (FIG. 7) using PCR. For PCR site directed mutagenesis the following 5' and 3' end primers were used:

5' end primer I

5'- CCGAATT<u>CATATG</u>TGTTGGAACAAAGGT -3' (SEQ.ID NO. 6)
           NdeI

3' end primer J

5'- CC<u>AAGCTT</u>GGGCTGCAGGTCGA -3' (SEQ. ID NO. 7)
      HindIII

Plasmid pSP65-XaI-13 was processed by PCR amplification in the presence of primers I and J. The product was then digested with NdeI and HindIII. The fragment encoding FXaI was isolated and ligated to the large fragment obtained from NdeI-HindIII digestion of the λP$_L$ expression vector pMAL 183/191. The resulting plasmid was designated pλ-XaI-13"l" (FIG. 12). Plasmid pλ-XaI-13"l" was used to transform *E. coli* strain 4300. Following growth and induction of the transformed cells, FXaI was obtained from inclusion bodies found in the insoluble fraction after lysis of the cell pellet. The sequence of this polypeptide was designed to be that of the product of clone 13 in FIG. 7 including the extension peptide, starting at Lys$^2$ through Lys$^{156}$. It is not yet known if the N-terminal methionine (met$^1$) is present.

A similar plasmid could be made by one skilled in the art by using plasmid pMLK-100 which has been deposited in *E. coli* 4300 under ATCC Accession No. 68605 which is similar to plasmid pMAL-183/191 in the region containing the regulatory elements. Furthermore, one skilled in the art knows how to construct similar expression plasmids using other known and readily available vectors.

Example 7

Refolding and partial purification of recombinant FXaI produced by plasmid pλ-XaI-13"m"

A culture of *E. coli* 4300 containing plasmid pλ-XaI-13"m" was grown and induced essentially according to standard procedures known to those skilled in the art such as are disclosed in European Patent Publication No. 173,280, published Mar. 5, 1986. The culture was grown at 30° C.

until mid-log phase and then induced at 42° C. for 2 hours. The cells were pelleted and the cake stored frozen until processing.

1. Isolation of Inclusion Bodies

The bacterial cake was suspended in 10 volumes of buffer 1 (50 mM Tris-HCl pH 8 containing 10 mM EDTA). Cell disruption was performed by adding lysozyme (2500 U/ml) to the suspension and incubating with occasional stirring for 2 hours at room temperature. The suspension was then subjected to sonication (3×10 min), and centrifugation (12,000 rpm) for 30 min at 4° C. The supernatant was discarded and the pellet washed with detergent by resuspension in 10 volumes of buffer 1 containing 1% Nonidet P-40 (NP-40) and incubation with occasional stirring for 1 hour at room temperature. The pellet which was obtained by centrifugation (12,000 rpm) for 30 minutes at 4° C. was further washed with 10 volumes of distilled water, incubated with occasional stirring for 15 minutes at room temperature, and centrifuged (15,000 rpm) for 45 min at 4° C. The washing of the pellet resulted in removal of many of the *E. coli* proteins. It was established by SDS-PAGE that the recombinant FXaI polypeptide remained in the pellet under the conditions of washing.

2. Solubilization and reduction

Most of the FXaI polypeptide was found in the inclusion bodies, i.e., in the insoluble pellet obtained following cell disruption. The inclusion bodies were then solubilized in 20 volumes of 6M guanidinium chloride (GuCl) in buffer 2 (20 mM Tris-HCl pH 8 containing 1 mM EDTA and 100 mM NaCl). Reduction was initiated after 15 min by the addition of 10 mM reduced glutathione (GSH) under a stream of nitrogen and was allowed to proceed for 1 hour. The protein concentration was then adjusted to 1 mg/ml by the addition of buffer 2 containing GSH and further incubated for 1–3 hrs under nitrogen.

3. Refolding/reoxidation

The solubilized polypeptide so obtained which contains reduced FXaI was diluted up to ten-fold in buffer 2 (final GuCl and GSH concentrations 0.6M and 1 mM, respectively) to a protein concentration of 100 μg/ml protein. Oxidized glutathione (GSSG) was added to a final concentration of 0.1 mM and the solution was incubated for 16 h at 4° C. The oxidized protein was dialyzed with 3 buffer changes against buffer 2 lacking EDTA, before assaying its inhibitory activity in the chromogenic assay described in Example 2.

4. Inhibitory activity of various batches of refolded recombinant FXaI

Following dialysis, the refolded FXaI polypeptide was assayed for FXa inhibitory activity in the chromogenic assay described in Example 2. The results expressed in terms of milliunits (mu) per mg protein (mu/mg) are summarized in Table 4. The amount of protein causing 50% inhibition in an assay mixture containing 2 nM FXa is defined as 1 mu.

TABLE 4

Inhibition of FXa by Recombinant FXaI*
Refolded 13 "m" batch

| LG6X | LG4X | LG8X | LG5X[a] |
|------|------|------|---------|
| 160  | 267  | 179  | 41      |

*Specific activity, mu/mg
[a]Only partially refolded

In addition, the refolded polypeptide was also tested for its effect on thrombin, another coagulation cascade enzyme, which was assayed according to Lottenberg et al. Methods Enzymol. 80:341–361 (1981). No significant level of inhibition of thrombin by FXaI was observed (<1mu/mg).

In summary, the recombinant FXaI produced by the methods disclosed herein is biologically active. Furthermore, FXaI has been demonstrated to be selective towards FXa, since the inhibitory activity of FXaI towards FXa is approximately 200 fold greater than towards thrombin.

Example 8

Elicitation of Antibodies Against Naturally Occurring FXa Inhibitor, and Recombinant FXaI Antibodies were raised both against the SOD-FXaI fusion polypeptide described in Example 6, and against a naturally occurring FXa inhibitor isolated from DLS.

A. Preparation of antigens

1. Recombinant FXaI fusion protein

Antigen for immunization was prepared by expression of plasmid pDeo-S-XaI-13"f" (Example 6), in *E. coli* 733 grown overnight at 37° C. in LB containing 12.5 μg/ml tetracycline. The bacteria were pelleted by centrifugation, resuspended in 50 mM Tris-HCl pH 8 containing 1 mM EDTA and 50 μg/ml lysosyme, incubated for 30 minutes at room temperature, and sonicated twice for 5 minutes each time to reduce viscosity. Insoluble inclusion bodies containing the recombinant protein were collected by centrifugation. The pellet was resuspended in $H_2O$ and diluted with an equal volume of SDS-PAGE sample buffer (30% glycerol, 0.19M Tris-HCl pH 6.8, 10% SDS, 15% β-mercaptoethanol, and 0.004% bromphenol blue). The sample was then electrophoresed on a 12% SDS-PAGE gel, electro-transferred onto a nitrocellulose membrane, and stained with the reversible Ponceau stain. Protein having an apparent molecular weight of 29 kD, was extracted from the membrane and used as antigen for immunization.

2. Naturally occurring FXa inhibitor from DLS

Antigen for immunization was purified from DLS by Q-Sepharose and Heparin-Sepharose chromatography as described in Example 1. An aliquot of the protein was diluted with an equal volume of SDS-PAGE sample buffer (30% glycerol, 0.19M Tris-HCl pH 6.8, 10% SDS, 15% β-mercaptoethanol, and 0.004% bromphenol blue) The sample was then electrophoresed on a 15% SDS-PAGE gel, electro-transferred onto a nitrocellulose membrane, and stained with reversible Ponceau stain. Protein having an apparent molecular weight of about 14kD was extracted from the membrane, and used as antigen for immunization.

B. Elicitation of antibodies

Purified recombinant or naturally occurring antigen (20–60 μg), dissolved in 1 ml DMSO and mixed with complete Freund's adjuvant, was injected into the foot pads of a 1.8–2.3 kg rabbit. After 3 weeks, the rabbit was again injected, this time subcutaneously with the same amount of antigen mixed with incomplete Freund's adjuvant. This procedure was repeated twice more at the same interval.

In order to remove anti-SOD antibodies, expected to be present in the antiserum to the recombinant SOD-containing FXaI fusion protein, the antiserum was passed through an affinity column containing recombinant human Cu/Zn-SOD bound to Sepharose.

C. Antibody Verification by Western Blot Analysis

Antibodies were verified on a Western blot of various proteins run on a 12% SDS-PAGE run under reducing conditions. Following reaction with the antisera, the Western blots were developed with $^{125}$I-labeled protein A.

D. Results

Anti-13"f" antibody reacted with the 13"f" polypeptide and with the 13"m" polypeptide, but not with a recombinant protein having the amino acid sequence of the naturally occurring FXa inhibitor isolated from DLS.

Furthermore, antibodies against naturally occurring FXa inhibitor reacted with naturally occurring FXa inhibitor (isolated from DLS), but not with 13"m" (refolded and partially purified).

E. Conclusions

We have obtained two anti-sera: the purified anti-13"f" which contains antibodies against the 13"m" recombinant polypeptide derived from clone 13, and antiserum to a naturally occurring FXa inhibitor isolated from DLS. Based on the results with both antisera, we can deduce that there is no immunological cross-reaction between the naturally occurring FXa inhibitor isolated from DLS and the recombinant 13"m" FXaI polypeptide.

Therefore, these results clearly show that clone 13 encodes a protein which is substantially different from the naturally occurring FXaI protein, present in DLS.

F. Identification of naturally occurring FXaI in *H. medicinalis*

Since clone 13 was obtained from a cDNA library, it would reasonably be expected that the encoded protein should be present in DLS. However, using the anti-13"f" antibodies described above, no band was detected, even in the presence of a very high protein amount (70 kg).

Since no protein was detected in DLS by the assays described above, this novel FXaI may not be present in leech saliva. This would account for its not being observed in the course of purification of DLS.

However, the presence of a protein band with a molecular weight of about 20 kD which reacted on a Western blot with antibodies to the FXaI recombinant protein was demonstrated in supernatants of homogenized sections of the leech body. This confirmed the presence of the protein in the leech corresponding to the product of clone 13 (Yagin).

Example 9

Purification and Biological Activity of Refolded FXaI

Recombinant FXaI expressed by plasmid pλ-XaI-13 "m", produced and refolded essentially as described in Example 7 was purified to homogeneity and assayed for biological activity.

The refolded protein was purified by ultrafiltration on a 50K cutoff membrane, and further processed by Heparin-Sepharose and Q-Sepharose chromatography using NaCl gradients in 10 mM Tris-HCl pH 8. The activity peak eluted from Heparin-Sepharose at about 300 mM NaCl and was then loaded onto Q-Sepharose. The activity peak eluted from the Q-Sepharose at about 100 mM NaCl.

The purity of the protein so obtained was verified on SDS-PAGE under reducing conditions where it showed an apparent molecular weight of 20kD, and on Superose 12 gel filtration chromatography where it eluted with a retention time equivalent to about 15kD.

The purified FXaI had biochemical activity of about 2500 mu/mg in the chromogenic assay described in Example 2. The $K_i$ was determined to be about 13 nM in the chromogenic assay and 160 pM in the prothrombinase complex assay described in Example 2. The $IC_{50}$ was determined to be 20–40 nM in the chromogenic assay and about 540 pM in the prothrombinase assay.

APTT (activated partial thromboplastin time) of the purified protein was measured in human and murine plasma essentially as described in Spaethe, *Haemostasis,* AHS/Deutschland GmbH, Munich (1984), using as reagent Actin FS (Dade), which contains ellagic acid for activation of Factors XII and Factor XI, and soy bean phospholipid. Under these conditions, and in the presence of 20 mM $CaCl_2$, only the intrinsic pathway of coagulation is activated. The results showed that 23 nM (343 ng/ml) caused a doubling of the APTT in human plasma. In comparison, 50 nM heparin was required in the same assay to obtain the doubling of the APTT.

Biological experiments: Pharmacokinetic Study of FXaI

A preliminary pharmacokinetic experiment was performed in order to assess the clearance rate of FXaI from the circulatory system. Female Balb/c mice (20–25 gm body weight) were injected intravenously with purified FXaI. Blood samples were drawn into 1/10 v/v 3.8% citrate at 1, 3, 10 and 30 min after injection. The plasma was then separated and assayed for APTT. It was possible to obtain only one blood sample from each mouse and therefore each timepoint is from a different mouse. FXaI concentration was calculated from a calibration curve of APTT versus FXaI concentration which was constructed in vitro by adding various amounts of FXaI to a plasma pool from untreated mice. In this manner, the blood half-life was determined to be about 8.1 minutes.

Example 10

Mature FXaI Polypeptide Obtained from a Cleavable Fusion Protein

Low levels of expression of the mature FXaI polypeptide were obtained from plasmid pλ-XaI-13"m" (FIG. 10) as described in Example 6. Although plasmid pDeo-S-XaI-13"f" (FIG. 11) produced significant quantities of an FXaI fusion polypeptide as described in Example 6, it was not possible to obtain the 13"m" polypeptide, since there was no cleavage site between the SOD moiety and the FXaI moiety. In order to obtain larger quantities of the 13"m" polypeptide, a plasmid expressing a cleavable fusion polypeptide was constructed.

I. Construction of plasmid pλSOD-NGE-XaI-13"m"

The following procedures are shown schematically in FIGS. 13 and 2.

Plasmid pλ-XaI-13"l" (FIG. 12) was digested with SspI. The fragment encoding FXaI was isolated, further digested with AatII, and the large fragment isolated. Plasmid PBAST-R (FIG. 11) was digested with AatII and PpuMI and the large fragment isolated.

The AatII-SspI fragment containing the FXaI-encoding DNA was then ligated to the large pBAST-R fragment in the presence of the following two synthetic oligomers:

Oligomer K:

AsnGly
5'- GTCCTAATGGTGAAGTAATAGCAGAGAAT -3' (SEQ. ID NO. 8)

Oligomer L:

3'-      GATTACCACTTCATTATCGTCTCTTA -5' (SEQ. ID NO. 9)

The resulting plasmid, designated pDSOD-NGE-XaI-13"m" (FIG. 13), under control of the deo promoter, was used to transform *E. coli* 733, but was determined to be a poor expresser of the FXaI fusion protein.

In an attempt to obtain improved expression, a plasmid for expression of the FXaI fusion protein under control of the thermolabile λ $P_L$ promoter was constructed. Plasmid pDSOD-NGE-XaI-13"m" was digested with NdeI and HindIII. The small fragment containing the FXaI coding region was isolated and ligated to the large fragment isolated from NdeI-HindIII digestion of plasmid pλAB (FIG. 2). The resulting plasmid, designated pλSOD-NGE-XaI-13"m" (FIG. 2), under control of the $\lambda P_L$ promoter, was used to transform *E. coli* 4300 (F⁻), and was determined to be a good expresser of the FXaI fusion polypeptide.

Plasmid pλSOD-NGE-XaI-13"m" encodes in 5' to 3' order a fusion protein containing a 63 amino acid fragment of a modified Cu/Zn-SOD sequence, three amino acids Asn-Gly-Glu (containing the hydroxylamine cleavage site Asn-Gly), and the FXaI 13"m" polypeptide having the sequence $val^{24}$-$lys^{156}$ shown in FIG. 7. The SOD moiety has the following amino acid sequence:

| MET | ALA | THR | LYS | ALA | ALA | SER | VAL | LEU | LYS | GLY | ASP | GLY | PRO |
|---|---|---|---|---|---|---|---|---|---|---|---|---|---|
| VAL | GLN | GLY | ILE | ILE | ASN | PHE | GLU | GLN | LYS | GLU | SER | ASP | GLY |
| PRO | VAL | LYS | VAL | TRP | GLY | SER | ILE | LYS | GLY | LEU | THR | GLU | GLY |
| LEU | HIS | GLY | PHE | HIS | VAL | HIS | GLU | PHE | GLY | ASP | ASN | THR | ALA |
| GLY | SER | THR | SER | ALA | GLY | PRO, (SEQ. ID NO. 17). | | | | | | | |

II. Production of the 13"m" polypeptide from plasmid pμSOD-NGE-XaI-13"m"

*E. coli* 4300(F⁻) containing plasmid pXSOD-NGE-XaI-13"m" was grown at 30° C. till mid-log phase and then induced for two hours at 42° C. The FXaI fusion protein accumulated in inclusion bodies, which were isolated and washed as described in Example 7.

Washed inclusion bodies were solubilized in 20 volumes of nitrogen-flushed buffer 3 (20 mM Tris-HCl pH 8, 50 mM NaCl, 1 mM EDTA, and 20 mM GSH) containing 5.5M guanidinium thiocyanate (GuSCN). Following solubilization, the fusion protein was cleaved by incubation for 16 hours at room temperature at a concentration of 0.7 mg/ml in 1M hydroxylamine pH 9 (adjusted with LiOH) also containing 1.75M GuCl, 2.75M GuSCN, 10 mM Tris, 25 mM NaCl, 0.5M EDTA, and 10 mM GSH. After incubation, the solution was dialyzed against buffer 3 containing 3.5M GuCl.

The FXaI was then refolded by incubation at a concentration of 0.1 mg/ml in buffer 3 lacking GSH but containing 0.3 mM GSSG. The crude refolded protein so obtained inhibited FXa with specific activity of 150–300 mU/mg as determined by the chromogenic assay.

Example 11

Production of Recombinant FXaI in Eukaryotic Cells

Due to the inherent complexity of refolding a molecule containing many cysteines, such as FXaI, to obtain a biologically active polypeptide, it is postulated that production of the polypeptide in eucaryotic cells might eliminate of some of the difficulties. This would enable production of large amounts of properly refolded, biologically active recombinant protein.

In preliminary experiments, expression of the mature 13"m" FXaI polypeptide was obtained using a baculovirus expression system in Sf-9 insect cells (18). The cells had been transformed with DNA encoding the 13"l" protein, i.e. DNA encoding the FXaI polypeptide and its extension sequence (as contained in plasmid PSK-XaI-13 (FIG. 6)).

Western blot analysis showed that the resulting polypeptide accumulated in the insect cells and was neither processed nor secreted into the medium, consistent with the lack of a leader peptide (enabling secretion) at the N-terminus of the polypeptide (Example 4).

The polypeptide cross-reacted with antibodies to recombinant FXaI produced as described in Example 8.

Example 12

Improved expression plasmids and growth conditions for FXaI

A. Plasmid pλ-XaI-13"m"-$T_1T_2$

In order to eliminate overproduction of β-lactamase driven by the strong lambda $P_L$ promoter, a $T_1T_2$ transcription termination DNA fragment was introduced into plasmid pλ-XaI-13"m" (FIG. 10) resulting in plasmid pλ-XaI-13"m"-$T_1T_2$ (FIG. 26).

Plasmid pλ-XaI-13"m"-$T_1T_2$ was used to transform *E. coli* 4300, which contains the thermolabile repressor $cI^{857}$. Upon induction at 42° C., the transformed cells were found to express a polypeptide having a molecular weight of about 20kD at an expression level similar to that obtained with plasmid pλ-XaI-13"m". However, since there is no overproduction of β-lactamase protein, the percentage of protein which is FXaI in plasmid pλ-XaI-13"m"-$T_1T_2$ is higher than the percentage of protein which is FXaI in plasmid pλ-XaI-13"m".

B. Plasmid pλ-XaI-13"m" -05M-$T_1T_2$

Plasmid pλ-XaI-13"m"-05M (FIG. 14) was constructed in order to both improve the level of expression of FXaI and introduce an extra amino terminal amino acid, glycine, adjacent to the initiation codon ATG (encoding Met), which facilitates complete removal of the Met in the host bacteria following expression. The newly introduced Met-Gly is situated immediately before $Val^{24}$ in FIG. 7.

In order to eliminate overproduction of β-lactamase driven by the strong lambda $P_L$ promoter, a $T_1T_2$ transcription termination DNA fragment was introduced into plasmid pλ-XaI-13"m"-05M resulting in plasmid pλ-XaI-13"m"-05M-$T_1T_2$ (FIG. 15).

Plasmid pλ-XaI-13"m"-05M-$T_1T_2$ was used to transform *E. coli* 4300, which contains the thermolabile repressor $cI^{857}$. Upon induction at 42° C., the transformed cells were found to express a polypeptide having a molecular weight of about 20kD at an expression level two to three times higher than that of plasmid pλ-XaI-13"m".

C. Improved conditions for bacterial growth and Induction

The level of expression of FXaI from plasmids pλ-XaI-13"m"-$T_1T_2$ and pλ-XaI-13"m"-05M-$T_1T_2$ was low when using 1×LB supplemented with 0.1% glucose as growth medium.

To optimize growth and induction, a series of experiments was carried out. It was found that when using 5×LB supplemented with 0.1% glycerol as the growth medium and when changing the temperature of heat induction to 39° C. for 4 hours (instead of 42° C.), the level of expression of FXaI is several fold higher.

Example 13:

Improved production of pure and active FXaI

Refolding and purification of FXaI expressed by plasmid pλ-XaI-13"m"-$T_1T_2$ described in Example 12 was carried out as described in Examples 7 and 9 apart from the following changes in order to improve the production of FXaI.

Processing was scaled-up and the purity of the processed inclusion bodies was increased to 40% as evaluated by SDS-PAGE. Refolding and purification were scaled-up as shown in Scheme 1. The concentration of reducing agent, GSH, was increased from 10 mM to 20 mM. The Heparin-Sepharose column was replaced by a S-Sepharose column.

Concentration and dialysis were scaled-up and were performed on an ultrafiltration system, such as Pellicon (Millipore) or Production Ultrafiltration (PUF, Millipore) with a 10 kDa cutoff membrane, allowing completion of those steps within about 5 h.

In addition some other minor changes were made to the FXaI production protocol and all the improvements were incorporated into the improved production protocol, which is described in Scheme 1.

Scheme 1: FXaI expressed by plasmid pλ-XaI-13 "m"-$T_1T_2$ —
PROCESSING, REFOLDING AND PURIFICATION

| STEP | | |
| --- | --- | --- |
| BACTERIAL CAKE | Processing | Lysozyme digestion Gualin homogenizer, centrifugation; NP-40, centrifugation; water, centrifugation |
| INCLUSION BODIES | Dissolution, reduction | 16 L 6 M GuCl, 20 mM GSH, Buffer A. 1 H, RT |
| REDUCED PROTEIN | Refolding, reoxidation | 160 L 0.6 M GuCl, 2 mM GSH, 0.2 mM GSSG, Buffer A, 72 H, 4° C., 50 mcg/mL |
| | Concentration, dialysis, filtration | Pellicon (10 kDa) to 2.5 L; dialysis 10 mM Tris-HCl (pH8); filtration Cuno 30 |
| REFOLDED, ACTIVE FXaI | Purification | (1) Q-Sepharose 10 mM Tris-HCl (pH8); elution +250 mM NaCl (2) S-Sepharose 20 mM acetate (pH5); elution +400 mM NaCl |
| PURE, ACTIVE FXaI in PBS | | |

Buffer A: 20 mM Tris-HCl (pH8), 50 mM NaCl, 1 mM EDTA
PBS: 10 mM Na-phosphate (pH 7.4), 150 mM NaCl In summary, from 1.5 gram of bacterial cake, about 180 mg of FXaI (<95% pure) was produced.

Example 14

Characterization of FXaI

FXaI (produced as described in Example 13) was characterized as described below.

FXaI is a protein containing 133 amino acids beginning with val (val$^{24}$ in FIG. 7) with calculated molecular weight 15.4 kD. FXaI contains 22 cysteine residues, which are probably paired in 11 disulfide bonds.

1. Biochemical and stability properties

FXaI is a homogeneous protein, more than 95% pure as evaluated by SDS-PAGE under reducing conditions (Scheme 1). FXaI contains less than 1% dimers and aggregates as determined by gel filtration on Superose 12. The endotoxin levels as determined by the gel clot technique using Limulus amelocyte lysate (LAL) reagent (Yin, E. T. et al. (1972), Biochem. Biophys. Acta. 261: 284–289), are less than 4 EU/mg.

FXaI is stable in a lyophilized state, as well as in frozen form in PBS (preferably at −70° C.) at a protein concentration of 1–2 mg/ml (Bradford-SDS).

2. Inhibitory activity of FXaI

FXaI inhibits FXa and trypsin, but does not inhibit thrombin and plasmin.

(i) Inhibition of FXa

The FXa inhibitory activity of FXaI was tested in two assays:

(a) Inhibition of soluble FXa (15,000 mU/mg) was measured in an in vitro chromogenic assay (as described in Example 2). In this assay 1 mu is equivalent to the amount of material causing 50% inhibition in the assay, which contains 2 nM active FXa. The results of the assay are presented in Table 5 below. It is clear from this Table that FXaI is a high affinity inhibitor of FXa.

(b) Thrombin generation in the reconstituted prothrombinase complex assay (as described in Example 2) was inhibited as is shown in Table 5 below.

TABLE 5

FXaI inhibition of FXa in the chromogenic and reconstituted prothrombinase complex assays

| BATCH OF FXaI | Ki, nm | |
|---|---|---|
| | CHROMOGENIC ASSAY | PROTHROMBINASE ASSAY |
| 1 | 7.2 | 0.060 |
| 2 | 10.8 | 0.045 |
| 3 | 14.0 | 0.028 |

(ii) Inhibition of Trypsin

Inhibition of bovine trypsin by FXaI was calculated following the classical dose response method. Ki values were obtained by plotting the percentage of activity of FXaI (determined in the colorimetric assay described below) against the ratio of the concentrations of inhibitor and enzyme. The colorimetric assay was performed using 80 μM Chromozyme TH (Pentapharm, Switzerland) as substrate in 10 mM Tris-HCl, 10 mM Hepes (pH 7.8), 100 mM NaCl, 0.1% PEG 6000 at 25° C. in presence of 3.83 or 4.27 nM of bovine trypsin. Inhibitor and enzyme were preincubated for 10 min at 25° C. before adding the substrate. In this assay, the Ki values for two batches of FXaI were 7.6 and 6.0 nM.

(iii) Inhibition of Plasmin and Thrombin

Plasmin and thrombin were not inhibited by FXaI in a similar assay as that described above for trypsin. In the case of thrombin, the substrate used was the same as that used for trypsin; in the case of plasmin, S2251 (KabiVitrum, Sweden) was used as substrate.

3. Antibodies

Antibodies were raised against pure FXaI produced as described in Example 13.

(i) Elicitation of antibodies

Both refolded, intact FXaI (1.9 mg/ml) in phosphate buffered saline (PBS) and denatured FXaI (applied to 15% acrylamide SDS-PAGE transferred to nitrocellulose and solubilized in 0.5 ml DMSO), were injected into rabbits. Antigen (800 μg/ml) in PBS was mixed with an equal volume (0.5 ml) of Ribi adjuvant (Ribi adjuvant system—RAS—Ribi ImmunoCohem Research, Inc, Hamilton, MT, USA), whereas the DMSO solubilized antigen was injected into rabbit with the Ribi adjuvant without mixing. The antigen (1 ml) was administered to rabbits (2.5–4.5 kg) as follows: 0.05 ml intradermally in six sites; 0.2 ml intramuscularly into each hind leg; 0.1 ml subcutaneously in the neck region; and 0.2 ml intraperitoneally. Rabbits were injected every 28 days and test bled 10 days after injection. Booster injections were repeated ten times.

(ii) Antibody verification by Western Blot Analysis

Specificity of the antibodies was verified on a Western Blot of specific and unrelated proteins, run on a 12% SDS-PAGE gel under reducing conditions. Following reaction with antisera, a specifc reaction was detected using a non-radioactive light-based system (ECL system, Amersham International P/C, Amersham, England).

(iii) Results

The antibody against the refolded FXaI recognized both the refolded and denatured forms of FXaI, whereas the antibody against the reduced FXaI recognized reduced FXaI only. Neither antibody recognized unrelated proteins.

Example 15

Biological activity of FXaI

The experiments were performed with two batches of FXaI produced as described in Example 13.

I. In vitro APTT

FXaI-APTT dose response curves were constructed using plasma from man, mouse, rabbit, rat and baboon. FXaI concentrations of 1–3.3 μg/ml (Table 6), equivalent to 70–250 nM, caused a doubling of the APTT. Using rat plasma, the APTT doubling concentrations of heparin and low molecular weight heparin (LMWH) were 1.3 and 3.3 IU/ml, equivalent to 8.1 and 13.2 μg/ml, respectively.

II. Pharmacokinetics and pharmacodynamics of FXaI in various animals

As described below, pharmacokinetics and pharmacodynamics of FXaI were evaluated in mice, rats, rabbits and baboons. The pharmacokinetics were based on the rate of disappearance of radiolabeled FXaI from the plasma of the various animals, whereas pharmacodynamics were based on the time-dependent decrease of the ex vivo APTT.

(i) Pharmacokinetics

FXaI was iodinated ($^{125}$I) by reaction with the Bolton-Hunter reagent (Bolton and Hunter (1973), Biochem. J. 133: 529–539), admixed with unlabeled material (specific activity 0.13×10$^6$ cpm/μg) and injected into mice (10 μg/mouse). Analysis of plasma samples during 3 h revealed that the labeled material was fully TCA precipitable at all times and its level declined with a half-life (t½) of 41 minutes. Within 5 minutes after administration, about 40% of the radioactivity was found in the liver. The amount in the liver then decreased gradually in parallel with the amount in the plasma. Concomitantly, $^{125}$I-labeled material accumulated in the intestines, thus indicating that FXaI was probably degraded proteolytically in the liver, followed by excretion of the degraded products into the intestines. Labeled FXaI was additionally injected into rats and rabbits. In rats, the half-life of plasma radioactivity was about 76 min and in rabbits it was about 94 min (FIG. 16).

(ii) Pharmacodynamics

It was found that upon FXaI administration, ex vivo APTT is prolonged, relative to saline or PBS controls, in all animals studied. The APTT values decline in a time-dependent manner as FXaI is being cleared. These pharmacodynamic results are summarized in Table 6.

The pharmacodynamics of FXaI were additionally studied following i.p., s.c. and i.m. administration to mice. In these three routes of administration, the maximum APTT was achieved between 60–90 min, and the bioavailability was between 35–50%.

TABLE 6

FXaI concentration causing APTT doubling and biological Half-Life in Various Species

| Species | APTT Doubling Concentration ($\mu$g/ml) | Half-life (min) |
|---|---|---|
| Mouse | 1.2 | 78 |
| Rat | 2.2 | 61–92 |
| Rabbit | 1.7 | 70–78 |
| Baboon | 3.3 | >120 |
| Human | 1.0 | ND |

III. Anti-thrombotic activity in venous thrombosis model

The stainless steel coil-induced venous thrombus model in rats was used to study the inhibitory effect of FXaI on venous thrombus formation. The model employed was as described by Maffrand et al. [Thrombosis and Haemostasis 59: 225–230 (1988)].

Wistar-derived female rats (200–250 g) were anaesthetized by Ketamine HCl plus Xylazin HCl. A midline abdominal incision was made and the inferior vena cava was exposed. A stainless steel wire coil (a dental paste carrier, fine No. 31, 21 mm long) was inserted into the lumen of the vein, at the site just below the junction, and the incision was sutured. Each inserted device was individually weighed before insertion and each weight was recorded.

Subsequently, the rats were sacrificed. The segment of the vein carrying the coil was removed; the vein sections were incised longitudinally, and the coils carrying the thrombi were carefully removed and weighed. The initial weight of each coil was subtracted from its final weight.

Using this model, the anti-thrombotic activity of FXaI was compared with that of heparin. Mature clot formation within 2–3 hours is characteristic of this model. Hence, pharmacodynamic studies were performed using multiple i.v. injection regimens in order to attain a continuous plasma level of the anti-thrombotic agents. Plasma levels were estimated by ex vivo APTT measurements. It was found that satisfactory plasma profiles (±20%. fluctuations) were obtained with both heparin and FXaI by administration of an initial i.v. dose at 0-time, followed by two doses of 35% of the initial dose at 45 min intervals (FIG. 18). Using various dose levels in this regimen, clot formation was examined by insertion of the coils 5 min after the initial injection and clot measurements were taken 45 min after the third injection. ID50 is the dose of FXaI causing 50% decrease in the amount of clot formed. The anti-thrombotic effect seen with 2 doses of FXaI (compared to a PBS control) is shown in FIG. 19. These results were compared to the anti-thrombotic effect of heparin in this model, and are summarized in Table 7 below.

IV. Effect of FXaI and heparin on tail bleeding in mice

Bleeding time was measured in pentobarbitone anesthetized mice. Bleeding was induced by standardized transsection of the tips of the tails, and subaqueous bleeding time was determined after immediate vertical immersion of the tails in isotonic saline at 37° C.

This comparative study was done in order to evaluate the adverse effect, i.e., bleeding, of both FXaI and heparin. To assess this effect, tail bleeding time was determined in mice injected i.v. with FXaI and heparin, 5 min after injection. The prolongation of the bleeding time, i.e., the increase over control, for FXaI and heparin are shown in FIGS. 20 and 21 respectively.

V. Beneficial versus risk effects of FXaI and heparin.

Table 7 shows the doses required for a twofold prolongation of the bleeding time, as well as the ID50 values in the venous thrombosis model, for FXaI and heparin. The ratio between these two values is a direct measure of the relative benefit versus risk effects. For FXaI, this calculated ratio is 2.6, whereas heparin gave a value which was lower by one order of magnitude (0.2). In conclusion, FXaI was found to be a highly effective anti-thrombotic agent, with a superior benefit/risk ratio over that of heparin.

TABLE 7

Anti-thrombotic and bleeding parameters of FXaI and heparin

| | ANTI-THROMBOSIS (RAT COIL MODEL) | | BLEEDING TIME: | BENEFIT |
|---|---|---|---|---|
| AGENT | ID50 (a) | AVERAGE APTT (sec) (b) | TWOFOLD PROLONGATION DOSE (a) | /RISK RATIO (c) |
| FXaI | 67 $\mu$g/kg | 41 | 176 $\mu$g/kg | 2.6 |
| Heparin | 80 IU/kg (=500 $\mu$g/kg) | 63 | 17 IU/kg (=106 $\mu$g/kg) | 0.2 |

(a) Initial injected dose
(b) Ex-vivo APTT for the injected dose (control APTT = 29 sec)
(c) Ratio of the bleeding time doubling dose to the ID50

Example 16

Inhibition of Influenza Virus Propagation in Fertilized Chicken Eggs by FXaI

Establishment of the pharmacokinetic behavior of FXaI in fertilized chicken eggs The pharmacokinetic behavior of FXaI, produced as described in Example 13, in fertilized chicken eggs was determined by the time-dependent decrease of the ex vivo APTT. FXaI (300 $\mu$g/egg) was injected into the chorioallantoic fluid (CAF) of fertilized chicken eggs.

Aliquots of the CAF were removed at various time points and assayed for APTT prolongation in rat citrated plasma (3.8%, v/v 1:10). APTT prolongation activity was found to decrease by first-order kinetics, with a half-life of 24 hours. This finding served as a basis for adopting a 4-hour interval injection regimen in the virus propagation study.

Effect of FXaI on influenza virus propagation in fertilized eggs

Influenza virus type A (PR-8) was injected ($10^{-2}$ $EID_{50}$ in 0.1 ml saline per egg) into fertilized eggs. The eggs were divided into 3 groups. One group (Group A) was injected with FXaI (20 µg/egg) in 0.2 ml saline on 0-time, then 10 µg/egg (0.1 ml) at 4, 8, 12 and 16h post-injection. The second group (Group B) received FXaI (20 µg/egg) at 0-time, and another injection of 10 µg/egg at 4 h. The third group received 0.2 ml saline at 0-time followed by 0.1 ml saline at 4, 8, 12 and 16h, and served as a control. The eggs were maintained in a rolling mode at 37° C. At 24, 32 and 48 h post-injection, 4–10 eggs were taken from each group, the CAF removed and the levels of influenza virus examined in a hemagglutination assay (19). The results are presented in Table 8.

TABLE 8

Effect of FXaI on influenza virus titer in CAF of fertilized chicken eggs

| GROUP | VIRUS TITER ($log_2$ dilution) | | |
|---|---|---|---|
| | 24 h | 32 h | 48 h |
| Control | 5,3,4,0,0 | 0,8,5,7,8 | 6,6,6,6 |
| Group A (higher dose) | 0,0,0,0,0, 0,0,0,0,0 | 0,0,0,0,0 | 6,8,5,7,8 |
| Group B (lower dose) | 0,0,0,0,0 | 0,5,4,8,7 | 8,8,8,8 |

The results indicate that FXaI inhibits the propagation of the influenza virus in chicken embryonic cells.

In addition, these results indicate that FXaI inhibits influenza virus propagation in eukaryotes and will treat or prevent infection of subjects suffering from influenza virus or at risk of contracting influenza.

Example 17

Inhibition of acute arterial thrombosis by FXaI in the rat

The inhibitory effect of FXaI on acute arterial thrombosis was tested in an acute arterial thrombosis model in the rat. The model deployed was as decribed by Bernat, A., et al. [Thromb. Haemostas., 70, 812–816 (1993)] with slight modifications as described below.

Thrombus formation was induced by electrical stimulation of the carotid artery in rats. Wistar-derived male rats (250–350 g) were anaesthetized with Ketamine-HCl plus Xylazin-HCl and placed on a heated blanket. A segment of the right carotid artery (about 10 mm-long) was exposed and dissected free of surrounding tissue. A small piece of insulating film (Parafilm) and two stainless steel electrodes were inserted under the artery. Using a constant d.c. power supply, the artery was stimulated at 0.98 mA during 4 min. The thrombotic occlusion was monitored by measuring the local artery temperature cranially (downstream) from the site of electrical stimulation. Both body and arterial temperatures were measured at 20 min intervals over a 60 min period. An I.V. injection (0.5 ml) of saline (in control animals) or FXaI (at various concentrations) was administered to the rats 5 min before the onset of electrical stimulation.

The FXaI batch used in these experiments was produced as described in Example 13. However, even though this batch of FXaI had essentially the same activity in the chromogenic assay as previous batches of FXaI, it displayed only about 65% of their potency in the APTT assay, i.e., the concentration of FXaI causing doubling of the APTT was 50% higher than in the previous batches of FXaI.

The results for control animals (n=12) and three distinct doses of FXaI (0.133 mg/kg (n=7), 0.266 mg/kg (n=9) and 0.4 mg/kg (n=4)) are shown in FIG. 22. The results indicate that both higher doses of FXaI cause total abolition of the arterial thrombosis-associated temperature decrease, whereas the lowest dose displays a partial effect.

Example 18

Inhibition of thrombosis by FXaI in baboons

Inhibition of thrombus formation in baboons by FXaI produced as described in Example 13, was measured under conditions of variable blood shear rate using a dacron thrombogenic device that generates platelet-rich and fibrin-rich thrombi essentially as described in inter alia Cadroy et al., Blood 75(11): 2185–2193 (1990), Kelly et al. (1991), Blood 77: 1006–1012 and Cadroy et al. (1991), P.N.A.S. 88: 1177–1181 with some slight modifications as shown in FIG. 25.

Three baboons were each injected with three distinct doses of FXaI: 10, 40 and 200 µg/kg/hr. Half of the total dose was given as a bolus and the other half infused over one hour. The baboons were injected with In-platelets and their accumulation was measured by a gamma camera.

Steady state plasma levels were: undetectable at the lowest dose, 0.6 µg/ml at the intermediate dose, and 3.6 µg/ml at the high dose. The half-life of FXaI in the plasma of baboons is about two hours. Platelet deposition on the Dacron graft, representative of arterial thrombosis, was reduced by an average of 30%, 50% and 80% respectively by these doses (FIG. 23). In addition, each of these doses nearly abolished thrombus formation in the "Chamber" region of low-shear venous-type flow, representative of venous thrombosis (FIG. 24).

Furthermore, one baboon was injected with PBS and served as a control. In this baboon there was maximal level of arterial and venous platelet accumulation.

The results indicate that FXaI inhibits both venous thrombosis and arterial thrombosis in baboons. Moreover, the effect of FXaI on venous thrombosis can already be seen at the lowest concentration of FXaI (10 µg/kg/hr).

In addition, the amount of FXaI, needed to nearly abolish dacron arterial platelet deposition in baboons, is about two orders of magnitude smaller than the amount of desulfato-hirudin needed to obtain such an effect (Kelly et al. (1991), Blood 77: 1006–1012, especially FIG. 1C, 20 nmol desulfato-hirudin/kg/min≅7 mg hirudin/kg/hour). The amount of FXaI needed to abolish venous platelet deposition in baboons is also about two orders of magnitude smaller than the amount of H-peptide (Hirulog) needed to obtain such an effect (Cadroy et al.(1991), P.N.A.S. 88: 1177–1181, especially FIG. 1A).

Furthermore, the amount of FXaI, needed to nearly abolish dacron arterial platelet deposition in baboons, is about a fifth of the amount of Tick Anticoagulant Peptide (TAP) needed to obtain such an effect (Kelly et al., $65^{th}$ scientific sessions of the American Heart Association, New Orleans, La., USA, Nov. 16–19, 1992. Circulation 86 (4 suppl. 1) 1992, I-411.)

REFERENCES

1. Tuszynski et al., J. Biol. Chem 262:9718–9723 (1987)
2. EPO Publication No. 263,608, published Apr. 13, 1988, of Gasic et al, assigned to The Contributors to the Pennsylvania Hospital
3. Condra et al., Thromb. Haemostas. 61:437–441 (1989)
4. U.S. Pat. No. 4,832,849, May 23, 1989, of Cardin, assigned to Merril Dow Pharmaceuticals 5. European Patent Application Publication No. 419,099, Vlasuk, et al., Mar. 27, 1991
6. Teitel et al., J. Clin. Invest. 71:1383–1391 (1983)
7. Dunwiddie et al., Thromb. Haemostas. 67:371–376 (1992)
8. Dunwiddie et al., J. Biol. Chem. 264:16694–16699 (1989)
9. Waxman et al., Science 248:593–596 (1990)
10. Neeper et al., J. Biol. Chem. 265:17746- (1990)
11. Jacobs, Thromb. Haemostas. 64:235–238 (1990)
12. Vlasuk et al., Thromb. Haemostas. 65:257–269 (1991)
13. U.S. Pat. No. 5,196,335, issued May 23, 1993, Rigbi et al. assigned to Yissum Research Development Co.
14. Hirsh, Drug Therapy 324:1565–1574 (1991)
15. Gold, N. Eng. J. of Med. 323:1483–1485 (1990)
16. Weitz, et al., J. Clin. Invest. 86:385–391 (1990)
17. Sitko, et al., Circulation 85:805–815 (1992)
18. Neutra, et al., Appl. Microbiol. Biotechnol 37:74–78 (1992)
19. Purchare et al. (1987), A laboratory manual for the isolation and identification of avian pathogens, Third Edition, American Association of Avian Pathalogists. 194.

What is claimed is:

1. A polypeptide comprising the amino acid sequence

X— Y— CYS GLN GLU GLU GLU CYS PRO ASP PRO TYR LEU CYS SER

PRO VAL THR ASN ARG CYS GLU CYS THR PRO VAL LEU CYS ARG MET

TYR CYS LYS PHE TRP ALA LYS ASP GLU LYS GLY CYS GLU ILE CYS

LYS CYS GLU GLU LEU CYS GLN ASN GLN ASN CYS THR LYS ASP MET

LEU CYS SER SER VAL THR ASN ARG CYS ASP CYS GLN ASP PHE LYS

CYS PRO GLN SER TYR CYS —Z wherein X is MET or absent;
Y is 0–29 amino acids of the sequence LYS MET CYS TRP ASN LYS GLY CYS PRO CYS GLY GLN ARG CYS ASN LEU HIS ARG ASN GLU CYS GLU VAL ILE ALA GLU ASN ILE GLU, with the proviso that if Y is more than 0 amino acids then the carboxy-terminal Glu of Y is present and wherein $Val^{24}$ may be preceded by Gly; and Z is absent or all or a part of the sequence $Pro^{110}$-$Lys^{156}$ shown in FIG. 7 (SEQ ID NO. 24), with the proviso that if Z is more than 0 amino acids then the amino-terminal Pro of Z is present.

2. A polypeptide according to claim 1 having the amino acid sequence X-$Lys^2$-$Lys^{156}$ where $Lys^2$-$Lys^{156}$ is identical to the sequence shown in FIG. 7 (SEQ ID NO. 24) and wherein X is MET or absent.

3. A polypeptide according to claim 1 comprising the amino acid sequence X-Ile$^{29}$-Lys$^{156}$ where Ile$^{29}$-Lys$^{156}$ is identical to the sequence shown in FIG. 7 (SEQ ID NO. 24) and wherein X is MET or absent.

4. A polypeptide according to claim 1 having the amino acid sequence X-Val$^{24}$-Lys$^{156}$ where Val$^{24}$-Lys$^{156}$ is identical to the sequence shown in FIG. 7 (SEQ ID NO. 24), and wherein X is MET or absent and wherein Val$^{24}$ may be preceded by Gly.

5. A non-glycosylated polypeptide of any of claims 1–4.

6. A polypeptide of claim 1, 2, 3, 4 or 5 having Factor Xa inhibitory activity.

7. A polypeptide according to claim 1 having the amino acid sequence Glu$^{23}$-Lys$^{156}$ where Glu$^{23}$-Lys$^{156}$ is identical to the sequence shown in FIG. 7 (SEQ ID NO. 24).

8. A non-glycosylated polypeptide of claim 7.

9. A composition comprising the polypeptide of any of claims 1–4 and 7 in an amount effective to obtain reduction of blood coagulation resulting from the biological activity of the polypeptide, and a suitable carrier.

* * * * *

SEQUENCE LISTING ( 1 ) GENERAL INFORMATION:

( i i i ) NUMBER OF SEQUENCES: 25

( 2 ) INFORMATION FOR SEQ ID NO:1:

( i ) SEQUENCE CHARACTERISTICS:
        ( A ) LENGTH: 79 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( i x ) FEATURE:
        ( A ) NAME/KEY: Peptide
        ( B ) LOCATION: 1..79

( x i ) SEQUENCE DESCRIPTION: SEQ ID NO:1:

```
Cys Gln Glu Glu Glu Cys Pro Asp Pro Tyr Leu Cys Ser Pro Val Thr
 1               5                  10                  15
Asn Arg Cys Glu Cys Thr Pro Val Leu Cys Arg Met Tyr Cys Lys Phe
             20                  25                  30
Trp Ala Lys Asp Glu Lys Gly Cys Glu Ile Cys Lys Cys Glu Glu Leu
         35                  40                  45
Cys Gln Asn Gln Asn Cys Thr Lys Asp Met Leu Cys Ser Ser Val Thr
     50                  55                  60
Asn Arg Cys Asp Cys Gln Asp Phe Lys Cys Pro Gln Ser Tyr Cys
 65                  70                  75
```

( 2 ) INFORMATION FOR SEQ ID NO:2:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( i x ) FEATURE:
        ( A ) NAME/KEY: Peptide
        ( B ) LOCATION: 1..29

( x i ) SEQUENCE DESCRIPTION: SEQ ID NO:2:

```
Lys  Met  Cys  Trp  Asn  Lys  Gly  Cys  Pro  Cys  Gly  Gln  Arg  Cys  Asn  Leu
 1              5                    10                        15
His  Arg  Asn  Glu  Cys  Glu  Val  Ile  Ala  Glu  Asn  Ile  Glu
            20                    25
```

(2) INFORMATION FOR SEQ ID NO:3:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:3:

AACTCGAGGA TCCAAGCTTT TTTTTTTTTT TT        32

(2) INFORMATION FOR SEQ ID NO:4:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:4:

CCGAATTCAT ATGTAYGARG TNATNTAYGT NGAYGAYCC        39

(2) INFORMATION FOR SEQ ID NO:5:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:5:

GAATTGCGAA GCATATGGTA ATAGCAG        27

(2) INFORMATION FOR SEQ ID NO:6:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:6:

CCGAATTCAT ATGTGTTGGA ACAAAGGT                                                                  28

( 2 ) INFORMATION FOR SEQ ID NO:7:

( i ) SEQUENCE CHARACTERISTICS:
          ( A ) LENGTH: 22 base pairs
          ( B ) TYPE: nucleic acid
          ( C ) STRANDEDNESS: single
          ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:7:

CCAAGCTTGG GCTGCAGGTC GA                                                                        22

( 2 ) INFORMATION FOR SEQ ID NO:8:

( i ) SEQUENCE CHARACTERISTICS:
          ( A ) LENGTH: 29 base pairs
          ( B ) TYPE: nucleic acid
          ( C ) STRANDEDNESS: single
          ( D ) TOPOLOGY: linear ( i i ) MOLECULE TYPE: DNA (genomic)

( i i i ) HYPOTHETICAL: YES ( i v ) ANTI-SENSE: YES ( x i ) SEQUENCE DESCRIPTION: SEQ ID NO:8:

GTCCTAATGG TGAAGTAATA GCAGAGAAT                                                                 29

( 2 ) INFORMATION FOR SEQ ID NO:9:

( i ) SEQUENCE CHARACTERISTICS:
          ( A ) LENGTH: 26 base pairs
          ( B ) TYPE: nucleic acid
          ( C ) STRANDEDNESS: single
          ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:9:

ATTCTCTGCT ATTACTTCAC CATTAG                                                                    26

( 2 ) INFORMATION FOR SEQ ID NO:10:

( i ) SEQUENCE CHARACTERISTICS:
          ( A ) LENGTH: 22 base pairs
          ( B ) TYPE: nucleic acid
          ( C ) STRANDEDNESS: single
          ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:10:

TATGGGTGTA ATAGCAGAGA AT                                                                        22

( 2 ) INFORMATION FOR SEQ ID NO:11:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:11:

ATTCTCTGCT ATTACACCCA    20

( 2 ) INFORMATION FOR SEQ ID NO:12:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:12:

Tyr Glu Val Ile Tyr Val Asp Asp Pro Cys Glu Asp Ser Asp Cys Glu
1             5                  10               15

Asp Gly Asn Lys
          20

( 2 ) INFORMATION FOR SEQ ID NO:13:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:13:

Tyr Glu Val Ile Tyr Val Asp Asp Pro Cys Glu Asp Ser Asp Cys Glu
1             5                  10               15

Asp Gly Asn Lys
          20

( 2 ) INFORMATION FOR SEQ ID NO:14:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO (iv) ANTI-SENSE: NO (v) FRAGMENT TYPE: N-terminal (xi) SEQUENCE DESCRIPTION: SEQ ID NO:14:

Tyr Glu Val Ile Tyr Val Asp Asp Pro
1               5

(2) INFORMATION FOR SEQ ID NO:15:

(i) SEQUENCE CHARACTERISTICS:
    (A) LENGTH: 19 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:15:

GAYTGYGARG AYGGNAAYA                                                                              19

(2) INFORMATION FOR SEQ ID NO:16:

(i) SEQUENCE CHARACTERISTICS:
    (A) LENGTH: 58 amino acids
    (B) TYPE: amino acid
    (C) STRANDEDNESS: single
    (D) TOPOLOGY: linear (ii) MOLECULE TYPE: protein (iii) HYPOTHETICAL: NO (iv) ANTI-SENSE: NO (v) FRAGMENT TYPE: N-terminal (ix) FEATURE:
    (A) NAME/KEY: Protein
    (B) LOCATION: 1..58

(xi) SEQUENCE DESCRIPTION: SEQ ID NO:16:

Met Ala Thr Lys Ala Ala Ser Val Leu Lys Gly Asp Gly Pro Val Gln
1               5                   10                  15

Gly Ile Ile Asn Phe Glu Gln Lys Glu Ser Asp Gly Pro Val Lys Val
            20                  25                  30

Trp Gly Ser Ile Lys Gly Leu Thr Glu Gly Leu His Gly Phe His Val
        35                  40                  45

His Glu Phe Gly Asp Asn Thr Ala Gly Ser
        50                  55

(2) INFORMATION FOR SEQ ID NO:17:

(i) SEQUENCE CHARACTERISTICS:
    (A) LENGTH: 63 amino acids
    (B) TYPE: amino acid
    (C) STRANDEDNESS: single
    (D) TOPOLOGY: linear (ii) MOLECULE TYPE: protein (iii) HYPOTHETICAL: NO (iv) ANTI-SENSE: NO (v) FRAGMENT TYPE: N-terminal ( i x ) FEATURE:
    ( A ) NAME/KEY: Protein
    ( B ) LOCATION: 1..63

( x i ) SEQUENCE DESCRIPTION: SEQ ID NO:17:

| Met | Ala | Thr | Lys | Ala | Ala | Ser | Val | Leu | Lys | Gly | Asp | Gly | Pro | Val | Gln |
|---|---|---|---|---|---|---|---|---|---|---|---|---|---|---|---|
| 1 | | | | 5 | | | | | 10 | | | | | 15 | |
| Gly | Ile | Ile | Asn | Phe | Glu | Gln | Lys | Glu | Ser | Asp | Gly | Pro | Val | Lys | Val |
| | | | 20 | | | | | 25 | | | | | 30 | | |
| Trp | Gly | Ser | Ile | Lys | Gly | Leu | Thr | Glu | Gly | Leu | His | Gly | Phe | His | Val |
| | | 35 | | | | | 40 | | | | | 45 | | | |
| His | Glu | Phe | Gly | Asp | Asn | Thr | Ala | Gly | Ser | Thr | Ser | Ala | Gly | Pro | |
| | | 50 | | | | | 55 | | | | | 60 | | | |

( 2 ) INFORMATION FOR SEQ ID NO:18:

( i ) SEQUENCE CHARACTERISTICS:
        ( A ) LENGTH: 85 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( i x ) FEATURE:
        ( A ) NAME/KEY: Protein
        ( B ) LOCATION: 1..85

( x i ) SEQUENCE DESCRIPTION: SEQ ID NO:18:

| Tyr | Glu | Val | Met | Tyr | Val | Asp | Asp | Pro | Cys | Glu | Asp | Ser | Asp | Cys | Glu |
|---|---|---|---|---|---|---|---|---|---|---|---|---|---|---|---|
| 1 | | | | 5 | | | | | 10 | | | | | 15 | |
| Asp | Gly | Asn | Lys | Cys | Ser | Pro | Val | Thr | Asn | Glu | Cys | Asp | Cys | Ser | Pro |
| | | | 20 | | | | | 25 | | | | | 30 | | |
| Val | Arg | Cys | Arg | Leu | His | Cys | Asn | Phe | Tyr | Val | Lys | Asp | Ser | Asn | Gly |
| | | | 35 | | | | | 40 | | | | | 45 | | |
| Cys | Glu | Thr | Cys | Ala | Cys | Glu | Pro | Lys | Cys | Lys | His | Lys | Asn | Cys | Ser |
| | | 50 | | | | | 55 | | | | | 60 | | | |
| Thr | Gly | His | His | Cys | Asn | Lys | Leu | Thr | Asn | Lys | Cys | Glu | Leu | Lys | Lys |
| 65 | | | | | 70 | | | | | 75 | | | | | 80 |
| Gln | Arg | Arg | Met | Gly | | | | | | | | | | | |
| | | | | 85 | | | | | | | | | | | |

( 2 ) INFORMATION FOR SEQ ID NO:19:

( i ) SEQUENCE CHARACTERISTICS:
        ( A ) LENGTH: 155 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( i x ) FEATURE:
        ( A ) NAME/KEY: Protein
        ( B ) LOCATION: 1..155

( x i ) SEQUENCE DESCRIPTION: SEQ ID NO:19:

| Lys | Met | Cys | Trp | Asn | Lys | Gly | Cys | Pro | Cys | Gly | Gln | Arg | Cys | Asn | Leu |
|---|---|---|---|---|---|---|---|---|---|---|---|---|---|---|---|
| 1 | | | | 5 | | | | | 10 | | | | | 15 | |

| His | Arg | Asn | Glu | Cys | Glu | Val | Ile | Ala | Glu | Asn | Ile | Glu | Cys | Gln | Glu |
|---|---|---|---|---|---|---|---|---|---|---|---|---|---|---|---|
| | | | 20 | | | | | 25 | | | | | 30 | | |

| Glu | Glu | Cys | Pro | Asp | Pro | Tyr | Leu | Cys | Ser | Pro | Val | Thr | Asn | Arg | Cys |
|---|---|---|---|---|---|---|---|---|---|---|---|---|---|---|---|
| | | 35 | | | | | 40 | | | | | 45 | | | |

| Glu | Cys | Thr | Pro | Val | Leu | Cys | Arg | Met | Tyr | Cys | Lys | Phe | Trp | Ala | Lys |
|---|---|---|---|---|---|---|---|---|---|---|---|---|---|---|---|
| | 50 | | | | | 55 | | | | | 60 | | | | |

| Asp | Glu | Lys | Gly | Cys | Glu | Ile | Cys | Lys | Cys | Glu | Glu | Leu | Cys | Gln | Asn |
|---|---|---|---|---|---|---|---|---|---|---|---|---|---|---|---|
| 65 | | | | | 70 | | | | | 75 | | | | | 80 |

| Gln | Asn | Cys | Thr | Lys | Asp | Met | Leu | Cys | Ser | Ser | Val | Thr | Asn | Arg | Cys |
|---|---|---|---|---|---|---|---|---|---|---|---|---|---|---|---|
| | | | | 85 | | | | | 90 | | | | | 95 | |

| Asp | Cys | Gln | Asp | Phe | Lys | Cys | Pro | Gln | Ser | Tyr | Cys | Pro | His | Gly | Phe |
|---|---|---|---|---|---|---|---|---|---|---|---|---|---|---|---|
| | | | 100 | | | | | 105 | | | | | 110 | | |

| Glu | Thr | Asp | Glu | Asn | Glu | Cys | Glu | Val | Cys | Ile | Cys | Lys | Lys | Pro | Thr |
|---|---|---|---|---|---|---|---|---|---|---|---|---|---|---|---|
| | | | 115 | | | | | 120 | | | | | 125 | | |

| Cys | Ala | Asn | Cys | Gly | Lys | Thr | Thr | Lys | Lys | Pro | Arg | Thr | Ile | Asp | Arg |
|---|---|---|---|---|---|---|---|---|---|---|---|---|---|---|---|
| | | 130 | | | | | 135 | | | | | 140 | | | |

| Leu | Lys | Asn | Trp | Phe | Lys | Lys | Phe | Gly | Lys |
|---|---|---|---|---|---|---|---|---|---|
| 145 | | | | | 150 | | | | 155 |

( 2 ) INFORMATION FOR SEQ ID NO:20:

( i ) SEQUENCE CHARACTERISTICS:
        ( A ) LENGTH: 119 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( i x ) FEATURE:
        ( A ) NAME/KEY: Protein
        ( B ) LOCATION: 1..119

( x i ) SEQUENCE DESCRIPTION: SEQ ID NO:20:

| Glu | Gly | Pro | Phe | Gly | Pro | Gly | Cys | Glu | Glu | Ala | Gly | Cys | Pro | Glu | Gly |
|---|---|---|---|---|---|---|---|---|---|---|---|---|---|---|---|
| 1 | | | | 5 | | | | | 10 | | | | | 15 | |

| Ser | Ala | Cys | Asn | Ile | Ile | Thr | Asp | Arg | Cys | Thr | Cys | Ser | Gly | Val | Arg |
|---|---|---|---|---|---|---|---|---|---|---|---|---|---|---|---|
| | | | 20 | | | | | 25 | | | | | 30 | | |

| Cys | Arg | Met | His | Cys | Pro | His | Gly | Phe | Gln | Arg | Ser | Arg | Tyr | Gly | Cys |
|---|---|---|---|---|---|---|---|---|---|---|---|---|---|---|---|
| | | 35 | | | | | 40 | | | | | 45 | | | |

| Glu | Phe | Cys | Lys | Cys | Arg | Leu | Glu | Pro | Met | Lys | Ala | Thr | Cys | Asp | Ile |
|---|---|---|---|---|---|---|---|---|---|---|---|---|---|---|---|
| | 50 | | | | | 55 | | | | | 60 | | | | |

| Ser | Glu | Cys | Pro | Glu | Gly | Met | Met | Cys | Ser | Arg | Leu | Thr | Asn | Lys | Cys |
|---|---|---|---|---|---|---|---|---|---|---|---|---|---|---|---|
| 65 | | | | | 70 | | | | | 75 | | | | | 80 |

| Asp | Cys | Lys | Ile | Asp | Ile | Asn | Cys | Arg | Lys | Thr | Cys | Pro | Asn | Gly | Leu |
|---|---|---|---|---|---|---|---|---|---|---|---|---|---|---|---|
| | | | | 85 | | | | | 90 | | | | | 95 | |

| Lys | Arg | Asp | Lys | Leu | Gly | Cys | Glu | Tyr | Cys | Glu | Cys | Arg | Pro | Lys | Arg |
|---|---|---|---|---|---|---|---|---|---|---|---|---|---|---|---|
| | | | 100 | | | | | 105 | | | | | 110 | | |

| Lys | Leu | Ile | Pro | Arg | Leu | Ser |
|---|---|---|---|---|---|---|
| | | | 115 | | | |

( 2 ) INFORMATION FOR SEQ ID NO:21:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:21:

TTTTTCGAAC CTAGG                         15

( 2 ) INFORMATION FOR SEQ ID NO:22:

( i ) SEQUENCE CHARACTERISTICS:
        ( A ) LENGTH: 148 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( i x ) FEATURE:
        ( A ) NAME/KEY: Protein
        ( B ) LOCATION: 1..148

( x i ) SEQUENCE DESCRIPTION: SEQ ID NO:22:

```
Met Tyr Glu Val Met Tyr Val Asp Asp Pro Cys Glu Asp Ser Asp Cys
 1               5                  10                  15

Glu Asp Gly Asn Lys Cys Ser Pro Val Thr Asn Glu Cys Asp Cys Ser
            20                  25                  30

Pro Val Arg Cys Arg Leu His Cys Asn Phe Tyr Val Lys Asp Ser Asn
            35                  40                  45

Gly Cys Glu Thr Cys Ala Cys Glu Pro Lys Cys Lys His Lys Asn Cys
        50                  55                  60

Ser Thr Gly His His Cys Asn Lys Leu Thr Asn Lys Cys Glu Leu Lys
65                      70                  75                  80

Lys Gln Arg Arg Met Gly Thr Lys Ile Lys Lys Arg Lys Lys Leu Arg
                85                  90                  95

Lys Lys Asp Ser Leu Glu Ile Leu Arg Ile Ser Asn Ile Leu Thr Tyr
                100                 105                 110

Leu Phe Val Val Pro Leu Ile Asn Met Val Ser Ile Asn Ile Glu Glu
            115                 120                 125

Glu Leu Tyr Phe Ile Val Arg Ile Ser Thr Phe Lys Met Ser Lys Lys
            130                 135                 140

Lys Lys Lys Lys
145
```

( 2 ) INFORMATION FOR SEQ ID NO:23:

( i ) SEQUENCE CHARACTERISTICS:
        ( A ) LENGTH: 469 base pairs
        ( B ) TYPE: nucleic acid (C) STRANDEDNESS: single
(D) TOPOLOGY: linear (i i) MOLECULE TYPE: DNA (genomic)

(i i i) HYPOTHETICAL: NO (i v) ANTI-SENSE: NO (v) FRAGMENT TYPE: N-terminal (x i) SEQUENCE DESCRIPTION: SEQ ID NO:23:

| | | | | | |
|---|---|---|---|---|---|
| GGAATTCATA | TGTATGAGGT | GATGTATGTG | GACGATCCAT | GTGAGGATTC | AGACTGTGAA | 60 |
| GATGGAAACA | AATGCAGTCC | TGTGACCAAT | GAATGCGATT | GCTCTCCTGT | GCGATGCAGA | 120 |
| TTGCATTGCA | ATTTTTACGT | CAAAGACAGT | AATGGCTGTG | AGACATGCGC | TTGTGAGCCT | 180 |
| AAATGCAAGC | ATAAAAATTG | TTCAACTGGC | CATCACTGCA | ACAAATTGAC | AAACAAGTGT | 240 |
| GAATTAAAAA | AGCAACGAAG | AATGGGATAG | ACCAAAATAT | AAAAAAAAAG | AAAGAAGCTG | 300 |
| AGAAAAAAAG | ATTCCCTGGA | GATTCTCTGA | CGATAAATTA | GCAACATATT | GACTTACTTA | 360 |
| TTCGTAGTTC | CGTTAATAAA | CATGGTTTCC | TAAATAAATA | TTGAAGAAGA | ACTATATTTT | 420 |
| ATTGTTCGCA | TATCAACATT | CAAAATGTCA | AAAAAAAAAA | AAAAAAAA | | 469 |

(2) INFORMATION FOR SEQ ID NO:24:

(i) SEQUENCE CHARACTERISTICS:
(A) LENGTH: 197 amino acids
(B) TYPE: amino acid
(C) STRANDEDNESS: single
(D) TOPOLOGY: linear (i i) MOLECULE TYPE: protein (i i i) HYPOTHETICAL: NO (i v) ANTI-SENSE: NO (v) FRAGMENT TYPE: N-terminal (i x) FEATURE:
(A) NAME/KEY: Protein
(B) LOCATION: 1..197

(x i) SEQUENCE DESCRIPTION: SEQ ID NO:24:

| Met | Lys | Met | Cys | Trp | Asn | Lys | Gly | Cys | Pro | Cys | Gly | Gln | Arg | Cys | Asn |
|---|---|---|---|---|---|---|---|---|---|---|---|---|---|---|---|
| 1 | | | | 5 | | | | | 10 | | | | | 15 | |

| Leu | His | Arg | Asn | Glu | Cys | Glu | Val | Ile | Ala | Glu | Asn | Ile | Glu | Cys | Gln |
|---|---|---|---|---|---|---|---|---|---|---|---|---|---|---|---|
| | | | | 20 | | | | 25 | | | | | 30 | | |

| Glu | Glu | Glu | Cys | Pro | Asp | Pro | Tyr | Leu | Cys | Ser | Pro | Val | Thr | Asn | Arg |
|---|---|---|---|---|---|---|---|---|---|---|---|---|---|---|---|
| | | 35 | | | | | 40 | | | | | 45 | | | |

| Cys | Glu | Cys | Thr | Pro | Val | Leu | Cys | Arg | Met | Tyr | Cys | Lys | Phe | Trp | Ala |
|---|---|---|---|---|---|---|---|---|---|---|---|---|---|---|---|
| | | 50 | | | | | 55 | | | | | 60 | | | |

| Lys | Asp | Glu | Lys | Gly | Cys | Glu | Ile | Cys | Lys | Cys | Glu | Glu | Leu | Cys | Gln |
|---|---|---|---|---|---|---|---|---|---|---|---|---|---|---|---|
| 65 | | | | | 70 | | | | | 75 | | | | | 80 |

| Asn | Gln | Asn | Cys | Thr | Lys | Asp | Met | Leu | Cys | Ser | Ser | Val | Thr | Asn | Arg |
|---|---|---|---|---|---|---|---|---|---|---|---|---|---|---|---|
| | | | | 85 | | | | | 90 | | | | | 95 | |

| Cys | Asp | Cys | Gln | Asp | Phe | Lys | Cys | Pro | Gln | Ser | Tyr | Cys | Pro | His | Gly |
|---|---|---|---|---|---|---|---|---|---|---|---|---|---|---|---|
| | | | | 100 | | | | | 105 | | | | | 110 | |

| Phe | Glu | Thr | Asp | Glu | Asn | Glu | Cys | Glu | Val | Cys | Ile | Cys | Lys | Lys | Pro |
|---|---|---|---|---|---|---|---|---|---|---|---|---|---|---|---|
| | | | 115 | | | | | 120 | | | | | 125 | | |

| Thr | Cys | Ala | Asn | Cys | Gly | Lys | Thr | Thr | Lys | Lys | Pro | Arg | Thr | Ile | Asp |
|---|---|---|---|---|---|---|---|---|---|---|---|---|---|---|---|
| | | | 130 | | | | | 135 | | | | | 140 | | |

| Arg | Leu | Lys | Asn | Trp | Phe | Lys | Lys | Lys | Phe | Gly | Lys | Val | Leu | Glu | Thr |

```
         145                    150                    155                    160
    Asn  Asp  Cys  Arg  Leu  Lys  Leu  Gln  Leu  Thr  His  Tyr  Leu  Ile  Ile  Asp
                        165                    170                    175
    Ala  Phe  Pro  Ser  Pro  Phe  Asp  Glu  Ile  Lys  Asn  Tyr  Ser  Gln  Lys  Lys
                        180                    185                    190
    Lys  Lys  Lys  Thr  Arg
                        195
```

( 2 ) INFORMATION FOR SEQ ID NO:25:

( i ) SEQUENCE CHARACTERISTICS:
      ( A ) LENGTH: 697 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:25:

```
CGGAATCTTG  TAAGGATAAT  AGATCTTGCC  GTAGCGATGA  ACGTTGTGAT  AACTTCACCA    60

AAGTGTGTGT  TCCTCAATCA  TTCGAAGAAA  TGAAAATGTG  TTGGAACAAA  GGTTGCCCAT   120

GTGGTCAGCG  ATGCAACTTA  CATAGAAATG  AATGCGAAGT  AATAGCAGAG  AATATTGAAT   180

GCCAAGAGGA  AGAATGTCCT  GATCCTTACT  TATGCAGTCC  TGTGACCAAT  CGATGTGAGT   240

GCACTCCTGT  ACTCTGCCGA  ATGTACTGCA  AGTTTTGGGC  CAAAGACGAA  AAAGGCTGCG   300

AGATATGTAA  ATGTGAAGAG  CTGTGCCAGA  ATCAAAATTG  TACCAAAGAC  ATGTTGTGCA   360

GCAGCGTAAC  TAACAGATGT  GATTGTCAAG  ACTTCAAATG  TCCACAATCT  TACTGTCCTC   420

ACGGATTCGA  AACTGATGAG  AACGAATGCG  AAGTTTGTAT  CTGCAAAAAA  CCAACTTGTG   480

CCAACTGCGG  CAAAACAACC  AAGAAACCAA  GAACTATTGA  CAGACTAAAA  AATTGGTTCA   540

AGAAGAAATT  TGGAAAATAA  GTTCTTGAAA  CCAACGATTG  TAGATTAAAA  TTACAATTAA   600

CACATTATTG  ATTAATTATT  GATGCATTTC  CATCTCCATT  TGATTGAGAA  ATAAAATAAA   660

ATTACTAAAG  TCAAAAAAAA  AAAAAAAAAA  CTCGAGG                              697
```